US007205310B2

(12) United States Patent
Konradi et al.

(10) Patent No.: US 7,205,310 B2
(45) Date of Patent: Apr. 17, 2007

(54) PYRIMIDINE HYDANTOIN ANALOGUES WHICH INHIBIT LEUKOCYTE ADHESION MEDIATED BY VLA-4

(75) Inventors: Andrei W. Konradi, Burlingame, CA (US); Frank Stappenbeck, Seattle, WA (US); Michael A. Pleiss, Sunnyvale, CA (US); Christopher Semko, Fremont, CA (US); Jenifer L. Smith, South San Francisco, CA (US)

(73) Assignee: Elan Pharmaceuticals, Inc., South San Francisco, CA (US)

( * ) Notice: Subject to any disclaimer, the term of this patent is extended or adjusted under 35 U.S.C. 154(b) by 0 days.

(21) Appl. No.: 11/118,862

(22) Filed: Apr. 29, 2005

(65) Prior Publication Data

US 2005/0261324 A1 Nov. 24, 2005

Related U.S. Application Data

(60) Provisional application No. 60/566,784, filed on Apr. 30, 2004.

(51) Int. Cl.
*C07D 239/48* (2006.01)
*C07D 239/49* (2006.01)
*A61K 31/4166* (2006.01)
*A61K 31/506* (2006.01)
*A61P 11/06* (2006.01)
*A61P 19/02* (2006.01)

(52) U.S. Cl. ............. 514/275; 544/323; 544/324; 544/325

(58) Field of Classification Search ......... 544/323, 544/324, 325; 514/275
See application file for complete search history.

(56) References Cited

U.S. PATENT DOCUMENTS 5,510,332 A 4/1996 Kogan et al.
6,492,372 B1 12/2002 Konradi et al.

FOREIGN PATENT DOCUMENTS

| EP | 0 330 506 | 8/1989 |
|---|---|---|
| EP | 1 454 898 | 9/2004 |
| WO | WO 96/01644 | 1/1996 |
| WO | WO 99/10312 | 3/1999 |
| WO | WO 00/43372 | 7/2000 |
| WO | WO 01/54690 | 8/2001 |
| WO | WO 02/08203 | 1/2002 |
| WO | WO 03/053926 | 7/2003 |
| WO | WO 03/099809 | 12/2003 |
| WO | WO 05/000244 | 1/2005 |

OTHER PUBLICATIONS

Wolft Manfred E. "Burger's Medicinal Chemistry, 5ed, Part 1", John Wiley & Sons, 1995, pp. 975-977.*

Banker, G.S. et al, "Modern Pharmaceutics, 3ed.", Marcel Dekker, New York 1996, pp. 451 and 596.*
Yusuf-Makagiansar etal., Medical Research Reviews 22(2); 146-167, 2002.*
Abraham, W.M., et al. "a4-Integrins Mediate Antigen -induced Late Bronchial Responses and Prolonged Airway Hyperresponsiveness in Sheep." *J. Clin. Invest.* 93: 776-787 (1994).
Bao, L., et al. "Correlation of VLA-4 integrin expression with metastatic potential in various human tumour cell lines." *Diff.* 52: 239-246 (1993).
Baron, J.L., et al. "The Pathogenesis of Adeoptive Murine Autoimmune Diabetes Requires an Interaction between a4-Integrins and Vascular Cell Adhesion Molecule-1." *J. Clin. Invest.* 93: 1700-1708 (1994).
Baron, J.L., et al. "Surface Expression of a4 Integrin by CD4 T Cells is Required for Their Entry into Brain Parenchyma." *J. Exp. Med.* 177: 57-68 (1993).
Berlin, C., et al., "$\alpha 4\beta 7$ Integrin Mediates Lymphocyte Binding to the Mucosal Vascular Addressin MAdCAM-1" *Cell*, 74:185-195 (1993).
Briskin, M. J., et al. "Structural Requirements for Mucosal Vascular Addressin Binding to its Lymphocyte Receptor $\alpha_4\beta_7$," *J. Immunol.*, 156:719-726 (1996).
Cardarelli, P.M., et al., Cyclic RGD Peptide Inhibits $\alpha 4\beta 1$ Interaction with Connecting Segment 1 and Vascular Cell Adhesion Molecule *J. Biol. Chem.*, 296:1866818673 (1994).
Burkly, L.C., et al. "Protection Against Adoptive Transfer of Autoimmune Diabetes Mediated Through Very Late Antigent-4 Integrin." *Diabetes*. 43: 529-534 (1994).
Cybulsky, M.I., et al. "Endothelial Expression of a Mononuclear Leukocyte Adhesion Molecule During Atherogenesis." *Science*. 251: 788-791 (1991).
Elices, M.J., et al. "VCAM-1 on Activated Endothelium Interacts with the Leukocyte Integrin VLA-4 at a Site Distinct from the CLA-4/Fibronectin Binding Site." *Cell*. 60: 577-584 (1990).
Elices, M.J., et al. "Expression and Functional Significance of Alternatively Spliced CS1 Fibronecting in Rheumatoid Arthritis Microvasculature." J. Clin. Invest. 93: 405-41(1994).
Ferguson, T.A., et al. "Two integrin-binding peptides abrogate T cell-mediated immune response *in vivo*" *PNAS*, 88:8072-8076 (1991).
Hamann, A., et al. "Role of a4-Integrins in Lymphocute Homing to Mucosal Tissues in Vivo." *J. Immunology*. 152: 3283-3292 (1994).
Holzmann, B., et al. "Peyer's patch-specific lymphocyte homing receptors consist of a VLA-4-like $\alpha$ chain associated with either of two integrin $\beta$ chains, one of which is novel" *EMBO J.*, 8:1735-1741 (1989).

(Continued)

*Primary Examiner*—Venkataraman Balasubramanian
(74) *Attorney, Agent, or Firm*—Foley & Lardner LLP

(57) ABSTRACT

Disclosed are compounds which bind VLA-4 and/or LPAM-1. Certain of these compounds also inhibit leukocyte adhesion and, in particular, leukocyte adhesion mediated by VLA-4 and/or LPAM-1. Such compounds are useful in the treatment of inflammatory diseases in a mammalian patient, e.g., human, such as asthma, Alzheimer's disease, atherosclerosis, AIDS dementia, diabetes, inflammatory bowel disease, rheumatoid arthritis, tissue transplantation, tumor metastasis and myocardial ischemia. The compounds can also be administered for the treatment of inflammatory brain diseases such as multiple sclerosis.

19 Claims, No Drawings

OTHER PUBLICATIONS

Kawaguchi, S., et al. "VLA-4 Molecules on Tumor Cells Initiate an Adhesive Interaction with VCAM-1 Molecules on Endothelial Cell Surface." *Japanese J. Cancer Res*. 83: 1304-1316 (1992).

Lauri, D., et al. "Decreased adhesion to endothelial cells and matrix proteins of H-2Kb gene transfected tumour cells." *British J. Cancer*. 68: 862-867 (1993).

Li, H., et al. "An Atherogenic Diet Rapidly Induces VCAM-1, a Cytokine-Regulatable Mononuclear Leukocyte Adhesion Molecule, in Rabbit Aortic Endothelium." *Arterioscler. Thromb*. 13(2): 197-204 (1993).

Mulligan, M.S., et al. "Role of β1, β2 Integrins and ICAM-1 in Lung Injury after Deposition of IgG and IgA Immune Complexes." *J. Immunol*. 150(6): 2407-2417 (1993).

Okarhara, H., et al. "Involvement of Very Late Activation Antigen 4 (VLA-4) and Vascular Cell Adhesion Molecule 1(VCAM-1) in Tumor Necrosis Factor a Enhancement of Experimental Metastasis." *Can. Res*. 54: 3233-3236 (1994).

Osborn, L. "Leukocyte Adhesion to Endothelium in Inflammation." *Cell*. 62: 3-6 (1990).

Paavonen, T., et al. "In Vivo Evidence of the Role of a4β1-VCAM-1 Interaction in Sarcoma, but not in Carcinoma Extravasation." *Int. J. Can*. 58: 298 (1994).

Paul, L.C.,et al. "Monoclonal Antibodies Against LFA-1 and VLA-4 Inhibit Graft Vasculitis in Rat Cardiac Allografts." *Transpl. Proceed*. 25(1): 813-814 (1993).

Postigo, A.A., et al. "Increased Binding of Synovial T Lumphocytes from Rheumatoid Arthritis to Endothelial-Leukocyte Adhesion Molecule-1 (ELAM-1) and Vascular Cell Adhesion Molecule-1 (VCAM-1)." *J. Clin. Invest*. 89: 1445-1452 (1991).

Pretolani, M., et al. "Antibody to Very Late Activation Antigen 4 Prevents Antigen-induced Bronchial Hyperreactivity and Cellular Infiltration in the Guinea Pig Airways." *J. Exp. Med*. 180: 795-805 (1994).

Sasseville, V.G., et al. "Monocyte Adhesion to Endothelium in Simian Immunodeficiency Virus-Induced AIDS Encephalitis is Mediated by Vascular. Cell Adhesion Molecule-1/a4β1 Integrin Interactions." *Am. J. Path*. 144(1): 27-40 (1994).

Schadendorf, D., et al. "Tumour Progression and Metastatic Behaviour In Vivo Correlates with Integrin Expression on Melanocytic Tumours." *J. Path*. 170: 429-434 (1993).

Shroff, H.N., "Small Peptide Inhibitors of $\alpha_4\beta_7$ Mediated MAdCAM-1 Adhesion to Lymphocytes" *Bioorganic. Med., Chem. Lett.*, 6:2495-2500 (1996).

Springer, T.A. "Adhesion receptors of the immune system." *Nature*. 346: 425-434 (1990).

Vanderslice, P., "A Cyclic Hexapeptide Is a Potent Antagonist of $\alpha_4$ Integrins" *J. Immunol*, 158:1710-1718 (1997).

Van Dinther-Janssen, A.C.H.M., et al. "The VLA-4/VCAM-1 Pathway is Involved in Lymphocyte Adhesion to Endothelium in Rheumatoid Synovium." *J. Immunology*. 147(12): 4207-4210 (1991).

Van Dinther-Janssen, A.C.H.M., et al. "Role of the CS1 adhesion motif of fibronectin in T cell adhesion to synovial membrane and peripheral lymph node endothelium." *Annals. Rheumatic Dis*. 52: 672-676 (1993).

Vedder, N.B., et al. "Role of neutrophils in generalized reperfusion injury associated with resuscitation from shock." *Surgery*. 106: 509-516 (1989).

Yang, et al. "Inhibition of insultitis and prevention of diabetes in nonobese diabetic mice by blocking L-selecting and very late antigen 4 adhesion receptors." *Proc. Natl. Acad. Sci., USA*. 90: 10494-10498 (1993).

Yang, et al. "A predominant role of integrin $\alpha_4$ in the spontaneous development of autoimmune diabetes in nonobese diabetic mice" *PNAS.*, 91:12604-12608 (1994).

Yednock, T.A., et al. "Prevention of experimental autoimmune encephalomyelitis by antibodies against a4β1 integrin." *Nature* 356: 63 (1992).

* cited by examiner

PYRIMIDINE HYDANTOIN ANALOGUES WHICH INHIBIT LEUKOCYTE ADHESION MEDIATED BY VLA-4

CROSS-REFERENCE TO RELATED APPLICATION

This application claims the benefit of U.S. Ser. No. 60/566,784 filed Apr. 30, 2004, the disclosure of which is incorporated herein by reference in its entirety.

BACKGROUND OF THE INVENTION

1. Field of the Invention

This invention relates to compounds which inhibit leukocyte adhesion and, in particular, leukocyte adhesion mediated by VLA-4 and/or LPAM-1. This invention is also directed to pharmaceutical compositions comprising such compounds as well as to methods for treating conditions, particularly inflammatory conditions, mediated, at least in part, by VLA-4 and/or LPAM-1.

REFERENCES

The following publications, patents and patent applications are cited in this application as superscript numbers:

[1] Hemler and Takada, European Patent Application Publication No. 330,506, published Aug. 30, 1989
[2] Elices, et al., *Cell*, 60:577–584 (1990)
[3] Springer, *Nature*, 346:425–434 (1990)
[4] Osborn, *Cell*, 62:3–6 (1990)
[5] Vedder, et al., *Surgery*, 106:509 (1989)
[6] Pretolani, et al., *J. Exp. Med.*, 180:795 (1994)
[7] Abraham, et al., *J. Clin. Invest.*, 93:776 (1994)
[8] Mulligan, et al., *J. Immunology*, 150:2407 (1993)
[9] Cybulsky, et al., *Science*, 251:788 (1991)
[10] Li, et al., *Arterioscler. Thromb.*, 13:197 (1993)
[11] Sasseville, et al., *Am. J. Path.*, 144:27 (1994)
[12] Yang, et al., *Proc. Nat. Acad. Science (USA)*, 90:10494 (1993)
[13] Burkly, et al., *Diabetes*, 43:529 (1994)
[14] Baron, et al., *J. Clin. Invest.*, 93:1700 (1994)
[15] Hamann, et al., *J. Immunology*, 152:3238 (1994)
[16] Yednock, et al., *Nature*, 356:63 (1992)
[17] Baron, et al., *J. Exp. Med.*, 177:57 (1993)
[18] van Dinther-Janssen, et al., *J. Immunology*, 147:4207 (1991)
[19] van Dinther-Janssen, et al., *Annals. Rheumatic Dis.*, 52:672 (1993)
[20] Elices, et al., *J. Clin. Invest.*, 93:405 (1994)
[21] Postigo, et al., *J. Clin. Invest.*, 89:1445 (1991)
[22] Paul, et al., *Transpl. Proceed.*, 25:813 (1993)
[23] Okarhara, et al., *Can. Res.*, 54:3233 (1994)
[24] Paavonen, et al., *Int. J. Can.*, 58:298 (1994)
[25] Schadendorf, et al., *J. Path.*, 170:429 (1993)
[26] Bao, et al., *Diff.*, 52:239 (1993)
[27] Lauri, et al., *British J. Cancer*, 68:862 (1993)
[28] Kawaguchi, et al., *Japanese J. Cancer Res.*, 83:1304 (1992)
[29] Kogan, et al., U.S. Pat. No. 5,510,332, issued Apr. 23, 1996
[30] International Patent Appl. Publication No. WO 96/01644
[31] Holzmann, B and Weissman, I. *EMBO J.* 8, 1735, (1989)
[32] Berlin, C. et al., *Cell*: 74, 185, (1993)
[33] Yang, X-D. et al., *PNAS*, 91, 12604 (1994)
[34] Briskin, M. J. et al., *J. Immunol.* 156, 719, (1996)
[35] Cardarelli, P. M. et al., *J. Biol. Chem.* 269, 18668, (1994)
[36] Shroff, H. N. *Bioorganic. Med. Chem. Lett.* 6, 2495, (1996)
[37] Vanderslice, P. *J. Immunol.* 158, 1710, (1997)
[38] Ferguson, T. A. et al., *PNAS* 88, 8072, (1991)

All of the above publications, patents and patent applications are herein incorporated by reference in their entirety to the same extent as if each individual publication, patent or patent application was specifically and individually indicated to be incorporated by reference in its entirety.

2. State of the Art

VLA-4 (also referred to as $\alpha_4\beta_1$ integrin and CD49d/CD29), first identified by Hemler and Takada[1] is a member of the $\beta1$ integrin family of cell surface receptors, each of which comprises two subunits, an $\alpha$ chain and a $\beta$ chain. VLA-4 contains an $\alpha_4$ chain and a $\beta_1$ chain. There are at least nine $\beta_1$ integrins, all sharing the same $\beta_1$ chain and each having a distinct $\alpha$ chain. These nine receptors all bind a different complement of the various cell matrix molecules, such as fibronectin, laminin, and collagen. VLA-4, for example, binds to fibronectin. VLA-4 also binds non-matrix molecules that are expressed by endothelial and other cells. These non-matrix molecules include VCAM-1, which is expressed on cytokine-activated human umbilical vein endothelial cells in culture. Distinct epitopes of VLA-4 are responsible for the fibronectin and VCAM-1 binding activities and each activity has been shown to be inhibited independently.[2]

The $\alpha_4\beta_7$ integrin is also referred to as LPAM-1[31] and, like $\alpha_4\beta_1$, binds to VCAM-1 and fibronectin. In addition $\alpha_4\beta_7$ binds to an adhesion molecule believed to be involved in the homing of leukocytes to mucosal tissue termed MAdCAM-1.[32] The interaction between $\alpha_4\beta_7$ and MAdCAM-1 may also be important at sites of inflammation outside of mucosal tissue.[33]

Regions of the peptide sequence recognized by $\alpha_4\beta_7$ and $\alpha_4\beta_7$ when they bind to their ligands have been identified. The $\alpha_4\beta_7$ recognizes a LDT sequence (Leu-Asp-Thr-sequence) in MAdCAM-1.[34] There have been several reports of inhibitors of these interactions being designed from modifications of these short peptide sequences.[35-37] It has also been reported that a short peptide sequence derived from the $\alpha_4\beta_1$ binding site in fibronectin can inhibit a contact hypersensitivity reaction in a trinitrochlorobenzene sensitized mouse.[38]

Intercellular adhesion mediated by VLA-4, LPAM-1 and/or other cell surface receptors is associated with a number of inflammatory responses. At the site of an injury or other inflammatory stimulus, activated vascular endothelial cells express molecules that are adhesive for leukocytes. The mechanics of leukocyte adhesion to endothelial cells involves, in part, the recognition and binding of cell surface receptors on leukocytes to the corresponding cell surface molecules on endothelial cells. Once bound, the leukocytes migrate across the blood vessel wall to enter the injured site and release chemical mediators to combat infection. For reviews of adhesion receptors of the immune system, see, for example, Springer[3] and Osborn[4].

Inflammatory brain disorders, such as experimental autoimmune encephalomyelitis (EAE), multiple sclerosis (MS) and meningitis, are examples of central nervous system disorders in which the endothelium/leukocyte adhesion mechanism results in destruction to otherwise healthy brain tissue. Large numbers of leukocytes migrate across the blood brain barrier (BBB) in subjects with these inflammatory diseases. The leukocytes release toxic mediators that cause extensive tissue damage resulting in impaired nerve conduction and paralysis.

In other organ systems, tissue damage also occurs via an adhesion mechanism resulting in migration or activation of leukocytes. For example, it has been shown that the initial insult following myocardial ischemia to heart tissue can be further complicated by leukocyte entry to the injured tissue causing still further insult (Vedder et al.[5]). Other inflammatory or medical conditions mediated by an adhesion mechanism include, by way of example, asthma,[6-8] Alzheimer's disease, atherosclerosis,[9-10] AIDS dementia,[11] diabetes[12-14] (including acute juvenile onset diabetes), inflammatory bowel disease[15] (including ulcerative colitis and Crohn's disease), multiple sclerosis,[16-17] rheumatoid arthritis,[18-21] tissue transplantation,[22] tumor metastasis,[23-28] meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

The alpha 4 subgroup of integrins are predominantly expressed on leukocytes and their inhibition would be beneficial in treating, preventing or ameliorating a disease mediated at least in part by VLA-4 and/or LPAM-1. However, because of the ubiquitous distribution and wide range of functions performed by other members of the integrin family it is very important to be able to identify selective inhibitors of the alpha 4 subgroup.

In view of the above, assays for determining the VLA-4 and/or LPAM-1 levels in a biological sample containing VLA-4 would be useful, for example, to diagnosis VLA-4 and/or LPAM-1 mediated conditions. Additionally, despite these advances in the understanding of leukocyte adhesion, the art has only recently addressed the use of inhibitors of adhesion in the treatment of inflammatory brain diseases and other inflammatory conditions.[29,30] The present invention addresses these and other needs.

SUMMARY OF THE INVENTION

This invention provides compounds which bind to VLA-4 and/or LPAM-1. Such compounds can be used, for example, to assay for the presence of VLA-4 and/or LPAM-1 in a sample. They can also be used in pharmaceutical compositions to inhibit cellular adhesion mediated by VLA-4 and/or LPAM-1, for example, binding of VCAM-1 to VLA-4 and MADCAM-1 to LPAM-1. The compounds of this invention have a binding affinity to VLA-4 and/or LPAM-1 as expressed by an $IC_{50}$ of about 15 μM or less as measured using the procedures such as those described in Example A and/or Example B below.

Accordingly, in one of its composition aspects, this invention is directed to a compound of Formula I:

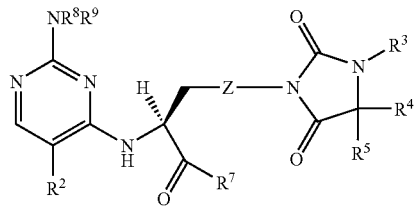

I wherein:
Z is selected from the group consisting of aryl, substituted aryl, heteroaryl or substituted heteroaryl;

$R^2$ is selected from the group consisting of hydrogen, alkyl, substituted alkyl, aryl, substituted aryl, heteroaryl, substituted heteroaryl, and —$NRR^1$ wherein each of R and $R^1$ is independently selected from the group consisting of hydrogen, alkyl, substituted alkyl, alkenyl, substituted alkenyl, alkynyl, substituted alkynyl, acyl, aminoacyl, and —$SO_2$—$R^6$, where $R^6$ is selected from the group consisting of alkyl, substituted alkyl, amino, substituted amino, cycloalkyl, substituted cycloalkyl, heterocyclic, substituted heterocyclic, aryl, substituted aryl, heteroaryl, and substituted heteroaryl;

$R^3$, $R^4$ and $R^5$ are independently selected from the group consisting of hydrogen, alkyl, substituted alkyl, alkoxy and substituted alkoxy provided that only one of $R^4$ and $R^5$ is alkoxy or substituted alkoxy;

or $R^3$ and $R^4$ together with the nitrogen atom pendent to $R^3$ and the carbon atom pendent to $R^4$, are cyclized to form a heterocyclic or substitute heterocyclic group;

or $R^4$ and $R^5$ together with the carbon atom pendent thereto are cyclized to form a cycloalkyl, substituted cycloalkyl, heterocyclic, or substituted heterocyclic group;

$R^7$ is selected from the group consisting of hydroxy, alkoxy, substituted alkoxy, phenoxy and substituted phenoxy;

$R^8$ and $R^9$ are independently selected from the group consisting of hydrogen, alkyl, substituted alkyl, cycloalkyl, and substituted cycloalkyl or $R^8$ and $R^9$, together with the nitrogen atom pendent thereto, form a heterocyclic or substituted heterocyclic group;

or a stereoisomer, prodrug, or pharmaceutically acceptable salt thereof.

In another of its composition aspects, this invention is directed to a compound of Formula Ia:

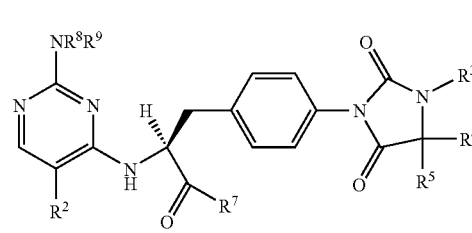

Ia wherein:
$R^2$ is selected from the group consisting of hydrogen, alkyl, substituted alkyl, aryl, substituted aryl, heteroaryl, substituted heteroaryl, and —$NRR^1$ wherein each of R and $R^1$ is independently selected from the group consisting of hydrogen, alkyl, substituted alkyl, alkenyl, substituted alkenyl, alkynyl, substituted alkynyl, acyl, aminoacyl, and —$SO_2$—$R^6$, where $R^6$ is selected from the group consisting of alkyl, substituted alkyl, amino, substituted amino, cycloalkyl, substituted cycloalkyl, heterocyclic, substituted heterocyclic, aryl, substituted aryl, heteroaryl, and substituted heteroaryl;

$R^3$, $R^4$ and $R^5$ are independently selected from the group consisting of hydrogen, alkyl, substituted alkyl, alkoxy and substituted alkoxy provided that only one of $R^4$ and $R^5$ is alkoxy or substituted alkoxy;

or $R^3$ and $R^4$ together with the nitrogen atom pendent to $R^3$ and the carbon atom pendent to $R^4$, are cyclized to form a heterocyclic or substitute heterocyclic group;

or $R^4$ and $R^5$ together with the carbon atom pendent thereto are cyclized to form a cycloalkyl, substituted cycloalkyl, heterocyclic, or substituted heterocyclic group;

$R^7$ is selected from the group consisting of hydroxy, alkoxy, substituted alkoxy, phenoxy and substituted phenoxy;

$R^8$ and $R^9$ are independently selected from the group consisting of hydrogen, alkyl, substituted alkyl, cycloalkyl, and substituted cycloalkyl or $R^8$ and $R^9$, together with the nitrogen atom pendent thereto, form a heterocyclic or substituted heterocyclic group;

or a stereoisomer, prodrug, or pharmaceutically acceptable salt thereof.

In still another of its composition aspects, this invention is directed to a compound of Formula Ib:

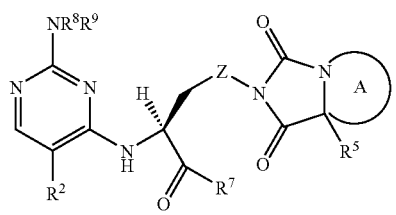

Ib wherein:

Z is selected from the group consisting of aryl, substituted aryl, heteroaryl or substituted heteroaryl;

$R^2$ is selected from the group consisting of hydrogen, alkyl, substituted alkyl, aryl, substituted aryl, heteroaryl, substituted heteroaryl, and —$NRR^1$ wherein each of R and $R^1$ is independently selected from the group consisting of hydrogen, alkyl, substituted alkyl, alkenyl, substituted alkenyl, alkynyl, substituted alkynyl, acyl, aminoacyl, and —$SO_2$—$R^6$, where $R^6$ is selected from the group consisting of alkyl, substituted alkyl, amino, substituted amino, cycloalkyl, substituted cycloalkyl, heterocyclic, substituted heterocyclic, aryl, substituted aryl, heteroaryl, and substituted heteroaryl;

$R^5$ is selected from the group consisting of hydrogen, alkyl, substituted alkyl, alkoxy and substituted alkoxy;

A, together with the nitrogen and carbon atoms pendent thereto, forms a 3 to 6 membered heterocyclic or substitute heterocyclic group;

$R^7$ is selected from the group consisting of hydroxy, alkoxy, substituted alkoxy, phenoxy and substituted phenoxy;

$R^8$ and $R^9$ are independently selected from the group consisting of hydrogen, alkyl, substituted alkyl, cycloalkyl, and substituted cycloalkyl or $R^8$ and $R^9$, together with the nitrogen atom pendent thereto, form a heterocyclic or substituted heterocyclic group;

or a stereoisomer, prodrug, or pharmaceutically acceptable salt thereof.

In a further composition aspect of this invention, this invention is directed to a compound of Formula Ic:

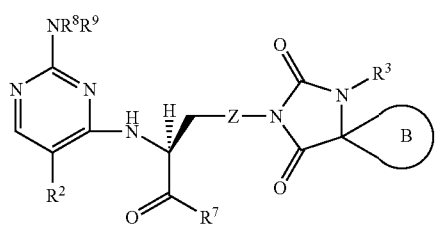

Ic wherein:

Z is selected from the group consisting of aryl, substituted aryl, heteroaryl or substituted heteroaryl;

$R^2$ is selected from the group consisting of hydrogen, alkyl, substituted alkyl, aryl, substituted aryl, heteroaryl, substituted heteroaryl, and —$NRR^1$ wherein each of R and $R^1$ is independently selected from the group consisting of hydrogen, alkyl, substituted alkyl, alkenyl, substituted alkenyl, alkynyl, substituted alkynyl, acyl, aminoacyl, and —$SO_2$—$R^6$, where $R^6$ is selected from the group consisting of alkyl, substituted alkyl, amino, substituted amino, cycloalkyl, substituted cycloalkyl, heterocyclic, substituted heterocyclic, aryl, substituted aryl, heteroaryl, and substituted heteroaryl;

$R^3$ is selected from the group consisting of hydrogen, alkyl, substituted alkyl, alkoxy;

B, together with the carbon atom pendent thereto, forms a 3 to 6 membered cycloalkyl, substituted cycloalkyl, heterocyclic, or substituted heterocyclic group;

$R^7$ is selected from the group consisting of hydroxy, alkoxy, substituted alkoxy, phenoxy and substituted phenoxy;

$R^8$ and $R^9$ are independently selected from the group consisting of hydrogen, alkyl, substituted alkyl, cycloalkyl, and substituted cycloalkyl or $R^8$ and $R^9$, together with the nitrogen atom pendent thereto, form a heterocyclic or substituted heterocyclic group;

or a stereoisomer, prodrug, or pharmaceutically acceptable salt thereof.

In a preferred embodiment for Formulas I, Ib and Ic, Z is a 6-membered aryl, substituted aryl, heteroaryl, or substituted heteroaryl group. More preferably, Z is selected from phenyl, substituted phenyl, pyridine, substituted pyridine, pyridazine, substituted pyridazine, pyrazine, and substituted pyrazine.

In another preferred embodiment, $R^2$ is selected from alkyl, aryl and —$NRR^1$ wherein each of R and $R^1$ is independently selected from the group consisting of hydrogen, alkyl, substituted alkyl, alkenyl, substituted alkenyl, alkynyl, substituted alkynyl, acyl, and —$SO_2$—$R^6$, where $R^6$ is selected from the group consisting of alkyl, substituted alkyl, amino, substituted amino, cycloalkyl, substituted cycloalkyl, heterocyclic, substituted heterocyclic, aryl, substituted aryl, heteroaryl, and substituted heteroaryl. More preferably, $R^2$ is 2,2,2-trifluoroethyl or $R^2$ is $NRR^1$ where $R^1$ is selected from 4-fluoro-phenylsulfonyl, acetyl, methylsulfonyl, trifluoroacetyl, ethyl, pyrrolidinyl-carbonyl, and furan-2-oyl.

In another preferred embodiment, $R^8$ and $R^9$ are independently selected from methyl and ethyl and, even more preferably, $R^8$ and $R^9$ are both ethyl.

In still another preferred embodiment, $R^7$ is hydroxyl, methoxy or ethoxy.

In compounds of Formula I and Ia, non-cyclized $R^3$ substituents are preferably methyl or ethyl.

In compounds of Formula I and Ia, non-cyclized $R^4$ and $R^5$ substituents are preferably independently selected from hydrogen or methyl.

In compounds of Formula I and Ia, cyclized $R^3$ and $R^4$ are preferably pyrrolindinyl.

In compounds of Formula Ib, B is a cyclopropyl or cyclohexyl.

In one of its pharmaceutical composition aspect, this invention is directed to a pharmaceutical composition comprising an effective amount of a compound according to any of Formulas I, Ia, Ib, Ic, or a stereoisomer, prodrug, or pharmaceutically acceptable salt thereof, and a pharmaceutically inert carrier.

In one of its method aspects, this invention is directed to a method for treating a disease mediated, at least in part, by VLA-4 and/or LPAM-1 in a patient, which method comprises administering a pharmaceutical composition comprising a pharmaceutically acceptable carrier and a therapeutically effective amount of a compound of Formulas I, Ia, Ib Ic, or a stereoisomer, prodrug, or pharmaceutically acceptable salt thereof.

This invention also provides methods for binding VLA-4 and/or LPAM-1 in a biological sample which method comprises contacting the biological sample with a compound of this invention under conditions wherein said compound binds to VLA-4 and/or LPAM-1.

The pharmaceutical compositions may be used to treat disease conditions mediated by VLA-4 and/or LPAM-1 or leucocyte adhesion. Such disease conditions include, by way of example, asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

Other disease conditions include, but are not limited to, inflammatory conditions such as erythema nodosum, allergic conjunctivitis, optic neuritis, uveitis, allergic rhinitis, ankylosing spondylitis, psoriatic arthritis, vasculitis, Reiter's syndrome, systemic lupus erythematosus, progressive systemic sclerosis, polymyositis, dermatomyositis, Wegner's granulomatosis, aortitis, sarcoidosis, lymphocytopenia, temporal arteritis, pericarditis, myocarditis, congestive heart failure, polyarteritis nodosa, hypersensitivity syndromes, allergy, hypereosinophilic syndromes, Churg-Strauss syndrome, chronic obstructive pulmonary disease, hypersensitivity pneumonitis, chronic active hepatitis, interstitial cystitis, autoimmune endocrine failure, primary biliary cirrhosis, autoimmune aplastic anemia, chronic persistent hepatitis and thyroiditis.

Preferred compounds of this invention include those set forth in the Table I below:

TABLE I

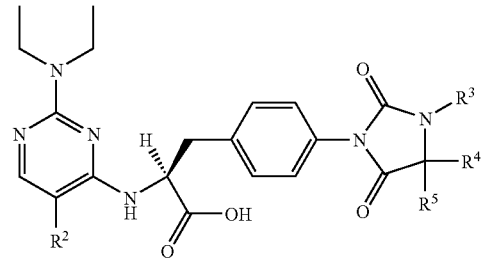

I

| Cpd # | $R^2$ | R | $R^1$ | $R^3$ | $R^4$ | $R^5$ |
|---|---|---|---|---|---|---|
| 1 | $NRR^1$ | methyl | 4-fluoro-phenylsulfonyl | methyl | methyl | methyl |
| 2 | $NRR^1$ | methyl | 4-fluoro-phenylsulfonyl | $R^3$ and $R^4$ cyclize to form a five-membered ring | | H |
| 3 | $NRR^1$ | methyl | 4-fluoro-phenylsulfonyl | methyl | H | H |
| 4 | $NRR^1$ | isopropyl | acetyl | $R^3$ and $R^4$ cyclize to form a five-membered ring | | H |
| 5 | $NRR^1$ | isopropyl | acetyl | $R^3$ and $R^4$ cyclize to form a five-membered ring | | H |
| 6 | $NRR^1$ | isopropyl | methylsulfonyl | $R^3$ and $R^4$ cyclize to form a five-membered ring | | H |
| 7 | $NRR^1$ | ethyl | acetyl | methyl | $R^4$ and $R^5$ cyclize to form cyclopropyl | |
| 8 | $NRR^1$ | ethyl | acetyl | methyl | $R^4$ and $R^5$ cyclize to form cyclohexyl | |
| 9 | $NRR^1$ | isopropyl | methylsulfonyl | methyl | $R^4$ and $R^5$ cyclize to form cyclohexyl | |
| 10 | $NRR^1$ | isopropyl | methylsulfonyl | methyl | $R^4$ and $R^5$ cyclize to form cyclopropyl | |
| 11 | $NRR^1$ | isopropyl | trifluoroacetyl | methyl | $R^4$ and $R^5$ cyclize to form cyclopropyl | |
| 12 | $NRR^1$ | isopropyl | trifluoroacetyl | methyl | $R^4$ and $R^5$ cyclize to form cyclohexyl | |
| 13 | $NRR^1$ | ethyl | trifluoroacetyl | methyl | $R^4$ and $R^5$ cyclize to form cyclohexyl | |
| 14 | $NRR^1$ | ethyl | ethyl | methyl | $R^4$ and $R^5$ cyclize to form cyclohexyl | |
| 15 | $NRR^1$ | ethyl | trifluoroacetyl | methyl | $R^4$ and $R^5$ cyclize to form cyclopropyl | |
| 16 | $NRR^1$ | ethyl | pyrrolidinyl-carbonyl | methyl | $R^4$ and $R^5$ cyclize to form cyclohexyl | |

TABLE I-continued

| Cpd # | R² | R | R¹ | R³ | R⁴ | R⁵ |
|---|---|---|---|---|---|---|
| 17 | NRR¹ | ethyl | furan-2-oyl | methyl | R⁴ and R⁵ cyclize to form cyclohexyl | |
| 18 | NRR¹ | ethyl | trifluoroacetyl | ethyl | R⁴ and R⁵ cyclize to form cyclohexyl | |
| 19 | 2,2,2-trifluoroethyl | — | — | R³ and R⁴ cyclize to form a five-membered ring | | H |

Particularly preferred compounds include the following compounds:

(S)-2-{5-[N-(4-fluorophenylsulfonyl)-N-methyl-amino]-2-(N',N'-diethylamino)-pyrimidin-4-ylamino}-3-[4-(3,4,4-trimethyl-2,5-dioxoimidazolidin-1-yl)phenyl]propanoic acid (1);

(S)-2-{5-[N-(4-fluorophenylsulfonyl)-N-methyl-amino]-2-(N',N'-diethylamino)-pyrimidin-4-ylamino}-3-[4-(1,3-dioxo-(S)-tetrahydro-2H-pyrrolo[1,2-e]imidazol-2-yl)phenyl]propanoic acid (2);

(S)-2-{5-[N-(4-fluorophenylsulfonyl)-N-methyl-amino]-2-(N',N'-diethylamino)-pyrimidin-4-ylamino}-3-[4-(3-methyl-2,5-dioxoimidazolidin-1-yl)phenyl]propanoic acid (3);

(S)-2-{5-[N-acetyl-N-isopropyl-amino]-2-(N',N'-diethylamino)-pyrimidin-4-ylamino}-3-[4-(1,3-dioxo-(S)-tetrahydro-2H-pyrrolo[1,2-e]imidazol-2-yl)phenyl]propanoic acid (4);

(S)-2-{5-[N-acetyl-N-isopropyl-amino]-2-(N',N'-diethylamino)-pyrimidin-4-ylamino}-3-[4-(1,3-dioxo-(R)-tetrahydro-2H-pyrrolo[1,2-e]imidazol-2-yl)phenyl]propanoic acid (5);

(S)-2-{5-[N-(methylsulfonyl)-N-isopropyl-amino]-2-(N',N'-diethylamino)-pyrimidin-4-ylamino}-3-[4-(1,3-dioxo-(S)-tetrahydro-2H-pyrrolo[1,2-e]imidazol-2-yl)phenyl]propanoic acid (6);

(S)-2-{5-[N-acetyl-N-ethyl-amino]-2-(N',N'-diethylamino)-pyrimidin-4-ylamino}-3-[4-(4-methyl-4,6-diaza-spiro[2.4]heptane-5,7-dione-6-yl)phenyl]propanoic acid (7);

(S)-2-{5-[N-acetyl-N-ethyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid (8);

(S)-2-{5-[N-(methylsulfonyl)-N-isopropyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid (9);

(S)-2-{5-[N-(methylsulfonyl)-N-isopropyl-amino]-2-(N',N'-diethylamino)-pyrimidin-4-ylamino}-3-[4-(4-methyl-4,6-diaza-spiro[2.4]heptane-5,7-dione-6-yl)phenyl]propanoic acid (10);

(S)-2-{5-[N-trifluoroacetyl-N-isopropyl-amino]-2-(N',N'-diethylamino)-pyrimidin-4-ylamino}-3-[4-(4-methyl-4,6-diaza-spiro[2.4]heptane-5,7-dione-6-yl)phenyl]propanoic acid (11);

(S)-2-{5-[N-trifluoroacetyl-N-isopropyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid (12);

(S)-2-{5-[N-trifluoroacetyl-N-ethyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid (13);

(S)-2-{5-[2,5-bis(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid (14);

(S)-2-{5-[N-trifluoroacetyl-N-ethyl-amino]-2-(N',N'-diethylamino)-pyrimidin-4-ylamino}-3-[4-(4-methyl-4,6-diaza-spiro[2.4]heptane-5,7-dione-6-yl)phenyl]propanoic acid (15);

(S)-2-{5-[N-(pyrrolidinyl-carbonyl)-N-ethyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid (16);

(S)-2-{5-[N-(furan-2-ylcarbonyl)-N-ethyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid (17); and (S)-2-{5-[N-trifluoroacetyl-N-ethyl-amino]-2-(N',N'-diethylamino)-pyrimidin-4-ylamino}-3-[4-(3-ethyl-4-(4-methyl-2,4-diaza-spiro[4.5]decane-1,3-dion-2-yl)-2,5-dioxoimidazolidin-1-yl)phenyl]propanoic acid (18);

(S)-2-{5-(2,2,2-trifluoroethyl)-2-(N',N'-diethylamino)-pyrimidin-4-ylamino}-3-[4-(1,3-dioxo-(S)-tetrahydro-2H-pyrrolo[1,2-e]imidazol-2-yl)phenyl]propanoic acid (19);

or a stereoisomer, prodrug, or pharmaceutically acceptable salt thereof.

DETAILED DESCRIPTION OF THE INVENTION

As above, this invention relates to compounds which inhibit leukocyte adhesion and, in particular, leukocyte adhesion mediated by VLA-4 and/or LPAM-1. However, prior to describing this invention in further detail, the following terms will first be defined.

Definitions

Unless otherwise limited by a specific recitation herein, the following terms have the following meanings:

"Alkyl" refers to monovalent alkyl groups having from 1 to 10 carbon atoms, preferably from 1 to 5 carbon atoms and more preferably 1 to 3 carbon atoms. This term is exemplified by groups such as methyl, ethyl, n-propyl, iso-propyl, n-butyl, isobutyl, sec-butyl, t-butyl, n-pentyl, isoamyl, n-hexyl and the like.

"Substituted alkyl" refers to a monovalent alkyl group having from 1 to 3, and preferably 1 to 2, substituents selected from the group consisting of alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Alkoxy" refers to the group "alkyl-O—" which includes, by way of example, methoxy, ethoxy, n-propoxy, iso-propoxy, n-butoxy, t-butoxy, sec-butoxy, n-pentoxy and the like.

"Substituted alkoxy" refers to the group "substituted alkyl-O—".

"Acyl" refers to the groups H—C(O)—, alkyl-C(O)—, substituted alkyl-C(O)—, alkenyl-C(O)—, substituted alkenyl-C(O)—, cycloalkyl-C(O)—, substituted cycloalkyl-C(O)—, aryl-C(O)—, substituted aryl-C(O)—, heteroaryl-C(O)—, substituted heteroaryl-C(O), heterocyclic-C(O)—, and substituted heterocyclic-C(O)—.

"Aminoacyl" refers to the group —C(O)NR$^{10}$R$^{10}$ where each R$^{10}$ is independently selected from the group consisting of hydrogen, alkyl, substituted alkyl, alkenyl, substituted alkenyl, aryl, substituted aryl, cycloalkyl, substituted cycloalkyl, heteroaryl, substituted heteroaryl, heterocyclic, substituted heterocyclic and where each R$^{10}$ is joined to form, together with the nitrogen atom to which they are both attached, a heterocyclic or substituted heterocyclic ring.

"Alkenyl" refers to a monovalent alkenyl group having from 2 to 6 carbon atoms and more preferably 2 to 4 carbon atoms and having at least 1 and preferably from 1–2 sites of alkenyl unsaturation. The term "alkenyl" encompasses any and all combinations of cis and trans isomers arising from the presence of unsaturation.

"Substituted alkenyl" refers to alkenyl groups having from 1 to 3 substituents, and preferably 1 to 2 substituents, selected from the group consisting of alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic provided that any hydroxyl substitution is not on a vinyl carbon atom "Alkynyl" refers to alkynyl group having from 2 to 10 carbon atoms and more prefereably 3 to 6 carbon atoms and having at least 1 and preferably from 1–2 sites of alkynyl unsaturation. The term "alkynylene" refers to a divalent substituted alkynylene group.

"Substituted alkynyl" refers to alkynyl groups having from 1 to 5, preferably 1 to 3 substitutents, selected from the same group of substitutents as defined for substituted alkyl. The term "substituted alkynylene" refers to a divalent substituted alkynylene group.

"Amino" refers to the group —NH$_2$.

"Substituted amino" refers to the group —NR'R'' where R' and R'' are independently selected from the group consisting of hydrogen, alkyl, substituted alkyl, alkenyl, substituted alkenyl, aryl, substituted aryl, cycloalkyl, substituted cycloalkyl, heteroaryl, substituted heteroaryl, heterocyclic, substituted heterocyclic and where R' and R'' are joined, together with the nitrogen bound thereto, to form a heterocyclic or substituted heterocylic group provided that R' and R'' are both not hydrogen. When R' is hydrogen and R'' is alkyl, the substituted amino group is sometimes referred to herein as alkylamino. When R' and R'' are alkyl, the substituted amino group is sometimes referred to herein as dialkylamino.

"Acylamino" refers to the groups —NR$^{11}$C(O)alkyl, —NR$^{11}$C(O)substituted alkyl, —NR$^{11}$C(O)cycloalkyl, —NR$^{11}$C(O)substituted cycloalkyl, —NR$^{11}$C(O)alkenyl, —NR$^{11}$C(O)substituted alkenyl, —NR$^{11}$C(O)aryl, —NR$^{11}$C(O)substituted aryl, —NR$^{11}$C(O)heteroaryl, —NR$^{11}$C(O)substituted heteroaryl, —NR$^{11}$C(O)heterocyclic, and —NR$^{11}$C(O)substituted heterocyclic where R$^{11}$ is hydrogen or alkyl.

"Aryl" or "Ar" refers to a monovalent aromatic carbocyclic group of from 6 to 14 carbon atoms having a single ring (e.g., phenyl) or multiple condensed rings (e.g., naphthyl or anthryl) which condensed rings may or may not be aromatic (e.g., 2-benzoxazolinone, 2H-1,4-benzoxazin-3(4H)-one-7-yl, and the like) provided that the point of attachment is to an aromatic ring atom. Preferred aryls include phenyl and naphthyl, e.g, 2-naphthyl.

"Substituted aryl" refers to aryl groups which are substituted with from 1 to 3 substituents, and preferably 1 to 2 substituents, selected from the group consisting of hydroxy, acyl, acylamino, alkyl, substituted alkyl, alkoxy, substituted alkoxy, alkenyl, substituted alkenyl, amino, substituted amino, aminoacyl, aryl, substituted aryl, aryloxy, substituted aryloxy, cycloalkoxy, substituted cycloalkoxy, carboxyl, carboxyl esters, cyano, cycloalkyl, substituted cycloalkyl, halo, nitro, heteroaryl, substituted heteroaryl, heterocyclic, substituted heterocyclic, heteroaryloxy, substituted heteroaryloxy, heterocyclyloxy, and substituted heterocyclyloxy.

"Aryloxy" refers to the group aryl-O— that includes, by way of example, phenoxy, naphthoxy, and the like.

"Substituted aryloxy" refers to substituted aryl-O— groups. One particularly preferred substituted aryloxy is substituted phenoxy which is a phenoxy group substituted with 1 to 3 substituents defined above for substituted aryl.

"Carboxyl" refers to —COOH or pharmaceutically acceptable salts thereof.

"Carboxyl ester" refers to the group —C(O)OR$^{12}$ where R$^{12}$ is selected from the group consisting of alkyl, substituted alkyl, alkenyl, substitiuted alkenyl, cycloalkyl, substituted cycloalkyl, aryl, substituted aryl heteroaryl and substituted heteroaryl. Preferred carboxy ester groups include —C(O)O-alkyl, —C(O)O-substituted alkyl, —C(O)Oaryl, and —C(O)O-substituted aryl.

"Cycloalkyl" refers to monovalent cyclic alkyl groups of from 3 to 10 carbon atoms having single or multiple condensed rings which condensed rings may or may not be cycloalkyl provided that the point of attachment is to a cycloalkyl ring atom. Examples of cycloalkyl groups include, by way of example, adamantyl, cyclopropyl, cyclobutyl, cyclopentyl, cyclooctyl and the like.

"Substituted cycloalkyl" refers to a cycloalkyl group, having from 1 to 5 substituents selected from the group consisting of oxo (=O), thioxo (=S), alkyl, substituted alkyl, alkoxy, substituted alkoxy, acyl, acylamino, amino, substituted amino, aminoacyl, aryl, substituted aryl, aryloxy, substituted aryloxy, cyano, halogen, hydroxyl, nitro, carboxyl, carboxyl esters, cycloalkyl, substituted cycloalkyl, heteroaryl, substituted heteroaryl, heterocyclic, and substituted heterocyclic.

"Cycloalkoxy" refers to —O-cycloalkyl groups.

"Substituted cycloalkoxy" refers to —O-substituted cycloalkyl groups.

"Halo" or "halogen" refers to fluoro, chloro, bromo and iodo and preferably is fluoro or chloro.

"Heteroaryl" refers to a monovalent aromatic group of from 1 to 15 carbon atoms, preferably from 1 to 10 carbon atoms, and 1 to 4 heteroatoms selected from the group consisting of oxygen, nitrogen, and sulfur within the ring. Such heteroaryl groups can have a single ring (e.g., pyridyl or furyl) or multiple condensed rings (e.g., indolizinyl or benzothienyl). Preferred heteroaryls include quinolinyl, pyridyl, pyrrolyl, indolyl, thiophenyl, and furyl. The nitrogen and/or sulfur atoms within the ring can be optionally oxidized to provide for the N-oxide (N→O), S(O) and S(O)$_2$ functionalities.

"Substituted heteroaryl" refers to heteroaryl groups that are substituted with from 1 to 3 substituents selected from the same group of substituents defined for substituted aryl.

"Heteroaryloxy" refers to the group —O-heteroaryl and "substituted heteroaryloxy" refers to the group —O-substituted heteroaryl.

"Heterocycle" or "heterocyclic" refers to a monovalent saturated or unsaturated group having a single ring or multiple condensed rings, from 1 to 10 carbon atoms and from 1 to 4 hetero atoms selected from the group consisting of nitrogen, sulfur, and oxygen within the ring wherein, in fused ring systems, one or more the rings can be aryl or heteroaryl provided that the point of attachment is to a heterocyclic (non-aromatic) ring atom. The nitrogen and/or sulfur atoms within the ring can be optionally oxidized to provide for the N-oxide (N→O), S(O) and S(O)$_2$ functionalities.

"Substituted heterocyclic" refers to a heterocyclic group which is substituted with from 1 to 5 substituents as defined for substituted cycloalkyl.

Examples of heterocycles and heteroaryls include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothiazole, phenazine, isoxazole, phenoxazine, phenothiazine, imidazolidine, imidazoline, piperidine, piperazine, indoline, phthalimide, 1,2,3,4-tetrahydro-isoquinoline, 4,5,6,7-tetrahydro-benzo[b]thiophene, thiazole, thiazolidine, thiophene, benzo[b]thiophene, morpholinyl, thiomorpholinyl (also referred to as thiamorpholinyl), piperidinyl, pyrrolidine, tetrahydrofuranyl, and the like.

"Heterocyclyloxy" refers to the group —O-heterocyclic and "substituted heterocyclyloxy" refers to the group —O-substituted heterocyclic.

"Pharmaceutically acceptable salt" refers to pharmaceutically acceptable salts of a compound of Formula I which salts are derived from a variety of organic and inorganic counter ions well known in the art and include, by way of example only, sodium, potassium, calcium, magnesium, ammonium, tetraalkylammonium, and the like; and when the molecule contains a basic functionality, salts of organic or inorganic acids, such as hydrochloride, hydrobromide, tartrate, mesylate, acetate, maleate, oxalate and the like.

"Prodrug" refers to any pharmaceutically acceptable salt, ester, salt of an ester, or other derivative of a compound of this invention that is capable of directly or indirectly providing a compound of this invention or an active metabolite or residue thereof when administered to a subject. Particularly favored derivatives and prodrugs are those that increase the bioavailability of the compounds of this invention when such compounds are administered to a subject (e.g., by allowing an orally administered compound to be more readily absorbed into the blood) or which enhance delivery of the parent compound to a biological compartment (e.g., the brain or lymphatic system) relative to the parent species. Prodrugs include ester forms of the compounds of the invention. Examples of ester prodrugs include formate, acetate, propionate, butyrate, acrylate, and ethylsuccinate derivatives. An general overview of prodrugs is provided in T. Higuchi and V. Stella, Pro-drugs as Novel Delivery Systems, Vol. 14 of the A.C.S. Symposium Series, and in Edward B. Roche, ed., Bioreversible Carriers in Drug Design, American Pharmaceutical Association and Pergamon Press, 1987, both of which are incorporated herein by reference.

The compounds of the present invention are also defined herein based on the SMILES method of representing chemical formulas, as shown below. The following text based representation of Compound 1:

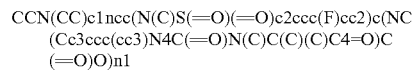
CCN(CC)c1ncc(N(C)S(=O)(=O)c2ccc(F)cc2)c(NC
(Cc3ccc(cc3)N4C(=O)N(C)C(C)(C)C4=O)C
(=O)O)n1 may be imported to commercially available chemical structure drawing programs. The program will interpret the text formula and display the following structure:

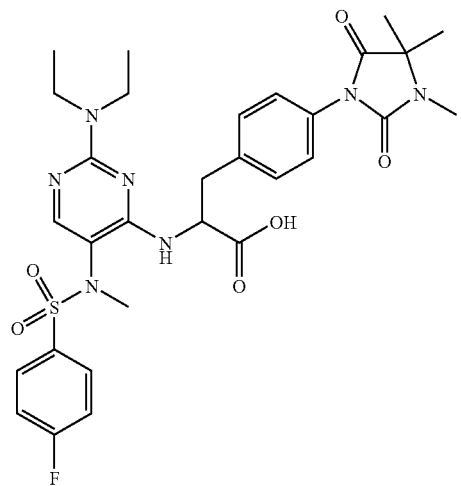

Although not explicitly depicted, it is understood that pharmaceutically acceptable salts of these compounds are included by the depicted structures.

Compound Preparation

The compounds of this invention can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and G. M. Wuts, *Protecting Groups in Organic Synthesis*, Third Edition, Wiley, New York, 1999, and references cited therein.

Furthermore, the compounds of this invention will typically contain one or more chiral centers. Accordingly, if desired, such compounds can be prepared or isolated as pure stereoisomers, i.e., as individual enantiomers or diastereomers, or as stereoisomer-enriched mixtures. All such stereoisomers (and enriched mixtures) are included within the scope of this invention, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1–15 (John Wiley and Sons, 1991), Rodd's Chemistry of Carbon Compounds, Volumes 1–5 and Supplementals (Elsevier Science Publishers, 1989), Organic Reactions, Volumes 1–40 (John Wiley and Sons, 1991), March's Advanced Organic Chemistry, (John Wiley and Sons, 4$^{th}$ Edition), and Larock's Comprehensive Organic Transformations (VCH Publishers Inc., 1989).

The compounds of the present invention, and intermediates useful in preparing the same, are preferably prepared as shown in the following Schemes. Scheme I, for example, illustrates the synthesis of compounds where Z is phenyl. It is understood, of course, that Scheme I is illustrative in purpose and that other substituted aryl, heteroaryl, and substituted heteroaryl groups can be employed in place of the phenyl group for the Z moiety. Scheme 1 illustrates a synthetic approach to compounds of the present invention, which may be specific to the elaboration of protected forms of 4'-nitrophenylalanine, and not protected forms of aminoacids other than 4'-nitro-phenylalanine. This synthetic approach takes advantage of the selective reduction of one nitro group in compound 552, without reduction of the other nitro group in compound 552. This synthetic approach may be not applicable to the elaboration of protected forms of phenylalanine derivatives, in which the phenyl group bears substituents in addition to the nitro group, or protected forms of phenylalanine analogs, in which the phenyl group is replaced by an aromatic heterocycle. Nonetheless, this synthetic approach is especially efficient for the elaboration of protected forms of 4'-nitrophenylalanine itself.

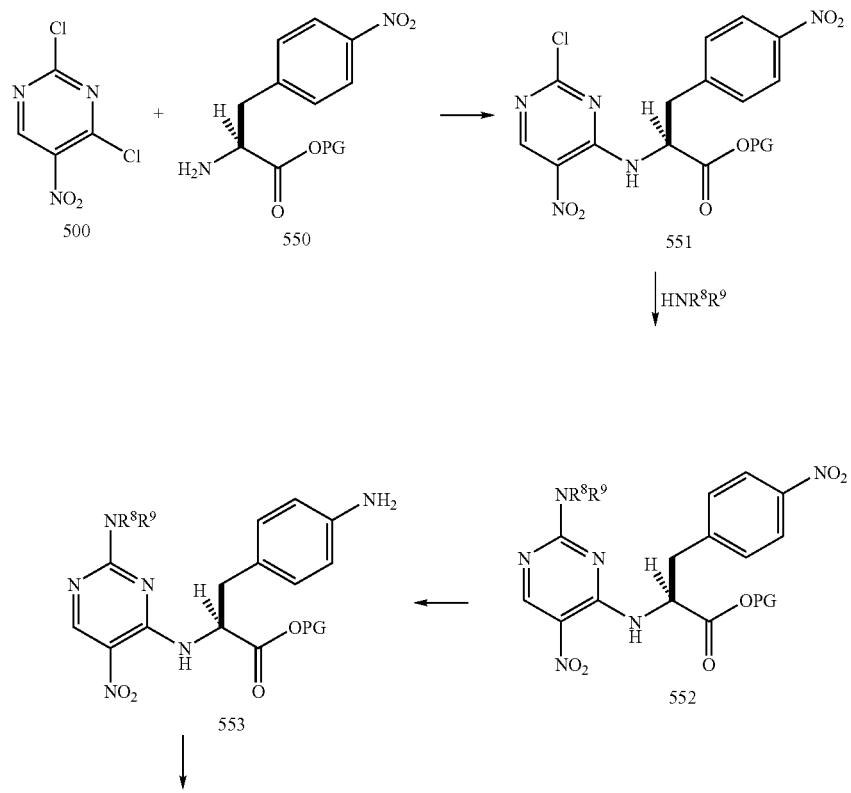

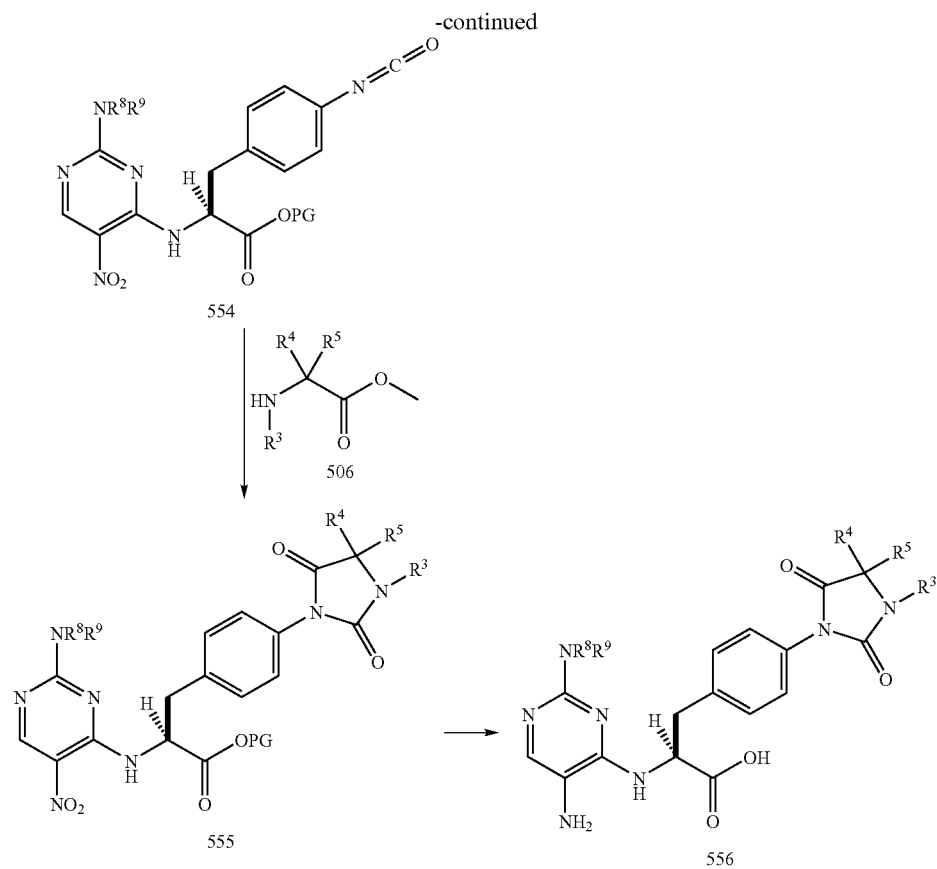

Specifically, 2,4-dichloro-5-nitropyrimidine, compound 500, is prepared according to the procedures of Whittaker, *J. Chem. Soc.* (1951), 1565; and Whittaker, *J. Chem. Soc.* (1953), 1646. Compound 500 is then coupled with a carboxyl protected 4-nitrophenylalanine derivative, compound 550, in the presence of a base, such as a tertiary amine, e.g., triethylamine, diisopropyl-ethylamine (DIPEA) in an inert solvent such as THF, $CH_2Cl_2$, DMF, and the like. The reaction is typically conducted at a temperature of from about –20 to about 37° C. for a period of time sufficient to effect substantial completion of the reaction which typically occurs in from about 10 minutes to 12 hours to afford N-(2-chloro-5-nitropyrimidin-5-yl)-p-nitrophenylalanine having a protected carboxyl group (PG), compound 551. This product can be recovered by conventional methods such as chromatography, filtration, evaporation, crystallization and the like or, alternatively, used in the next step without purification and/or isolation.

p-Nitrophenylalanine is commercially available in the free carboxyl form and is converted to the carboxyl protected form, compound 550, using conventional reaction conditions. For example, the carboxyl protecting group, PG, can be alkyl, benzyl, etc.

Alternatively, commercially available p-aminophenylalanine can be selectively blocked at the phenylamino group to provide for p-PG-aminophenylalanine. In yet another alternative 4'-Nitrophenylalanine t-butyl ester can be prepared according to Pender, et al., *J. Med. Chem.*, (2001) 44(1), 36–46.

N-(2-chloro-5-nitropyrimidin-5-yl)-p-nitrophenylalanine having a protected carboxyl group (Pg), compound 551, is then reacted with at least 2 stoichiometric equivalents of ammonia or an appropriate primary or secondary amine, for example, $HNR^8R^9$ (e.g., diethylamine —$R^8$ and $R^9$ are both ethyl, dimethylamine, aniline, piperidine and the like). The reaction can be conducted neat or in a suitable inert solvent such as tetrahydrofuran, chloroform, methylene chloride, and the like. The reaction is typically conducted at a temperature of from about 15 to about 30° C. for a period of time sufficient to effect substantial completion of the reaction which typically occurs in from about 0.2 to 12 hours to afford N-[2-($R^8R^9N$)-5-nitro-pyrimidin-5-yl)-p-nitrophenylalanine having a protected carboxyl group (PG), compound 552. This product can be recovered by conventional methods such as chromatography, filtration, evaporation, crystallization and the like or, alternatively, used in the next step without purification and/or isolation.

Compound 553 is prepared by selective reduction of the nitro group on the phenyl ring using techniques well known in the art. Exposure to hydrogen gas in the presence of palladium black in ethyl acetate affects the desired selective reduction. The resulting product, compound 553, can be recovered by conventional methods, such as chromatography, filtration, evaporation, crystallization, and the like or, alternatively, used in the next step without purification and/or isolation.

The crude isocyanate (compound 554) is prepared by dissolving compound 553 in an inert solvent such as dichloromethane, chloroform, and the like, and adding an aqueous $NaHCO_3$ solution to form a biphasic mixture that is cooled to about 10 to about –10° C. A solution phosgene in toluene is added followed by vigorous stirring at for about 10 minutes to about 2 hours at about 10 to about −10° C. The resulting product, compound 554, can be recovered by conventional methods, such as chromatography, filtration, evaporation, crystallization, and the like or, alternatively, used in the next step without purification and/or isolation.

The hydantoin derivative, compound 555, is prepared by coupling the isocyanate to an appropriate amino acid ester, compound 506, using well known coupling methods. For example, the coupling can be accomplished by reaction of compound 554 with at least an equivalent and preferably a slight excess of compound 506 in an inert solvent such as dichloromethane, or chloroform, THF, DMF, and the like. If the hydrochloride salt of the amine is used, then the reaction is run in the presence of a base such as triethylamine, or diisopropylethylamine and the like. The coupling and concurrent cyclization reaction typically proceeds at a temperature of from about 0° C. to about 37° C. for a period of from 1 to about 14 hours. The resulting product, compound 555, can be recovered by conventional methods, such as chromatography, filtration, evaporation, crystallization, and the like or, alternatively, used in the next step without purification and/or isolation.

In one embodiment, compound 556 is prepared by convetional hydrogenation of the 5-nitro group as described above to provide for a compound of this invention ($R^2$ is —$NRR^1$ where R and $R^1$ are both hydrogen).

In another embodiment, compound 556 is an intermediate wherein the amino group is further functionalized in the manner described in the general methods below to provide to provide for derivatives wherein R and $R^1$ are other than hydrogen.

Deprotection of compound 555 or a compound further derivatized therefrom can be achieved using conventional methods to afford the final product, compound 556 (or a derivative thereof), which can be recovered by conventional methods, such as chromatography, filtration, evaporation, crystallization, and the like.

Scheme II illustrates a synthetic approach to compounds of the present invention, which may be generalized to the elaboration of protected forms of a wide variety of aminoacids, and not just protected forms of 4'-nitrophenylalanine. Although Scheme II illustrates the elaboration of 4'-nitrophenylalanine (557) to give a protected form of a 4'-aminophenylalanine (560), a wide variety of methods may be employed to access analogs of 560, in which the phenyl group of the phenylalanine bears substituents in addition to the amino group, or in which the phenyl group is replaced by an aromatic heterocycle. As indicated elsewhere herein, the methods for preparation of such analogs of 560 include, but are not limited to, such well known methods of aminoacid synthesis as asymmetric hydrogenation, stereoselective alkylation of glycine derivatives or equivalents thereof, and arylations of organozinc compounds derived from 3-iodoalanine derivatives. The free amino group in compound 560, and the above described analogs of compound 560, is elaborated to generate a hydantoin ring present in compound 561, by methods identical to those illustrated in Scheme I, for elaboration of compound 553 into compound 555. Compound 561 may be selectively deprotected to give compound 562, which may be elaborated to give compound 563, by methods identical to those illustrated in Scheme I, for elaboration of compound 550 into compound 552.

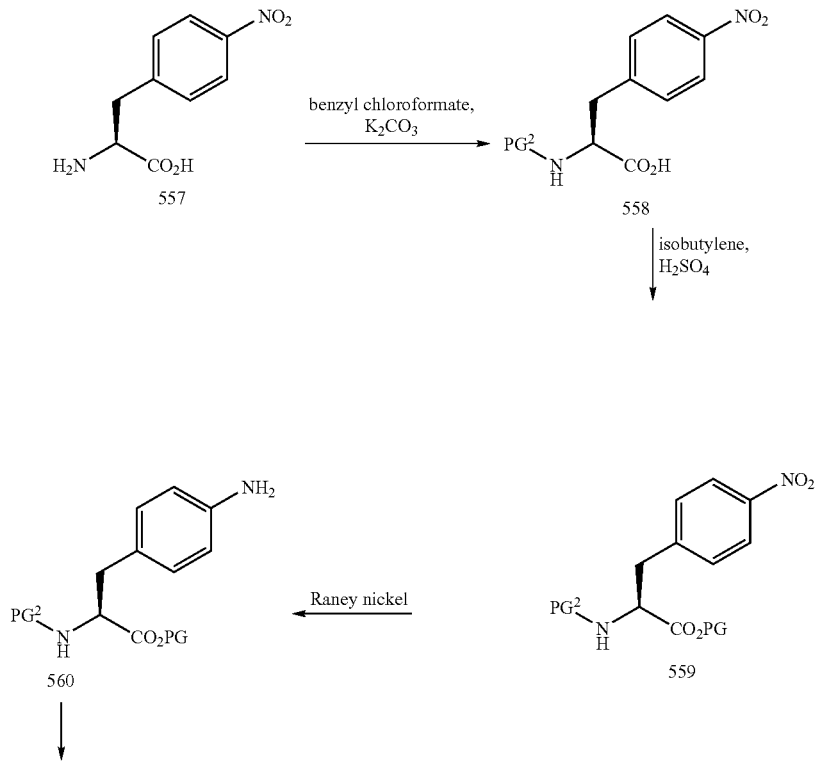

Scheme II

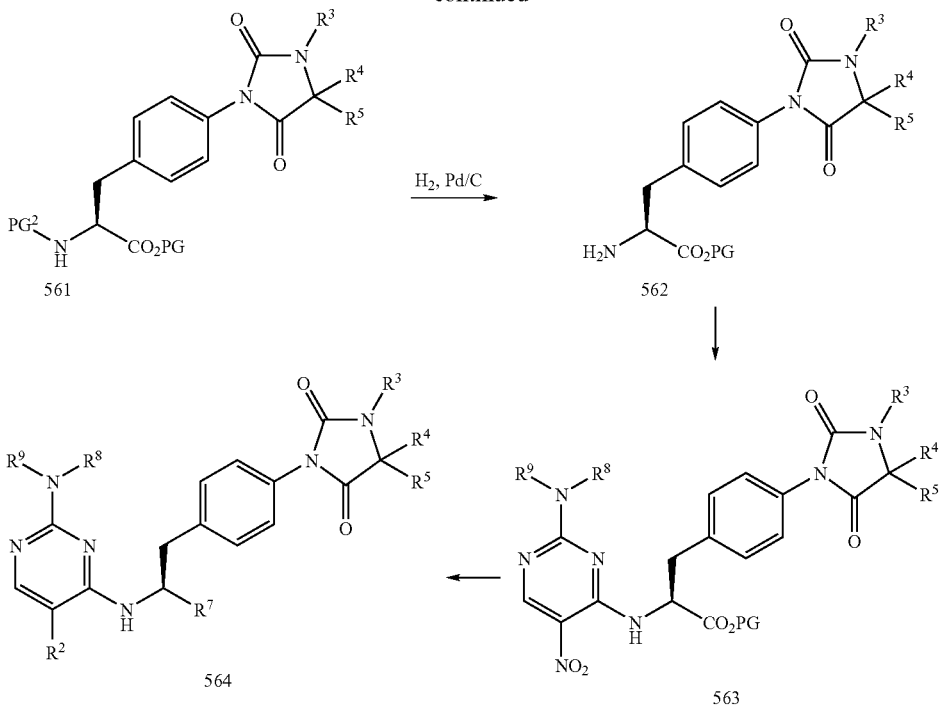

where $R^3$, $R^4$, $R^5$, $R^8$, $R^9$ and PG are as described above, and $PG^2$ is a protective group orthogonal to PG.

For example, protecting groups are added to the amino group and the carboxyl group using techniques well known in the art. The amino group of compound 557 can be protected, for example, by reaction with benzyl chloroformate in a solvent such as water in the presence of $K_2CO_3$ or other suitable base to scavenge the acid generated. Upon reaction completion, compound 558 can be recovered by conventional methods, such as chromatography, filtration, evaporation, neutralization, crystallization, and the like or, alternatively, used in the next step without purification and/or isolation.

The carboxylic acid group of compound 558 can then be protected by reaction with isobutylene in a solvent such as dichloromethane in the presence of sulfuric acid ($H_2SO_4$) to provide for compound 559. The resulting product, compound 559, can be recovered by conventional methods, such as chromatography, filtration, neutralization, evaporation, crystallization, and the like or, alternatively, used in the next step without purification.

As per above, PG and $PG^2$ are removed orthogonally to each other such that removal of one protecting group does not affect the other protecting group.

The protected nitrophenylalanine, compound 559, is reduced to the amine and carboxyl protected aminophenylalanine using Raney nickel in an inert solvent such as methanol or ethanol. The reaction is run at a temperature of from about 0° C. to about 37° C. for about 1 to about 48 hours, or until the reaction is complete. The resulting product, compound 560, can be recovered by conventional methods, such as chromatography, filtration, evaporation, crystallization, and the like or, alternatively, used in the next step without purification.

Conversion of the p-amino group of compound 560 to the corresponding hydantoin of compound 561 is accomplished using methods described hereinabove. Removal of the nitrogen protecting group ($PG^2$) proceeds according to conventional methods. For example, a benzyloxy carbonyl group on compound 561 is readily removed with hydrogen in the presence of palladium on carbon to provide for compound 562, which can be recovered by conventional methods, such as chromatography, filtration, evaporation, crystallization, and the like or, alternatively, used in the next step without purification and/or isolation.

Coupling of the carboxyl-protected p-hydantoin phenylalanine, compound 562, with compound 500 (shown in Scheme I), followed by reaction with an amine $HNR^8R^9$ (also shown in Scheme I) provides for compound 563 which is then further derivatized and then deprotected at the carboxyl group to provide for compounds of this invention, compound 564 as per the methods described above.

Though Scheme II is specific to phenylalanine derivatives, a wide variety of substituted aryl alanines, heteroaryl alanines, or substituted heteroaryl alanines, all of which are well known in the art, can also be employed in this reaction scheme. These compounds can be prepared using known methods in addition to those methods disclosed in several review articles. Preferably, the amino acid starting materials used herein are L-amino acids.

To prepare compounds where $R^2$ is a substituent other than an amino group or a substituted amino group, 2,4-dichloro-5-iodopyrimidine (commercially available) is used in place of compound 500 in Schemes I and II. These reaction sequences are modified to allow the analogues of compounds 552 and 563 (where the nitro group on the pyrimidine ring is an iodo group) to be reacted with arylboronic acids (many commercially available) or heteroarylboronic acids (many commercially available), using a palladium catalyst, to give N-[2-diethylamino-5-arylpyrimidin-4-yl]-4'-nitrophenyl-alanine t-butyl esters or N-[2-diethylamino-5-heteroarylpyrimidin-4-yl]-4'- nitrophenylalanine t-butyl esters. Alternatively these analogues can be reacted with alkyl zinc halides (many commercially available) or substituted alkyl zinc halides (many commercially available), using a palladium catalyst, to give N-[2-diethylamino-5-alkylpyrimidin-4-yl]-4'-nitrophenylalanine t-butyl esters or N-[2-diethylamino-5-(substituted)alkylpyrimidin-4-yl]-4'-nitrophenylalanine.

Additionally, starting materials having a non-amino $R^2$ group may be prepared as shown in Scheme III.

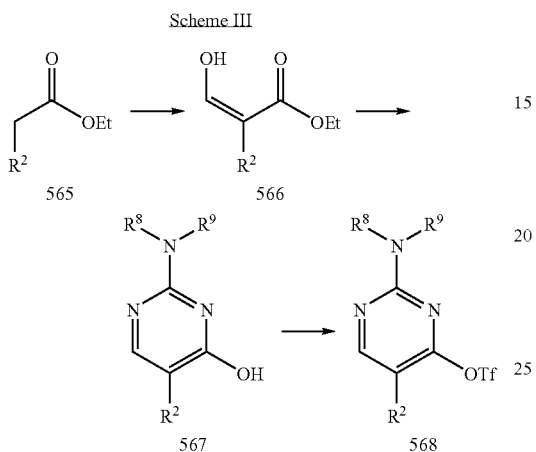

Scheme III

Ester 565 containing the desired $R^2$ group is used as the starting material. The ester may also contain a substituent such as a protected alcohol that can later be converted to the desired $R^2$ group. The ester 565 is reacted with excess ethyl formate in the presence of base such as KOtBu to give compound 566.

Ester 566 can be cyclized to form pyrimidine 567 upon exposure to an appropriate guanidine sulfate having the desired $R^8$ and $R^9$ groups under refluxing conditions.

Alcohol 567 is next converted to triflate 568 using standard conditions such as by exposure of 567 to diisoproplyamine, dimethlyaminopyridine, and trifluoroacetic anhydride in dichloromethane. Triflate 568 can then be coupled to compounds such as amino acids 550 and 562 to give intermediates that can be elaborated as described above to give compounds of the invention. Suitable coupling conditions include contacting triflate 568 with amino acids 550 or 562 in DMF (100° C.).

Finally for a general review of asymmetric synthesis of α-aminoacids, including arylalanines see:
1. The asymmetric synthesis of unnatural α-amino acids as building blocks for complex molecule synthesis. Natchus, Michael G.; Tian, Xinrong. Xemplar Biosciences, Atlanta, Ga., USA. Organic Synthesis: Theory and Applications (2001), 5 89–196.
2. Recent developments in the stereoselective synthesis of α-amino acids. Duthaler, Rudolf O. Cent. Res. Lab., CIBA, BASEL, Switz. Tetrahedron (1994), 50(6), 1539–650.

For a general review of asymmetric synthesis of α-aminoacids, including arylalanines, by asymmetric hydrogenationsee:
1. Asymmetric hydrogenation and other methods for the synthesis of unnatural amino acids and derivatives. Ager, David J. RCCorp, Raleigh, N.C., USA. Current Opinion in Drug Discovery & Development (2002), 5(6), 892–905.
2. Unnatural α-amino acids via asymmetric hydrogenation of enamides. Burk, Mark J.; Bienewald, Frank. Germany. Editor(s): Beller, Matthias; Bolm, Carsten. Transition Metals for Organic Synthesis (1998), 2 13–25.

For a general review of asymmetric synthesis of α-aminoacids, including arylalanines, by stereoselective alkylation of glycine derivatives see:
1. Enantioselective Amino Acid Synthesis by Chiral Phase-Transfer Catalysis. Maruoka, Keiji; Ooi, Takashi. Department of Chemistry Graduate School of Science, Kyoto University, Kyoto, Japan. Chemical Reviews (Washington, D.C., United States) (2003), 103(8), 3013–3028.
2. Glycine and alanine imines as templates for asymmetric synthesis of α-amino acids. Abellan, Tomas; Chinchilla, Rafael; Galindo, Nuria; Guillena, Gabriela; Najera, Carmen; Sansano, Jose M. Dpto. de Quimica Organica, Universidad de Alicante, Alicante, Spain. European Journal of Organic Chemistry (2000), (15), 2689–2697.
3. Stereoselective alkylation of chiral glycine and chiral α-aminopropionic acid derivatives in the preparation of enantiopure α- and β-amino acids. Juaristi, Eusebio; Balderas, Margarita; Leon-Romo, Jose Luis; Lopez-Ruiz, Heraclio; Reyes, Adelfo. Departamento de Quimica, Centro de Investigacion y de Estudios Avanzados del Instituto Politecnico Nacional, Mexico, Mex. Editor(s): Scolastico, Carlo; Nicotra, Francecso. Current Trends in Organic Synthesis, [Proceedings of the International Conference on Organic Synthesis], 12th, Venezia, Jun. 28–Jul. 2, 1998 (1999), Meeting Date 1998, 199–206. Publisher: Kluwer Academic/Plenum Publishers, New York, N.Y.

For a general review of asymmetric synthesis of α-aminoacids, including aryalalanines, by reaction of zinc reagents prepared from 3-iodoalanine derivatives see:
1. The development of zinc and zinc/copper reagents for the synthesis of enantiomerically pure amino acids., Gair, Susan; Jackson, Richard F. W. Current Organic Chemistry (1998), 2(5), 527–550.

Pharmaceutical Formulations

When employed as pharmaceuticals, the compounds of this invention are usually administered in the form of pharmaceutical compositions. These compounds can be administered by a variety of routes including oral, rectal, transdermal, subcutaneous, intravenous, intramuscular, and intranasal. These compounds are effective as both injectable and oral compositions. Such compositions are prepared in a manner well known in the pharmaceutical art and comprise at least one active compound.

This invention also includes pharmaceutical compositions which contain, as the active ingredient, one or more of the compounds of Formula I, Ia, Ib and Ic above associated with pharmaceutically acceptable carriers. In making the compositions of this invention, the active ingredient is usually mixed with an excipient, diluted by an excipient or enclosed within such a carrier which can be in the form of a capsule, sachet, paper or other container. The excipient employed is typically an excipient suitable for administration to human subjects or other mammals. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, for example, up to 10% by weight of the active compound, soft and hard gelatin capsules, suppositories, sterile injectable solutions, and sterile packaged powders.

In preparing a formulation, it may be necessary to mill the active compound to provide the appropriate particle size prior to combining with the other ingredients. If the active compound is substantially insoluble, it ordinarily is milled to a particle size of less than 200 mesh. If the active compound is substantially water soluble, the particle size is normally adjusted by milling to provide a substantially uniform distribution in the formulation, e.g. about 40 mesh.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup, and methyl cellulose. The formulations can additionally include: lubricating agents such as talc, magnesium stearate, and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

The compositions are preferably formulated in a unit dosage form, each dosage containing from about 5 to about 100 mg, more usually about 10 to about 30 mg, of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The active compound is effective over a wide dosage range and is generally administered in a pharmaceutically effective amount. It, will be understood, however, that the amount of the compound actually administered will be determined by a physician, in the light of the relevant circumstances, including the condition to be treated, the chosen route of administration, the actual compound administered, the age, weight, and response of the individual patient, the severity of the patient's symptoms, and the like.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation is then subdivided into unit dosage forms of the type described above containing from, for example, 0.1 to about 500 mg of the active ingredient of the present invention.

The tablets or pills of the present invention may be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate.

The liquid forms in which the novel compositions of the present invention may be incorporated for administration orally or by injection include aqueous solutions suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. Preferably the compositions are administered by the oral or nasal respiratory route for local or systemic effect. Compositions in preferably pharmaceutically acceptable solvents may be nebulized by use of inert gases. Nebulized solutions may be breathed directly from the nebulizing device or the nebulizing device may be attached to a face masks tent, or intermittent positive pressure breathing machine. Solution, suspension, or powder compositions may be administered, preferably orally or nasally, from devices which deliver the formulation in an appropriate manner.

The following formulation examples illustrate the pharmaceutical compositions of the present invention.

FORMULATION EXAMPLE 1

Hard gelatin capsules containing the following ingredients are prepared:

| Ingredient | Quantity (mg/capsule) |
|---|---|
| Active Ingredient | 30.0 |
| Starch | 305.0 |
| Magnesium stearate | 5.0 |

The above ingredients are mixed and filled into hard gelatin capsules in 340 mg quantities.

FORMULATION EXAMPLE 2

A tablet formula is prepared using the ingredients below:

| Ingredient | Quantity (mg/tablet) |
|---|---|
| Active Ingredient | 25.0 |
| Cellulose, microcrystalline | 200.0 |
| Colloidal silicon dioxide | 10.0 |
| Stearic acid | 5.0 |

The components are blended and compressed to form tablets, each weighing 240 mg.

FORMULATION EXAMPLE 3

A dry powder inhaler formulation is prepared containing the following components:

| Ingredient | Weight % |
|---|---|
| Lactose | 5 |
| Active Ingredient | 95 |

The active mixture is mixed with the lactose and the mixture is added to a dry powder inhaling appliance.

FORMULATION EXAMPLE 4

Tablets, each containing 30 mg of active ingredient, are prepared as follows:

| Ingredient | Quantity (mg/tablet) |
|---|---|
| Active Ingredient | 30.0 mg |
| Starch | 45.0 mg |
| Microcrystalline cellulose | 35.0 mg |
| Polyvinylpyrrolidone (as 10% solution in water) | 4.0 mg |
| Sodium carboxymethyl starch | 4.5 mg |
| Magnesium stearate | 0.5 mg |
| Talc | 1.0 mg |
| Total | 120 mg |

The active ingredient, starch and cellulose are passed through a No. 20 mesh U.S. sieve and mixed thoroughly. The solution of polyvinyl-pyrrolidone is mixed with the resultant powders, which are then passed through a 16 mesh U.S. sieve. The granules so produced are dried at 50° to 60° C. and passed through a 16 mesh U.S. sieve. The sodium carboxymethyl starch, magnesium stearate, and talc, previously passed through a No. 30 mesh U.S. sieve, are then added to the granules which, after mixing, are compressed on a tablet machine to yield tablets each weighing 120 mg.

FORMULATION EXAMPLE 5

Capsules, each containing 40 mg of medicament are made as follows:

| Ingredient | Quantity (mg/capsule) |
|---|---|
| Active Ingredient | 40.0 mg |
| Starch | 109.0 mg |
| Magnesium stearate | 1.0 mg |
| Total | 150.0 mg |

The active ingredient, cellulose, starch, an magnesium stearate are blended, passed through a No. 20 mesh U.S. sieve, and filled into hard gelatin capsules in 150 mg quantities.

FORMULATION EXAMPLE 6

Suppositories, each containing 25 mg of active ingredient are made as follows:

| Ingredient | Amount |
|---|---|
| Active Ingredient | 25 mg |
| Saturated fatty acid glycerides to | 2,000 mg |

The active ingredient is passed through a No. 60 mesh U.S. sieve and suspended in the saturated fatty acid glycerides previously melted using the minimum heat necessary. The mixture is then poured into a suppository mold of nominal 2.0 g capacity and allowed to cool.

FORMULATION EXAMPLE 7

Suspensions, each containing 50 mg of medicament per 5.0 mL dose are made as follows:

| Ingredient | Amount |
|---|---|
| Active Ingredient | 50.0 mg |
| Xanthan gum | 4.0 mg |
| Sodium carboxymethyl cellulose (11%) Microcrystalline cellulose (89%) | 50.0 mg |
| Sucrose | 1.75 g |
| Sodium benzoate | 10.0 mg |
| Flavor and Color | q.v. |
| Purified water to | 5.0 mL |

The medicament, sucrose and xanthan gum are blended, passed through a No. 10 mesh U.S. sieve, and then mixed with a previously made solution of the microcrystalline cellulose and sodium carboxymethyl cellulose in water. The sodium benzoate, flavor, and color are diluted with some of the water and added with stirring. Sufficient water is then added to produce the required volume.

FORMULATION EXAMPLE 8

| Ingredient | Quantity (mg/capsule) |
|---|---|
| Active Ingredient | 15.0 mg |
| Starch | 407.0 mg |
| Magnesium stearate | 3.0 mg |
| Total | 425.0 mg |

The active ingredient, cellulose, starch, and magnesium stearate are blended, passed through a No. 20 mesh U.S. sieve, and filled into hard gelatin capsules in 425 mg quantities.

FORMULATION EXAMPLE 9

An intravenous formulation may be prepared as follows:

| Ingredient | Quantity |
|---|---|
| Active Ingredient | 250.0 mg |
| Isotonic saline | 1000 mL |

FORMULATION EXAMPLE 10

A topical formulation may be prepared as follows:

| Ingredient | Quantity |
|---|---|
| Active Ingredient | 1–10 g |
| Emulsifying Wax | 30 g |

-continued

| Ingredient | Quantity |
| --- | --- |
| Liquid Paraffin | 20 g |
| White Soft Paraffin | to 100 g |

The white soft paraffin is heated until molten. The liquid paraffin and emulsifying wax are incorporated and stirred until dissolved. The active ingredient is added and stirring is continued until dispersed. The mixture is then cooled until solid.

Another preferred formulation employed in the methods of the present invention employs transdermal delivery devices ("patches"). Such transdermal patches may be used to provide continuous or discontinuous infusion of the compounds of the present invention in controlled amounts. The construction and use of transdermal patches for the delivery of pharmaceutical agents is well known in the art. See, e.g., U.S. Pat. No. 5,023,252, issued Jun. 11, 1991, herein incorporated by reference. Such patches may be constructed for continuous, pulsatile, or on demand delivery of pharmaceutical agents.

Direct or indirect placement techniques may be used when it is desirable or necessary to introduce the pharmaceutical composition to the brain. Direct techniques usually involve placement of a drug delivery catheter into the host's ventricular system to bypass the blood-brain barrier. One such implantable delivery system used for the transport of biological factors to specific anatomical regions of the body is described in U.S. Pat. No. 5,011,472 which is herein incorporated by reference.

Indirect techniques, which are generally preferred, usually involve formulating the compositions to provide for drug latentiation by the conversion of hydrophilic drugs into lipid-soluble drugs. Latentiation is generally achieved through blocking of the hydroxy, carbonyl, sulfate, and primary amine groups present on the drug to render the drug more lipid soluble and amenable to transportation across the blood-brain barrier. Alternatively, the delivery of hydrophilic drugs may be enhanced by intraarterial infusion of hypertonic solutions which can transiently open the blood-brain barrier.

Utility

The compounds of this invention can be employed to bind VLA-4 ($\alpha_4\beta_1$ integrin) in biological samples, i.e., the compounds bind VLA-4 with an $IC_{50}$ of 15 μM or less in a competitive binding assay as described herein. Accordingly, these compounds have utility in, for example, assaying such samples for VLA-4. In such assays, the compounds can be bound to a solid support and the VLA-4 sample added thereto. The amount of VLA-4 in the sample can be determined by conventional methods such as use of a sandwich ELISA assay. Alternatively, labeled VLA-4 can be used in a competitive assay to measure for the presence of VLA-4 in the sample. Other suitable assays are well known in the art.

In addition, the compounds of this invention inhibit, in vivo, adhesion of leukocytes to endothelial cells mediated by VLA-4 by competitive binding to VLA-4. Accordingly, the compounds of this invention can be used in the treatment of diseases mediated by VLA-4 or leucocyte adhesion. Such diseases include inflammatory diseases in mammalian patients such as asthma, Alzheimer's disease, atherosclerosis, AIDS dementia, diabetes (including acute juvenile onset diabetes), inflammatory bowel disease (including ulcerative colitis and Crohn's disease), multiple sclerosis, rheumatoid arthritis, tissue transplantation, tumor metastasis, meningitis, encephalitis, stroke, and other cerebral traumas, nephritis, retinitis, atopic dermatitis, psoriasis, myocardial ischemia and acute leukocyte-mediated lung injury such as that which occurs in adult respiratory distress syndrome.

The biological activity of the compounds identified above may be assayed in a variety of systems. For example, a compound can be immobilized on a solid surface and adhesion of cells expressing VLA-4 can be measured. Using such formats, large numbers of compounds can be screened. Cells suitable for this assay include any leukocytes known to express VLA-4 such as T cells, B cells, monocytes, eosinophils, and basophils. A number of leukocyte cell lines can also be used, examples include Jurkat and U937.

The test compounds can also be tested for the ability to competitively inhibit binding between VLA-4 and VCAM-1, or between VLA-4 and a labeled compound known to bind VLA-4 such as a compound of this invention or antibodies to VLA-4. In these assays, the VCAM-1 can be immobilized on a solid surface. VCAM-1 may also be expressed as a recombinant fusion protein having an Ig tail (e.g., IgG) so that binding to VLA-4 may be detected in an immunoassay. Alternatively, VCAM-1 expressing cells, such as activated endothelial cells or VCAM-1 transfected fibroblasts can be used. For assays to measure the ability to block adhesion to brain endothelial cells, the assays described in International Patent Application Publication No. WO 91/05038 are particularly preferred. This application is incorporated herein by reference in its entirety.

Many assay formats employ labeled assay components. The labeling systems can be in a variety of forms. The label may be coupled directly or indirectly to the desired component of the assay according to methods well known in the art. A wide variety of labels may be used. The component may be labeled by any one of several methods. The most common method of detection is the use of autoradiography with $^3H$, $^{125}I$, $^{35}S$, $^{14}C$, or $^{32}P$ labeled compounds or the like. Non-radioactive labels include ligands which bind to labeled antibodies, fluorophores, chemiluminescent agents, enzymes and antibodies which can serve as specific binding pair members for a labeled ligand. The choice of label depends on sensitivity required, ease of conjugation with the compound, stability requirements, and available instrumentation.

Appropriate in vivo models for demonstrating efficacy in treating inflammatory responses include EAE (experimental autoimmune encephalomyelitis) in mice, rats, guinea pigs or primates, as well as other inflammatory models dependent upon α4 integrins.

Compounds having the desired biological activity may be modified as necessary to provide desired properties such as improved pharmacological properties (e.g., in vivo stability, bio-availability), or the ability to be detected in diagnostic applications. Stability can be assayed in a variety of ways such as by measuring the half-life of the proteins during incubation with peptidases or human plasma or serum. A number of such protein stability assays have been described (see, e.g., Verhoef et al., Eur. J. Drug Metab. Pharmacokinet., 1990, 15(2):83–93).

For diagnostic purposes, a wide variety of labels may be linked to the compounds, which may provide, directly or indirectly, a detectable signal. Thus, the compounds of the subject invention may be modified in a variety of ways for a variety of end purposes while still retaining biological activity. In addition, various reactive sites may be introduced at the terminus for linking to particles, solid substrates, macromolecules, or the like.

Labeled compounds can be used in a variety of in vivo or in vitro applications. A wide variety of labels may be employed, such as radionuclides (e.g., gamma-emitting radioisotopes such as technetium-99 or indium-111), fluorescers (e.g., fluorescein), enzymes, enzyme substrates, enzyme cofactors, enzyme inhibitors, chemiluminescent compounds, bioluminescent compounds, and the like. Those of ordinary skill in the art will know of other suitable labels for binding to the complexes, or will be able to ascertain such using routine experimentation. The binding of these labels is achieved using standard techniques common to those of ordinary skill in the art.

In vitro uses include diagnostic applications such as monitoring inflammatory responses by detecting the presence of leukocytes expressing VLA-4. The compounds of this invention can also be used for isolating or labeling such cells. In addition, as mentioned above, the compounds of the invention can be used to assay for potential inhibitors of VLA-4/VCAM-1 interactions.

For in vivo diagnostic imaging to identify, e.g., sites of inflammation, radioisotopes are typically used in accordance with well known techniques. The radioisotopes may be bound to the peptide either directly or indirectly using intermediate functional groups. For instance, chelating agents such as diethylenetriaminepentacetic acid (DTPA) and ethylenediaminetetraacetic acid (EDTA) and similar molecules have been used to bind proteins to metallic ion radioisotopes.

The complexes can also be labeled with a paramagnetic isotope for purposes of in vivo diagnosis, as in magnetic resonance imaging (MRI) or electron spin resonance (ESR), both of which are well known. In general, any conventional method for visualizing diagnostic imaging can be used. Usually gamma- and positron-emitting radioisotopes are used for camera imaging and paramagnetic isotopes are used for MRI. Thus, the compounds can be used to monitor the course of amelioration of an inflammatory response in an individual. By measuring the increase or decrease in lymphocytes expressing VLA-4 it is possible to determine whether a particular therapeutic regimen aimed at ameliorating the disease is effective.

The pharmaceutical compositions of the present invention can be used to block or inhibit cellular adhesion associated with a number of diseases and disorders. For instance, a number of inflammatory disorders are associated with integrins or leukocytes. Treatable disorders include, e.g., transplantation rejection (e.g., allograft rejection), Alzheimer's disease, atherosclerosis, AIDS dementia, diabetes (including acute juvenile onset diabetes), retinitis, cancer metastases, rheumatoid arthritis, acute leukocyte-mediated lung injury (e.g., adult respiratory distress syndrome), asthma, nephritis, and acute and chronic inflammation, including atopic dermatitis, psoriasis, myocardial ischemia, and inflammatory bowel disease (including Crohn's disease and ulcerative colitis). In preferred embodiments the pharmaceutical compositions are used to treat inflammatory brain disorders, such as multiple sclerosis (MS), viral meningitis and encephalitis.

Inflammatory bowel disease is a collective term for two similar diseases referred to as Crohn's disease and ulcerative colitis. Crohn's disease is an idiopathic, chronic ulceroconstrictive inflammatory disease characterized by sharply delimited and typically transmural involvement of all layers of the bowel wall by a granulomatous inflammatory reaction. Any segment of the gastrointestinal tract, from the mouth to the anus, may be involved, although the disease most commonly affects the terminal ileum and/or colon.

Ulcerative colitis is an inflammatory response limited largely to the colonic mucosa and submucosa. Lymphocytes and macrophages are numerous in lesions of inflammatory bowel disease and may contribute to inflammatory injury.

Asthma is a disease characterized by increased responsiveness of the tracheobronchial tree to various stimuli potentiating paroxysmal constriction of the bronchial airways. The stimuli cause release of various mediators of inflammation from IgE-coated mast cells including histamine, eosinophilic and neutrophilic chemotactic factors, leukotrines, prostaglandin and platelet activating factor. Release of these factors recruits basophils, eosinophils and neutrophils, which cause inflammatory injury.

Atherosclerosis is a disease of arteries (e.g., coronary, carotid, aorta and iliac). The basic lesion, the atheroma, consists of a raised focal plaque within the intima, having a core of lipid and a covering fibrous cap. Atheromas compromise arterial blood flow and weaken affected arteries. Myocardial and cerebral infarcts are a major consequence of this disease. Macrophages and leukocytes are recruited to atheromas and contribute to inflammatory injury.

Rheumatoid arthritis is a chronic, relapsing inflammatory disease that primarily causes impairment and destruction of joints. Rheumatoid arthritis usually first affects the small joints of the hands and feet but then may involve the wrists, elbows, ankles and knees. The arthritis results from interaction of synovial cells with leukocytes that infiltrate from the circulation into the synovial lining of the joints. See e.g., Paul, *Immunology* (3d ed., Raven Press, 1993).

Another indication for the compounds of this invention is in treatment of organ or graft rejection mediated by VLA-4. Over recent years there has been a considerable improvement in the efficiency of surgical techniques for transplanting tissues and organs such as skin, kidney, liver, heart, lung, pancreas and bone marrow. Perhaps the principal outstanding problem is the lack of satisfactory agents for inducing immunotolerance in the recipient to the transplanted allograft or organ. When allogeneic cells or organs are transplanted into a host (i.e., the donor and donee are different individuals from the same species), the host immune system is likely to mount an immune response to foreign antigens in the transplant (host-versus-graft disease) leading to destruction of the transplanted tissue. $CD8^+$ cells, CD4 cells and monocytes are all involved in the rejection of transplant tissues. Compounds of this invention which bind to alpha-4 integrin are useful, inter alia, to block alloantigen-induced immune responses in the donee thereby preventing such cells from participating in the destruction of the transplanted tissue or organ. See, e.g., Paul et al., *Transplant International* 9, 420–425 (1996); Georczynski et al., *Immunology* 87, 573–580 (1996); Georcyznski et al., *Transplant. Immunol.* 3, 55–61 (1995); Yang et al., *Transplantation* 60, 71–76 (1995); Anderson et al., *APMIS* 102, 23–27 (1994).

A related use for compounds of this invention which bind to VLA-4 is in modulating the immune response involved in "graft versus host" disease (GVHD). See e.g., Schlegel et al., *J. Immunol.* 155, 3856–3865 (1995). GVHD is a potentially fatal disease that occurs when immunologically competent cells are transferred to an allogeneic recipient. In this situation, the donor's immunocompetent cells may attack tissues in the recipient. Tissues of the skin, gut epithelia and liver are frequent targets and may be destroyed during the course of GVHD. The disease presents an especially severe problem when immune tissue is being transplanted, such as in bone marrow transplantation; but less severe GVHD has also been reported in other cases as well, including heart and liver transplants. The therapeutic agents of the present invention are used, inter alia, to block activation of the donor T-cells thereby interfering with their ability to lyse target cells in the host.

A further use of the compounds of this invention is inhibiting tumor metastasis. Several tumor cells have been reported to express VLA-4 and compounds which bind VLA-4 block adhesion of such cells to endothelial cells. Steinback et al., *Urol. Res.* 23, 175–83 (1995); Orosz et al., *Int. J. Cancer* 60, 867–71 (1995); Freedman et al., *Leuk. Lymphoma* 13, 47–52 (1994); Okahara et al., *Cancer Res.* 54, 3233–6 (1994).

A further use of the compounds of this invention is in treating multiple sclerosis. Multiple sclerosis is a progressive neurological autoimmune disease that affects an estimated 250,000 to 350,000 people in the United States. Multiple sclerosis is thought to be the result of a specific autoimmune reaction in which certain leukocytes attack and initiate the destruction of myelin, the insulating sheath covering nerve fibers. In an animal model for multiple sclerosis, murine monoclonal antibodies directed against VLA-4 have been shown to block the adhesion of leukocytes to the endothelium, and thus prevent inflammation of the central nervous system and subsequent paralysis in the animals[16].

Pharmaceutical compositions of the invention are suitable for use in a variety of drug delivery systems. Suitable formulations for use in the present invention are found in *Remington's Pharmaceutical Sciences*, Mace Publishing Company, Philadelphia, Pa., 17th ed. (1985).

In order to enhance serum half-life, the compounds may be encapsulated, introduced into the lumen of liposomes, prepared as a colloid, or other conventional techniques may be employed which provide an extended serum half-life of the compounds. A variety of methods are available for preparing liposomes, as described in, e.g., Szoka, et al., U.S. Pat. Nos. 4,235,871, 4,501,728 and 4,837,028 each of which is incorporated herein by reference.

The amount administered to the patient will vary depending upon what is being administered, the purpose of the administration, such as prophylaxis or therapy, the state of the patient, the manner of administration, and the like. In therapeutic applications, compositions are administered to a patient already suffering from a disease in an amount sufficient to cure or at least partially arrest the symptoms of the disease and its complications. An amount adequate to accomplish this is defined as "therapeutically effective dose." Amounts effective for this use will depend on the disease condition being treated as well as by the judgment of the attending clinician depending upon factors such as the severity of the inflammation, the age, weight and general condition of the patient, and the like.

The compositions administered to a patient are in the form of pharmaceutical compositions described above. These compositions may be sterilized by conventional sterilization techniques, or may be sterile filtered. The resulting aqueous solutions may be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers, or stabilizers will result in the formation of pharmaceutical salts.

The therapeutic dosage of the compounds of the present invention will vary according to, for example, the particular use for which the treatment is made, the manner of administration of the compound, the health and condition of the patient, and the judgment of the prescribing physician. For example, for intravenous administration, the dose will typically be in the range of about 20 µg to about 500 µg per kilogram body weight, preferably about 100 µg to about 300 µg per kilogram body weight. Suitable dosage ranges for intranasal administration are generally about 0.1 pg to 1 mg per kilogram body weight. Effective doses can be extrapolated from dose-response curves derived from in vitro or animal model test systems.

Compounds of this invention are also capable of binding or antagonizing the actions of $\alpha_6\beta_1$, $\alpha_9\beta_1$, $\alpha_4\beta_7$, $\alpha_d\beta_2$, $\alpha_e\beta_7$ integrins (although $\alpha_4\beta_1$ and $\alpha_9\beta_1$ are preferred in this invention). Accordingly, compounds of this invention are also useful for preventing or reversing the symptoms, disorders or diseases induced by the binding of these integrins to their respective ligands.

For example, International Publication Number WO 98/53817, published Dec. 3, 1998 (the disclosure of which is incorporated herein by reference in its entirety) and references cited therein describe disorders mediated by $\alpha_4\beta_7$. This reference also describes an assay for determining antagonism of $\alpha_4\beta_7$ dependent binding to VCAM-Ig fusion protein.

Additionally, compounds that bind $\alpha_d\beta_2$ and $\alpha_e\beta_7$ integrins are particularly useful for the treatment of asthma and related lung diseases. See, for example, M. H. Grayson et al., *J. Exp. Med.* 1998, 188(11) 2187–2191. Compounds that bind $\alpha_e\beta_7$ integrin are also useful for the treatment of systemic lupus erythematosus (see, for example, M. Pang et al., *Arthritis Rheum.* 1998, 41(8), 1456–1463); Crohn's disease, ulcerative colitis and infammatory bowel disease (IBD) (see, for example, D. Elewaut et al., *Scand J. Gastroenterol* 1998, 33(7) 743–748); Sjogren's syndrome (see, for example, U. Kroneld et al., *Scand J. Gastroenterol* 1998, 27(3), 215–218); and rheumatoid arthritis (see, for example, *Scand J. Gastroenterol* 1996, 44(3), 293–298). And compounds that bind $\alpha_6\beta_1$ may be useful in preventing fertilization (see, for example, H. Chen et al., *Chem. Biol.* 1999, 6, 1–10).

Certain of the compounds within the generic formulas described herein are also useful as synthetic intermediates for other compounds of this invention as illustrated in the examples herein.

The following synthetic and biological examples are offered to illustrate this invention and are not to be construed in any way as limiting the scope of this invention. Unless otherwise stated, all temperatures are in degrees Celsius.

EXAMPLES

In the examples below, the following abbreviations have the following meanings. If an abbreviation is not defined, it has its generally accepted meaning.

| | |
|---|---|
| Å = | angstroms |
| atm = | atmosphere |
| brd = | broad doublet |
| brm = | broad multiplet |
| brs or bs = | broad singlet |
| brt = | broad triplet |
| Bu = | butyl |

| | |
|---|---|
| CBZ = | carboxylbenzyl |
| CH₂Cl₂ = | dichloromethane |
| d = | doublet |
| DIPEA = | diisopropylethylamine |
| DMSO = | dimethylsulfoxide |
| DMAP = | 4-N,N-dimethylaminopyridine |
| DME = | ethylene glycol dimethyl ether |
| DMF = | dimethylformamide |
| Et = | ethyl |
| Et₃N = | triethylamine |
| EtOAc = | ethyl acetate |
| EtOH = | ethanol |
| eq or eq. = | equivalent |
| g = | grams |
| h = | hour |
| HCl = | hydrochloric acid |
| HPLC = | high performance liquid chromatography |
| hr or h = | hour |
| Hz = | hertz |
| kg = | kilogram |
| K₂CO₃ = | potassium carbonate |
| KCN = | Potassium cyanide |
| KHSO₄ = | Potassium hydrogen sulfate |
| L = | liter |
| LC = | Liquid Chromatography |
| m = | multiplet |
| M = | Molar |
| Me = | methyl |
| mm = | millimeter |
| MS = | Mass Spectrometer |
| MeOH = | methanol |
| MHz = | megahertz |
| mg = | milligram |
| MgSO₄ = | magnesium sulfate |
| mL = | milliliter |
| min = | minutes |
| mM = | millimolar |
| mmol = | millimol |
| nM = | nanomolar |
| N = | normal |
| NMR = | Nuclear magnetic resonance |
| psi = | pounds per square inch |
| PtO₂ = | platinum oxide |
| PBS = | Phosphate buffer saline |
| q = | quartet |
| q.s. = | means adding a quantity sufficient to achieve a certain state |
| rt or RT = | room temperature |
| s = | singlet |
| t = | triplet |
| t-BuOH = | tert-butanol |
| TFA = | trifluoroacetic acid |
| THF = | tetrahydrofuran |
| TLC or tlc = | thin layer chromatography |
| v/v = | Volume to volume ratio |
| w/v = | Weight to volume ratio |
| VCAM = | Vascular cell adhesion molecule |
| μL = | microliter |
| μg = | microgram |
| μm = | microns |
| μM = | micromolar |

Unless otherwise indicated, the starting materials used in the preparation of the following exemplary compounds were commercially available.

Procedure for Preparing Intermediates Useful in the Synthesis of Compounds of the Present Invention Step 1

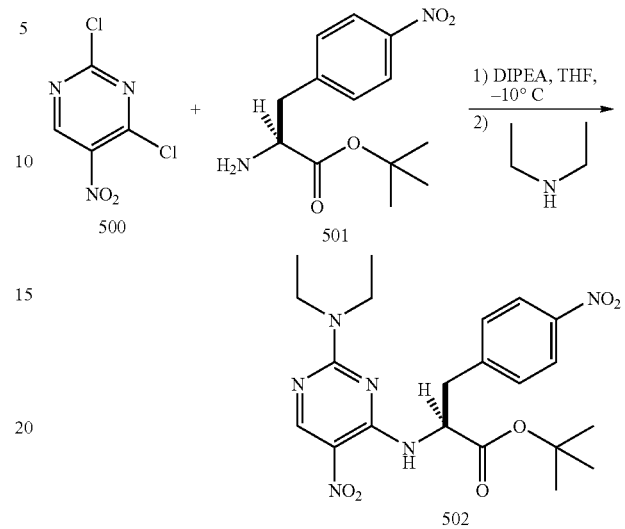

To a cold solution of dichloropyrimidine (3.51 g, 0.018 mol) (500) and isopropyl-ethylamine (DIPEA) (3 mL) in 30 mL of THF was added a solution of the aminoester (501) (4.84 g, 0.018 mol in THF (15 mL) via cannula. After complete addition the mixture was stirred at 0° C. for about 30 min and then quenched with diethylamine (3 mL). After 18 h at room temperature, the THF was evaporated, the residue taken up in 100 mL of 0.5 N HCl and the mixture extracted with CH₂Cl₂ (3×50 mL). The combined organic layers were washed with NaHCO₃ and water and dried over Na₂SO₄. After evaporation of the solvent the residue was subjected to column chromatography on silica (ISCO system, hexane/EtOAc solvent gradient). There was obtained 5.9 g of product (502) (70%).

$H^1$-NMR (300 MHz, CDCl₃): δ 1.24 (6H, m), 1.40 (9H, s), 3.11 (2H, m), 3.51–3.72 (4H, m), 5.00 (1H, q, J=6 Hz), 7.35 (2H, d, J=9 Hz), 8.13 (2H, d, J=9 Hz), 8.73 (1H, brd), 8.97 (1H, s);

$C^{13}$-NMR (75 MHz, CDCl₃): 12.78, 13.22, 27.8, 37.6, 37.6, 42.6, 42.8, 54.7, 82.9, 120.0, 123.6, 130.1, 143.9, 147.0, 154.8, 157.6, 157.6, 159.9, 169.2;

LC/MS: 4.071 min;

M=261 (M+H).

Step 2

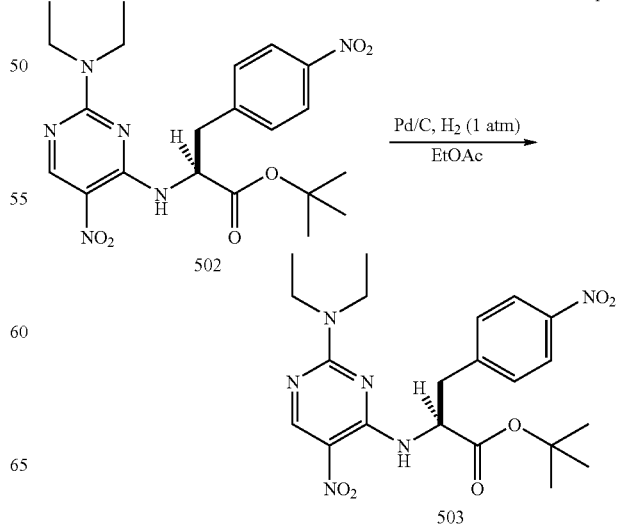

To a solution of 10.75 g of dinitro compound (502) (0.023 mol) in EtOAc (200 mL) was added 0.81 g of Palladium black. The flask was connected to the house vacuum for 15 min and the mixture stirred magnetically. Then the mixture was exposed to one atmosphere of hydrogen via balloon. After 4 h the mixture was filtered over Celite and the filtrate evaporated. There was obtained 9.87 g (98%) of crude product (503). The crude product (503) was used without further purification.

H$^1$-NMR (300 MHz, CDCl$_3$): δ 1.24 (6H, m), 1.40 (9H, s), 3.11 (2H, t, J=6 Hz), 3.51–3.70 (4H, m), 4.80 (1H, q, J=6 Hz), 6.60 (2H, d, J=9 Hz), 6.97 (2H, d, J=9 Hz), 8.64 (1H, brd), 8.97 (1H, s);

C$^{13}$-NMR (75 MHZ, CDCl$_3$): 12.86, 13.40, 27.95, 37.01, 42.53, 42.85, 82.04, 115.30, 120.10, 125.66, 130.18, 145.39, 154.94, 157.65, 160.05, 170.31;

LC/MS: 2.704 min;

M=231 (M+H).

Step 3

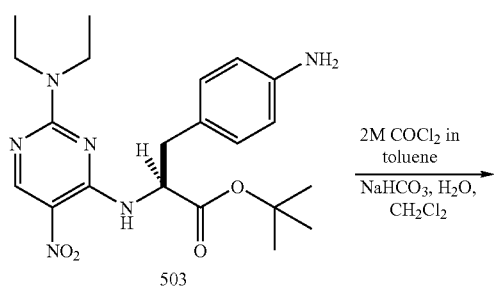

To a solution of 5.91 g (0.0137 mol) of the aniline compound (503) in CH$_2$Cl$_2$ (100 mL) was added 120 mL of aqueous NaHCO$_3$ solution. The biphasic mixture was cooled to 0° C. and 18 mL of a 2 M phosgene solution in toluene (0.036 mol) was added in a single portion to the CH$_2$Cl$_2$ layer. The resulting mixture was vigorously stirred for 45 min at ice bath temperature and the layers were separated. The organic layer was dried over Na$_2$SO$_4$ and the solvent evaporated. The crude isocyanate (504) was used without further purification. (Alternatively, the dried organic layer can be used directly for the next reaction).

Step 4

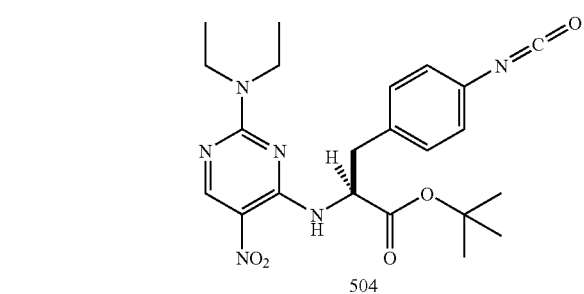

To a solution of the aminoester hydrochloride salt (506) in CH$_2$Cl$_2$ was added Et$_3$N (2 eq) and the resulting mixture was added to a solution of the crude isocyanate (504) in CH$_2$Cl$_2$. After stirring at room temperature for 2 h, the mixture was dilluted with 1.2 M HCl and the layers separated. The organic layer was washed with water and dried over Na$_2$SO$_4$. After evaporation of the solvent, the residue was taken up in EtOH and Et$_3$N (2 eq) was added again. The mixture was heated to reflux for 2–4 h (TLC analysis). After evaporation of the solvent, the desired product was usually crystallized from the crude residue through layer crystallization (usually EtOAc, hexane). Alternatively, the crude product was subjected to column chromatography on silica (ISCO system, hexane/EtOAc solvent gradient).

The following General Methods are used to convert the intermediate prepared above to the final compounds of the present invention.

General Method A

Conversion of a 5-nitropyrimidine to a 5-aminopyrimidine

A suspension of the 5-nitropyrimidine, and one tenth an equal mass of 10% Pd/C, in ethanol solvent, was shaken under 60 psi hydrogen gas for 72 h. At this time, TLC of an evaporated aliquot of the reaction mixture indicated complete conversion of the 5-nitropyrimidine. The Pd/C catalyst was removed by filtering the reaction mixture through Celite, and the 5-aminopyrimidine was isolated by evaporation of the ethanol solvent. The crude product was used in subsequent chemical steps without purification.

General Method B

Conversion of a 5-aminopyrimidine to a 5-(N-isopropyl)aminopyrimidine

A suspension of the 5-aminopyrimidine, and one twenty-fifth an equal mass of PtO$_2$, and 1.1 equivalents acetone, in ethanol solvent, was shaken under 60 psi hydrogen gas for 24 h. At this time, TLC of an evaporated aliquot of the reaction mixture indicated complete conversion of the 5-aminopyrimidine. The Pt catalyst was removed by filtering the reaction mixture through Celite, and the 5-(N-isopropyl)aminopyrimidine was isolated by evaporation of the ethanol solvent. The crude product was used in subsequent chemical steps without purification.

General Method C

Conversion of a 5-(N-isopropyl)aminopyrimidine to a 5-(N-isopropyl-N-methanesulfonyl)aminopyrimidine A solution of the 5-(N-isopropyl)aminopyrimidine, and 5.0 equivalents anhydrous pyridine, in anhydrous $CH_2Cl_2$ solvent, maintained at 0° C., was treated with 3.0 equivalents methanesulfonyl chloride. After 2 h, an aliquot of the reaction mixture was worked-up by partition between 1 M $KHSO_4$ and $CH_2Cl_2$. TLC of the aliquot $CH_2Cl_2$ layer indicated complete conversion of the 5-(N-isopropyl)aminopyrimidine. The reaction mixture was added to three times an equal volume of 1 M $KHSO_4$, and the resulting mixture was extracted three times with $CH_2Cl_2$. The combined $CH_2Cl_2$ extracts were washed with saturated aqueous NaCl, dried with $MgSO_4$, filtered, and evaporated to afford the 5-(N-isopropyl-N-methanesulfonyl)aminopyrimidine. The crude product was purified by flash chromotography on silica gel using EtOAc/hexanes, or by recrystallization.

General Method D

Conversion of a 5-(N-isopropyl)aminopyrimidine to a 5-(N-isopropyl-N-acetyl)aminopyrimidine A solution of the 5-(N-isopropyl)aminopyrimidine, and 5.0 equivalents $Et_3N$, and 0.1 equivalents DMAP, in anhydrous $CH_2Cl_2$ solvent, was treated with 3.0 equivalents acetyl chloride. After 24 h, an aliquot of the reaction mixture was worked-up by partition between 1 M $KHSO_4$ and $CH_2Cl_2$. TLC of the aliquot $CH_2Cl_2$ layer indicated complete conversion of the 5-(N-isopropyl)aminopyrimidine. The reaction mixture was added to three times an equal volume of 1 M $KHSO_4$, and the resulting mixture was extracted three times with $CH_2Cl_2$. The combined $CH_2Cl_2$ extracts were washed with saturated aqueous NaCl, dried with $MgSO_4$, filtered, and evaporated to afford the 5-(N-isopropyl-N-acetyl)aminopyrimidine. The crude product was purified by flash chromotography on silica gel using EtOAc/hexanes, or by recrystallization.

General Method E

Conversion of a 5-(N-isopropyl)aminopyrimidine to a 5-(N-isopropyl-N-trifluoroacetyl)aminopyrimidine A solution of the 5-(N-isopropyl)aminopyrimidine, and 5.0 equivalents $Et_3N$, in anhydrous $CH_2Cl_2$ solvent, was treated with 3.0 equivalents trifluoroacetic anhydride. After 24 h, an aliquot of the reaction mixture was worked-up by partition between 1 M $KHSO_4$ and $CH_2Cl_2$. TLC of the aliquot $CH_2Cl_2$ layer indicated complete conversion of the 5-(N-isopropyl)-aminopyrimidine. The reaction mixture was added to three times an equal volume of 1 M $KHSO_4$, and the resulting mixture was extracted three times with $CH_2Cl_2$. The combined $CH_2Cl_2$ extracts were washed with saturated aqueous NaCl, dried with $MgSO_4$, filtered, and evaporated to afford the 5-(N-isopropyl-N-trifluoroacetyl)aminopyrimidine. The crude product was purified by flash chromatography on silica gel using EtOAc/hexanes, or by recrystallization.

General Method F

Conversion of a 5-aminopyrimidine to a 5-(N-(4-fluorobenzene)sulfonyl)aminopyrimidine A solution of the 5-aminopyrimidine, in anhydrous pyridine solvent, maintained at 0° C., was treated with 1.0 equivalents 4-fluorobenzenesulfonyl chloride. After 2 h, an aliquot of the reaction mixture was worked-up by partition between 1 M $KHSO_4$ and EtOAc. TLC of the aliquot EtOAc layer indicated complete conversion of the 5-aminopyrimidine. The reaction mixture was added in portions to sufficient 1 M $KHSO_4$ to neutralize all the pyridine solvent, and the resulting mixture was extracted three times with EtOAc. The combined EtOAc extracts were washed with saturated aqueous NaCl, dried with $MgSO_4$, filtered, and evaporated to afford the 5-(N-(4-fluorobenzene)sulfonyl)aminopyrimidine. The crude product was used in subsequent chemical steps without purification.

General Method G

Conversion of a 5-(N-(4-fluorobenzene)sulfonyl)aminopyrimidine to a 5-(N-methyl-N-(4-fluorobenzene)sulfonyl)aminopyrimidine A suspension of the 5-(N-(4-fluorobenzene)sulfonyl)aminopyrimidine, and 5.0 equivalents of $K_2CO_3$, in anhydrous DMF solvent, was treated with 2.0 equivalents MeI and the mixture was stirred for 48 h. At this time, an aliquot of the reaction mixture was worked-up by partition between 1 M $KHSO_4$ and EtOAc. TLC of the aliquot EtOAc layer indicated complete conversion of the 5-(N-(4-fluorobenzene)sulfonyl)amino-pyrimidine. The majority of the DMF solvent was removed from the reaction mixture by rotary evaporation under high vacuum, and the residue was treated with sufficient 1 M $KHSO_4$ to neutralize all the $K_2CO_3$. The resulting mixture was extracted three times with EtOAc, and the combined EtOAc extracts were washed with saturated aqueous NaCl, treated with $MgSO_4$, filtered, and evaporated to afford the 5-(N-methyl-N-(4-fluorobenzene)sulfonyl)aminopyrimidine. The crude product was purified by flash chromotography on silica gel using EtOAc/hexanes, or by recrystallization.

General Method H

Conversion of a 5-aminopyrimidine to a 5-(N-trifluoroacetyl)aminopyrimidine

A solution of the 5-aminopyrimidine, and 3.0 equivalents $Et_3N$, in anhydrous $CH_2Cl_2$ solvent, maintained at 0° C., was treated with 1.5 equivalents trifluoroacetic anhydride. After 2 h at 0° C. and 24 h at room temperature, an aliquot of the reaction mixture was worked-up by partition between 1 M KHSO$_4$ and CH$_2$Cl$_2$. TLC of the aliquot CH$_2$Cl$_2$ layer indicated complete conversion of the 5-aminopyrimidine. The reaction mixture was added to three times an equal volume of 1 M KHSO$_4$, and the resulting mixture was extracted three times with CH$_2$Cl$_2$. The combined CH$_2$Cl$_2$ extracts were washed with saturated aqueous NaCl, dried with MgSO$_4$, filtered, and evaporated to afford the 5-(N-trifluoroacetyl)aminopyrimidine. The crude product was used in subsequent chemical steps without purification.

General Method I

Conversion of a 5-(N-trifluoroacetyl)aminopyrimidine to a 5-(N-ethyl-N-trifluoroacetyl)aminopyrimidine A suspension of the 5-(N-trifluoroacetyl)aminopyrimidine, and 5.0 equivalents K$_2$CO$_3$, in anhydrous DMF solvent, was treated with 2.0 equivalents EtI and the mixture was stirred for 48 h. At this time, an aliquot of the reaction mixture was worked-up by partition between 1 M KHSO$_4$ and EtOAc. TLC of the aliquot EtOAc layer indicated complete conversion of the 5-(N-trifluoroacetyl)aminopyrimidine. The majority of the DMF solvent was removed from the reaction mixture by rotary evaporation under high vacuum, and the residue was treated with sufficient 1 M KHSO$_4$ to neutralize all the K$_2$CO$_3$. The resulting mixture was extracted three times with EtOAc, and the combined EtOAc extracts were washed with saturated aqueous NaCl, treated with MgSO$_4$, filtered, and evaporated to afford the 5-(N-ethyl-N-trifluoro-acetyl)aminopyrimidine. The crude product was purified by flash chromatography on silica gel using EtOAc/hexanes, or by recrystallization.

General Method J

Conversion of a 5-(N-ethyl-N-trifluoroacetyl)aminopyrimidine to a 5-(N-ethyl)aminopyrimidine A solution of 5-(N-ethyl-N-trifluoroacetyl)aminopyrimidine, in 4:1 v/v MeOH/H$_2$O, was treated with 5.0 equivalents K$_2$CO$_3$, and the mixture was stirred for 4 h. At that time, an aliquot of the reaction mixture was partitioned between 1 M KHSO$_4$ and EtOAc, and TLC of the aliquot EtOAc layer indicated complete conversion of the 5-(N-ethyl-N-trifluoroacetyl-aminopyrimidine. The reaction mixture was then rotary evaporated, and the residue treated with sufficient 1 M KHSO$_4$ to neutralize all the K$_2$CO$_3$, and the mixture extracted three times with EtOAc. The combined EtOAc extracts were treated with MgSO$_4$, filtered, and evaporated to afford the 5-(N-ethyl)amino-pyrimidine. The crude product was used in subsequent chemical steps without purification.

General Method K

Conversion of a 5-(N-ethyl)aminopyrimidine to a 5-(N-ethyl-N-acyl)aminopyrimidine A solution of the 5-(N-ethyl)aminopyrimidine, and 5.0 equivalents Et$_3$N, and 0.1 equivalents DMAP, in anhydrous CH$_2$Cl$_2$ solvent, was treated with 3.0 equivalents acyl chloride. After 24 h, an aliquot of the reaction mixture was worked-up by partition between 1 M KHSO$_4$ and CH$_2$Cl$_2$. TLC of the aliquot CH$_2$Cl$_2$ layer indicated complete conversion of the 5-(N-ethyl)-aminopyrimidine. The reaction mixture was added to three times an equal volume of 1 M KHSO$_4$, and the resulting mixture was extracted three times with CH$_2$Cl$_2$. The combined CH$_2$Cl$_2$ extracts were washed with saturated aqueous NaCl, dried with MgSO$_4$, filtered, and evaporated to afford the 5-(N-ethyl-N-acyl)aminopyrimidine. The crude product was purified by flash chromatography on silica gel using EtOAc/hexanes, or by recrystallization.

General Method L

Conversion of a 5-(N-ethyl)aminopyrimidine to a 5-(N,N-diethyl)aminopyrimidine

A suspension of the 5-aminopyrimidine, and one twenty-fifth an equal mass of PtO$_2$, and 5 equivalents equivalents of aqueous acetaldehyde, in ethanol solvent, was shaken under 60 psi hydrogen gas for 24 h. At this time, TLC of an evaporated aliquot of the reaction mixture indicated complete conversion of the 5-(N-ethyl)aminopyrimidine. The Pt catalyst was removed by filtering the reaction mixture through Celite, and the 5-(N,N-diethyl)aminopyrimidine was isolated by evaporation of the ethanol solvent. The crude product was purified by flash chromatography on silica using EtOAc/hexanes.

General Method M

Conversion of a Pyrimidine-carboxylic t-butyl Ester to a Pyrimidine-carboxylic Acid The carboxylic t-butyl ester was dissolved in one hundred times an equal volume of 96% formic acid, and the solution was heated to 70° C. for 2 h. At this time, TLC of an evaporated aliquot of the reaction mixture indicated complete conversion of the pyrimidine-carboxylic t-butyl ester. The formic acid was removed by rotary evaporation under high vacuum to afford the pyrimidine-carboxylic acid as a formate salt. Typically, the obtained product was >98% pure, but if necessary, the product was purified by preparative reverse-phase HPLC, or by flash chromatography on silica gel using EtOAc/hexanes, or by recrystallization.

The following compounds were prepared by the methods described above using appropriate commercially available starting materials

Example 1

Preparation of (S)-2-{5-[N-(4-fluorophenylsulfonyl)-N-methyl-amino]-2-(N',N'-diethylamino)-pyrimidin-4-ylamino}-3-[4-(3,4,4-trimethyl-2,5-dioxoimidazolidin-1-yl)phenyl]propanoic acid (1)

CCN(CC)c1ncc(N(C)S(=O)(=O)c2ccc(F)cc2)c(NC(Cc3ccc(cc3)N4C(=O)N(C)C(C)(C)C4=O)C(=O)O)n1

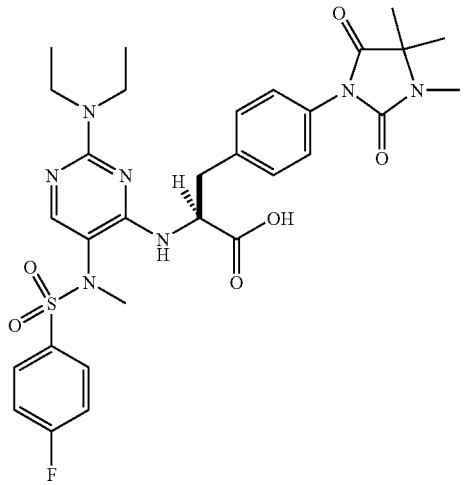

Example 1 was prepared by Steps 1, 2, 3, and 4 (using N-methyl 2-aminoisobutyric acid methyl ester hydrobromide, which was prepared according to Breitenmoser, et al., Helv. Chim. Acta, (2002), 85(3), 885–912), and then Methods A, F, G, and M.

$H^1$-NMR (300 MHz, $CDCl_3$): δ 1.17 (6H, brm), 1.48 (6H, s), 2.94 (3H, s), 2.96–3.51 (6H, m), 4.89 (1H, m), 7.22 (8H, m), 7.78 (1H, brs), 8.19 (1H, brs);

$C^{13}$-NMR (75 MHz, $CDCl_3$): 12.51, 22.11, 24.53, 39.1, 43.2, 57.1, 60.95, 66.4, 112.6, 116.71, 117.0, 125.8, 127.9, 128.3, 129.9, 130.1, 130.5, 130.7, 136.4, 142.5, 158.1, 165.0, 175.4;

LC/MS: 2.710 min;
M=642 (M+H).

Example 2

Preparation of (S)-2-{5-[N-(4-fluorophenylsulfonyl)-N-methyl-amino]-2-(N',N'-diethylamino)-pyrimidin-4-ylamino}-3-[4-(1,3-dioxo-(S)-tetrahydro-2H-pyrrolo[1,2-e]imidazol-2-yl)phenyl]propanoic acid (2)

CCN(CC)c1ncc(N(C)S(=O)(=O)c2ccc(F)cc2)c(NC(Cc3ccc(cc3)N4C(=O)C5CCCN5C4=O)C(=O)O)n1

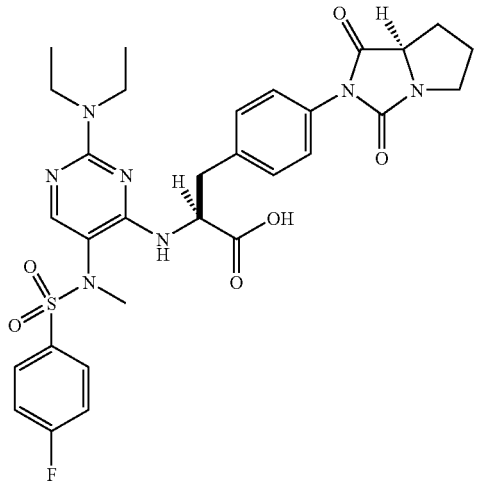

Example 2 was prepared by Steps 1, 2, 3, and 4 (using D-proline methyl ester hydrochloride), and then Methods A, F, G, and M.

$H^1$-NMR (300 MHz, CDCl$_3$): δ 1.24 (6H, m), 1.84 (1H, m), 2.16 (2H, m), 2.27 (1H, m), 2.92 and 3.02 (3H, 2 s), 3.22–3.77 (8H, m), 4.20 (1H, m), 4.88 (1H, brs), 7.21 (8H, m), 7.75 (2H, m), 8.18 (2H, m);

$C^{13}$-NMR (75 MHz, CDCl$_3$): 12.51, 26.7, 27.51, 29.53, 36.1, 45.53, 56.2, 63.1, 112.6, 116.7, 117.0, 125.65, 129.9, 130.5, 130.8, 142.15, 159.1, 165.0, 172.4;

LC/MS: 2.639 min;
M=640 (M+H).

Example 3

Preparation of (S)-2-{5-[N-(4-fluorophenylsulfonyl)-N-methyl-amino]-2-(N',N'-diethylamino)-pyrimidin-4-ylamino}-3-[4-(3-methyl-2,5-dioxoimidazolidin-1-yl)phenyl]propanoic acid (3)

CCN(CC)c1ncc(N(C)S(=O)(=O)c2ccc(F)cc2)c(NC(Cc3ccc(cc3)N4C(=O)CN(C)C4=O)C(=O)O)n1

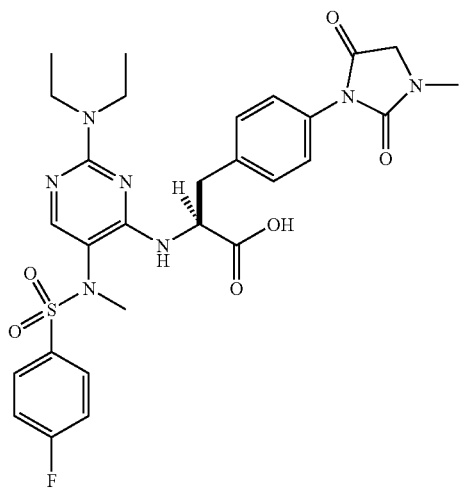

Example 3 was prepared by Steps 1, 2, 3, and 4 (using sarcosine methyl ester hydrochloride), and then Methods A, F, G, and M.

$H^1$-NMR (300 MHz, CDCl$_3$): δ 1.24 (6H, m), 2.61–3.22 (8H, m), 3.50 (4H, $$ m), 3.97 (2H, m), 4.84 (1H, m), 7.22 (8H, m), 7.76 (1H, brs), 7.87 (1H, brs);

$C^{13}$-NMR (75 MHz, CDCl$_3$): 12.60, 29.6, 35.3, 36.2, 39.1, 50.5, 51.4, 112.3, 116.95, 125.8, 129.9, 130.4, 130.7, 136.8, 143.5, 152.1, 155.6, 156.2, 158.8, 163.9, 165.0, 168.6, 172.7;

LC/MS: 2.582 min;
M=614 (M+H).

Example 4

Preparation of (S)-2-{5-[N-acetyl-N-isopropyl-amino]-2-(N',N'-diethylamino)-pyrimidin-4-ylamino}-3-[4-(1,3-dioxo-(S)-tetrahydro-2H-pyrrolo[1,2-e]imidazol-2-yl)phenyl]propanoic acid (4)

CCN(CC)c1ncc(N(C(C)C)C(=O)C)c(NC(Cc2ccc(cc2)N3C(=O)C4CCCN4C3=O)C(=O)O)n1

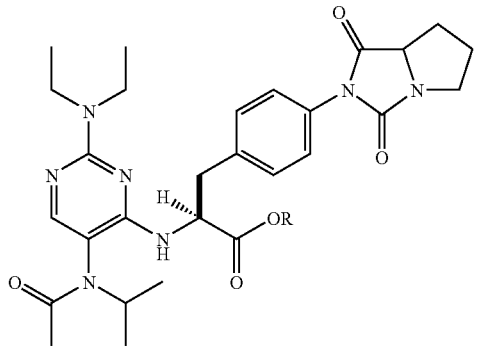

R = tert-Bu or H

Example 4 was prepared by Steps 1, 2, 3, and 4 (using L-proline methyl ester hydrochloride), and then Methods A, B, D, and M.

R=tert-Bu: H$^1$-NMR (300 MHz, CDCl$_3$): δ 1.07–1.37 (21H, m), 1.88 (1H, m), 2.01–2.14 (5H, m), 3.12–3.30 (5H, m), 3.53–3.6 (6H, m), 3.71–3.79 (2H, m), 4.19 (1H, t, J=9 Hz), 4.77–4.82 (2H, m), 5.6 (1H, brd, J=6 Hz), 7.31 (4H, m), 7.57 (1H, s);

C$^{13}$-NMR (75 MHz, CDCl$_3$): 13.2, 14.1, 19.1, 19.6, 21.0, 21.3, 22.6, 23.1, 26.8, 27.6, 37.0, 37.5, 41.7, 45.6, 46.7, 54.6, 55.1, 60.3, 63.1, 81.8, 82.0, 108.1, 108.2, 125.8, 125.9, 129.6, 130.0, 130.5, 130.6, 136.8, 137.2, 155.5, 158.7, 159.1, 159.1, 159.6, 171.0, 171.4, 172.3, 172.4;

LC/MS: 2.131 min;

M=608 (M+H).

R=H: H$^1$-NMR Spectra for the acid are extremely broadened out in CDCl$_3$. LC/MS: two ratamers 1.42 min and 1.49 min, M=551.6 (M+H).

Example 5

Preparation of (S)-2-{5-[N-acetyl-N-isopropyl-amino]-2-(N',N'-diethylamino)-pyrimidin-4-ylamino}-3-[4-(1,3-dioxo-(R)-tetrahydro-2H-pyrrolo[1,2-e]imidazol-2-yl)phenyl]propanoic acid (5)

CCN(CC)c1ncc(N(C(C)C)C(=O)C)c(NC(Cc2ccc(cc2)N3C(=O)C4CCCN4C3=O)C(=O)O)n1

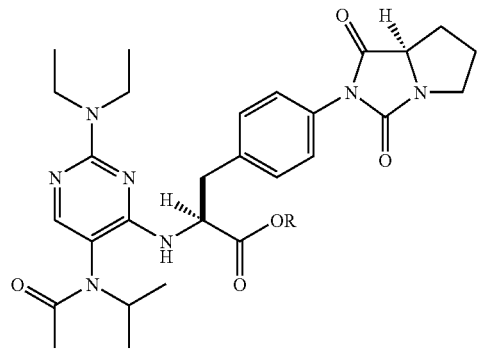

Example 5 was prepared by Steps 1, 2, 3, and 4 (using D-proline methyl ester hydrochloride), and then Methods A, B, D, and M.

H$^1$-NMR (300 MHz, MeOD): δ 0.67 and 0.93 (3H, d, J=6 Hz), 1.10 (3H, m), 1.15 (6H, m), 1.69 1H, brs), 1.93 (3H, s), 2.2 (3H, m), 3.3 (3H, m), 3.51 (6H, m), 4.3 (1H, brt, J=6 Hz), 4.70 (1H, m), 7.4 (4H, m), 7.68 (1H, s);

C$^{13}$-NMR (75 MHz, MeOD): 11.5, 17.5, 19.9, 20.0, 26.5, 26.9, 34.9, 35.3, 55.2, 63.2, 110.4, 126.3, 129.1, 129.3, 130.8, 137.5, 141.4, 141.7, 150.8, 159.6, 161.2, 171.8, 172.2, 174.4, 173.2;

LC/MS: two ratamers 1.42 min and 1.49 min; M=551.6 (M+H).

Example 6

Preparation of (S)-2-{5-[N-(methylsulfonyl)-N-iso-propyl-amino]-2-(N',N'-diethylamino)-pyrimidin-4-ylamino}-3-[4-(1,3-dioxo-(S)-tetrahydro-2H-pyrrolo[1,2-e]imidazol-2-yl)phenyl]propanoic acid (6)

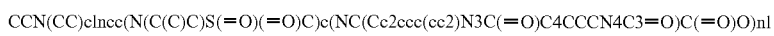

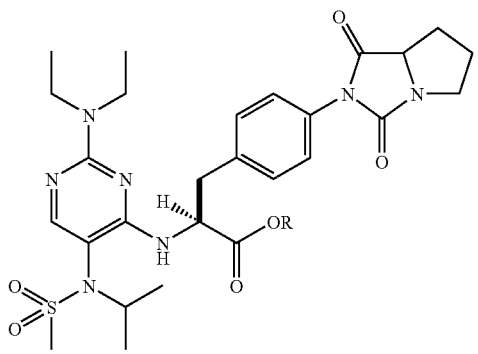

Example 6 was prepared by Steps 1, 2, 3, and 4 (using L-proline methyl ester hydrochloride), and then Methods A, B, C, and M.

$H^1$-NMR (300 MHz, $CDCl_3$): δ 1.22 (6H, m), 1.31 (6H, m), 1.95 (2H, m), 2.15 (2H, m), 2.41 (2H, m), 3.21 and 3.37 (3H, s), 3.57–3.82 (6H, m), 4.13 (1, brt, J=6 Hz), 4.41 (1H, m), 4.82 (1H, m), 7.36 (4H, m), 7.87 (1H, s).

LC/MS: 1.73 min, M=588.2 (M+H);

R=tert-Bu: $H^1$-NMR (300 MHz, $CDCl_3$): δ 0.93 (2H, t, J=6 Hz), 0.97 (2H, t, J=6 Hz), 1.16 (6H, m), 1.43 (9H, s), 1.68 and 1.87 (3H, s), 2.76 (3H, s), 2.98 (1H, m), 3.13 (2H, m), 3.56 (4H, m), 3.82 (1H, m), 5.21 (1H, m), 7.30 (4H, m), 7.61 (1H, s);

$C^{13}$-NMR (75 MHz, $CDCl_3$): 9.9, 12.9, 13.2, 14.10, 20.9, 21.9, 22.3, 24.9, 27.9, 37.0, 37.4, 41.8, 42.2, 44.3, 54.4, 55.0, 60.3, 81.7, 82.0, 111.3, 125.8, 125.9, 129.6, 129.6, 130.8, 130.9, 136.5, 136.9, 154.8, 154.9, 154.9, 157.6, 157.7, 159.6, 171.0, 171.2, 172.1, 172.2, 172.2, 172.3;

LC/MS: 2.17 min;

M=594.3 (M+H).

Example 7

Preparation of (S)-2-{5-[N-acetyl-N-ethyl-amino]-2-(N',N'-diethylamino)-pyrimidin-4-ylamino}-3-[4-(4-methyl-4,6-diaza-spiro[2.4]heptane-5,7-dione-6-yl)phenyl]propanoic acid (7)

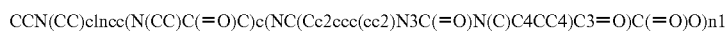

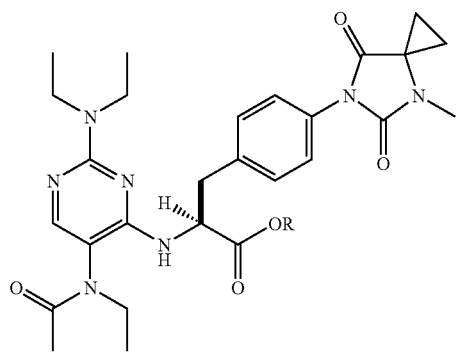

R = tert-Bu or H

Example 7 was prepared by Steps 1, 2, 3, and 4 (using 1-methylaminocyclopropane-1-carboxylic acid methyl ester hydrochloride which was prepared according to Vaidyanathan, et al., *J. Org. Chem.*, (1989), 54(8), 1815–1820), and then Methods A, H, I, J, K (using acetyl chloride), and M.

H¹-NMR Spectra for the acid are extremely broadened out in CDCl₃. LC/MS: two ratamers 1.529 min, M=538.2 (M+H);

R=tert-Bu: H¹-NMR (300 MHz, CDCl₃): δ 0.97–1.21 (11H, m), 1.4 (9H, s), 1.73–2.04 (8H, m), 2.98 (s, 3H), 3.15 (2H, m), 3.57 (4H, m), 3.92 (1H, m), 4.10 (1H, t, J=6 Hz), 4.82 (1H, m), 7.30 (4H, m), 7.65 (1H, m);

C¹³-NMR (75 MHz, CDCl₃): 13.0, 13.1, 13.2, 14.1, 21.0, 21.1, 22.0, 22.3, 24.2, 24.5, 27.9, 31.1, 37.2, 37.5, 41.9, 42.3, 42.5, 54.5, 54.9, 60.3, 61.7, 81.9, 82.1, 111.4, 126.1, 129.5, 130.6, 130.7, 136.3, 136.6, 154.3, 157.6, 159.5, 171.0, 171.1, 172.1, 172.2, 174.5;

LC/MS: 2.58 min;
M=636.3 (M+H).

Example 8

Preparation of (S)-2-{5-[N-acetyl-N-ethyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid (8)

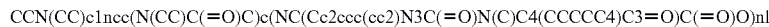

CCN(CC)c1ncc(N(CC)C(=O)C)c(NC(Cc2ccc(cc2)N3C(=O)N(C)C4(CCCCC4)C3=O)C(=O)O)n1

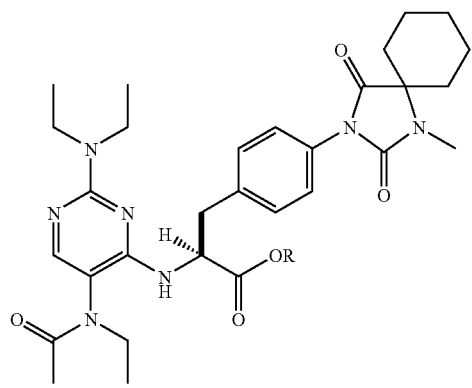

R = tert-Bu or H

1-Methylaminocyclohexane-1-carboxylic acid methyl ester hydrochloride was prepared by the well-known Strecker aminoacid synthesis, followed by esterification in methanolic HCl. Specifically, cyclohexanone was reacted with KCN and methylamine hydrochloride in the presence of Al₂O₃ suspended in acetonitrile under sonication, to give 1-methylaminocyclohexane-1-carbonitrile, which was isolated by evaporation and extraction. 1-methyl-aminocyclohexane-1-carbonitrile was dissolved in 6 M aqueous HCl, and heated to reflux for 24 h, to give 1-methylaminocyclohexane-1-carboxylic acid, upon neutralization and crystallization. 1-methylaminocyclohexane-1-carboxylic acid was dissolved in anhydrous methanol saturated with gaseous HCl, and heated to reflux for 6 h, followed by evaporation to give 1-methyl-aminocyclohexane-1-carboxylic acid methyl ester hydrochloride.

Example 8 was prepared by Steps 1, 2, 3, and 4 (using 1-methylaminocyclohexane-1-carboxylic acid methyl ester hydrochloride), and then Methods A, H, I, J, K (using acetyl chloride), and M.

H¹-NMR Spectra for the acid are extremely broadened out in CDCl₃;

LC/MS: 2.71 min;
M=580.3 (M+H).

Example 9

Preparation of (S)-2-{5-[N-(methylsulfonyl)-N-isopropyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid (9)

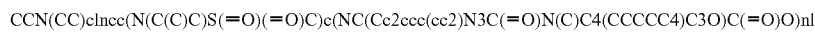

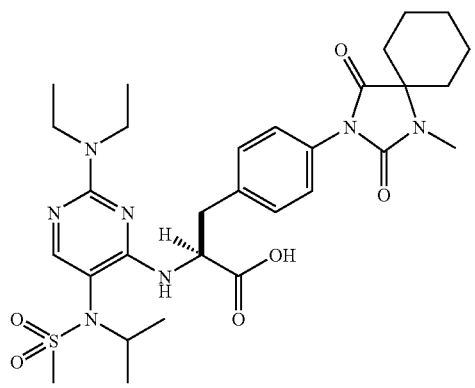

Example 9 was prepared by Steps 1, 2, 3, and 4 (using 1-methylaminocyclohexane-1-carboxylic acid methyl ester hydrochloride, as prepared in Example 8), and then Methods A, B, C, and M.

$H^1$-NMR (300 MHz, CDCl$_3$): δ 0.83 and 1.08 (6H, d, J=6 Hz), 1.23 (8H, brm), 1.78–2.10 (8H, m), 2.84 and 2.90 (3H, s), 3.23–3.56 (6H, m), 4.29 (1H, m), 4.82 (1H, m), 7.29 (4H, m), 8.17 and 8.21 (1H, s), 8.29 (1H, s).

$C^{13}$-NMR (75 MHz, CDCl$_3$): 12.7, 12.8, 21.2, 21.4, 21.6, 24.2, 24.5, 31.1, 39.8, 40.0, 52.4, 61.8, 106.3, 106.6, 126.1, 126.3, 129.9, 130.3, 130.5, 136.5, 136.7, 146.0, 152.2, 152.4, 154.5, 160.6, 161.6, 165.3, 174.0, 174.6;

LC/MS: 2.22 min;
M=630.3 (M+H).
R=tert-Bu: LC/MS: 2.38 min, M=644.2 (M+H).

Example 10

Preparation of (S)-2-{5-[N-(methylsulfonyl)-N-isopropyl-amino]-2-(N',N'-diethylamino)-pyrimidin-4-ylamino}-3-[4-(4-methyl-4,6-diaza-spiro[2.4]heptane-5,7-dione-6-yl)phenyl]propanoic acid (10)

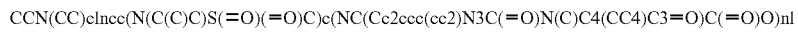

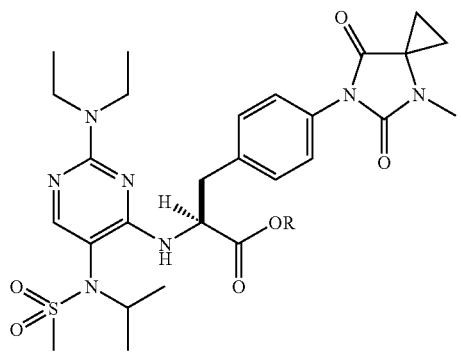

R = tert-Bu or H

Example 10 was prepared by Steps 1, 2, 3, and 4 (using 1-methylaminocyclopropane-1-carboxylic acid methyl ester hydrochloride), and then Methods A, B, C, and M.

LC/MS: 1.74 min, M=588.3 (M+H).

R=tert-Bu: $H^1$-NMR (300 MHz, CDCl$_3$) δ 0.87–1.50 (25H, m), 2.83, (3H, s), 3.04–3.33 (2H, m), 3.58–3.70 (4H, m), 4.86 (1H, m), 5.21 (1H, m), 7.39 (4H, m), 7.63 and 7.65 (1H, s);

C$^{13}$-NMR (75 MHz, CDCl$_3$): 9.9, 13.2, 25.0, 27.8, 37.5, 37.9, 41.9, 44.4, 51.3, 51.6, 54.5, 55.1, 60.4, 82.3, 82.5, 126.0, 129.7, 129.9, 130.9, 136.2, 155.0, 156.5, 158.7, 160.0, 172.3;

LC/MS: 2.62 min;

M=662.3 (M+H).

Example 11

Preparation of (S)-2-{5-[N-trifluoroacetyl-N-isopropyl-amino]-2-(N',N'-diethylamino)-pyrimidin-4-ylamino}-3-[4-(4-methyl-4,6-diaza-spiro[2.4]heptane-5,7-dione-6-yl)phenyl]propanoic acid (11)

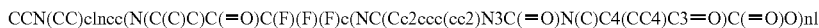

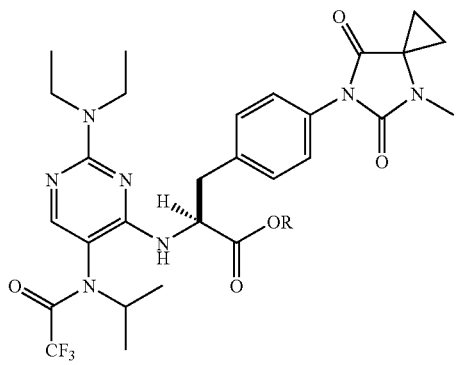

R = tert-Bu or H

Example 11 was prepared by Steps 1, 2, 3, and 4 (using 1-methylaminocyclopropane-1-carboxylic acid methyl ester hydrochloride), and then Methods A, B, E, and M.

LC/MS: 1.90 min, M=606.2 (M+H).

R=tert-Bu: H$^1$-NMR (300 MHz, CDCl$_3$): δ 0.89 (3H, d, J=6 Hz), 1.23 (9H, m), 1.40 (15H, m), 1.72 (6H, m), 3.25 (3H, s), 3.58 (2H, m), 3.71 (4H, m), 4.46 (1H, m), 4.83 (1H, m), 5.2 (1H, m), 7.30 (4H, m), 7.63 and 7.67 (1H, s);

C$^{13}$-NMR (75 MHz, CDCl$_3$): 10.4, 13.2, 14.4, 18.7, 20.2, 21.2, 24.2, 24.5, 27.6, 27.7, 27.8, 31.1, 37.5, 41.9, 46.5, 51.6, 54.6, 55.1, 61.8, 82.5, 101.0, 104.7, 114.4, 126.1, 126.2, 129.6, 130.7, 136.4, 154.4, 156.4, 156.5, 158.7, 160.0, 170.8, 174.6;

LC/MS: 2.62 min;

M=704.3 (M+H).

Example 12

Preparation of (S)-2-{5-[N-trifluoroacetyl-N-isopropyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid (12)

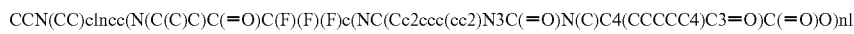

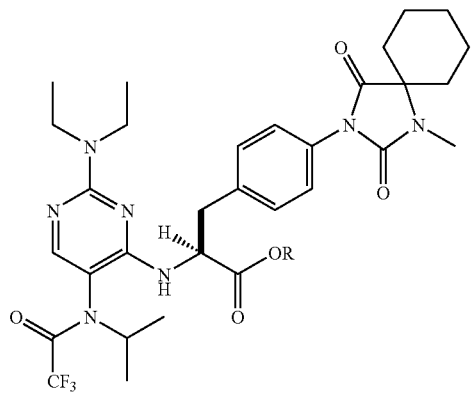

R = tert-Bu or H

Example 12 was prepared by Steps 1, 2, 3, and 4 (using 1-methylaminocyclohexane-1-carboxylic acid methyl ester hydrochloride, as prepared in Example 8), and then Methods A, B, E, and M.

LC/MS: 2.37 min, M=648.3 (M+H).

R=tert-Bu: $H^1$-NMR (300 MHz, CDCl$_3$): δ 1.03–1.40 (20H, m), 1.76 (6H, m), 2.1 (2H, m), 2.75 (1H, m), 2.91 (3H, m), 3.27 (3H, m), 3.62 (4H, m), 4.0 (1H, m), 4.78 (1H, m), 7.30 (4H, m), 7.7 and 7.73 (1H, s);

$C^{13}$-NMR (75 MHz, CDCl$_3$): 11.9, 12.0, 21.2, 24.2, 24.5, 27.9, 27.9, 31.1, 37.0, 37.4, 42.7, 44.8, 44.9, 53.4, 54.8, 55.3, 61.8, 61.8, 82.8, 107.9, 117.9, 126.2, 129.5, 130.9, 135.9, 136.1, 154.3, 157.6, 170.1, 170.3, 174.5;

LC/MS: 2.81 min;
M=690.3 (M+H).

Example 13

Preparation of (S)-2-{5-[N-trifluoroacetyl-N-ethyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid (13)

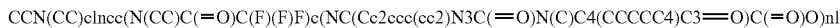

CCN(CC)c1ncc(N(CC)C(=O)C(F)(F)F)c(NC(Cc2ccc(cc2)N3C(=O)N(C)C4(CCCCC4)C3=O)C(=O)O)n1

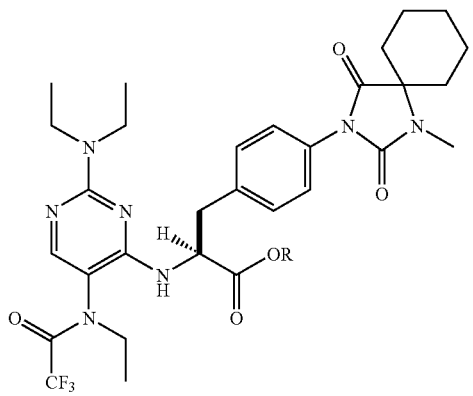

R = tert-Bu or H

Example 13 was prepared by Steps 1, 2, 3, and 4 (using 1-methylaminocyclohexane-1-carboxylic acid methyl ester hydrochloride, as prepared in Example 8), and then Methods A, H, I, and M.

$H^1$-NMR (300 MHz, CDCl$_3$): δ1.01–1.14 (11H, brm), 1.73 (6H, brm), 2.01 (2H, brm), 2.68 (1H, m), 2.87 (3H, s), 3.11–3.51 (6H, brm), 3.95 (1H, brm), 4.91 (1H, brm), 7.21 (4H, brm), 7.80 and 7.90 (1H, s);

$C^{13}$-NMR (75 MHz, CDCl$_3$): 11.7, 12.8, 21.1, 24.2, 24.5, 31.1, 36.9, 42.9, 44.4, 56.0, 61.8, 108.4, 114.1, 117.9, 126.1, 129.6, 130.4, 130.5, 137.0, 154.4, 154.4, 157.3, 157.9, 174.5, 174.9;

LC/MS: 2.29 min;
M=634.2 (M+H).

Example 14

Preparation of (S)-2-{5-[2,5-bis(N',N'-diethylamino)-pyrimidin-4-ylamino}-3-[4-(3-methyl-4-(4-methyl-2,4-diaza-spiro[4.5]decane-1,3-dion-2-yl)-2, 5-dioxoimidazolidin-1-yl)phenyl]propanoic acid (14)

CCN(CC)c1cnc(ncINC(Cc2ccc(cc2)N3C(=O)N(C)C4(CCCCC4)C3=O)C(=O)O)N(CC)CC

-continued

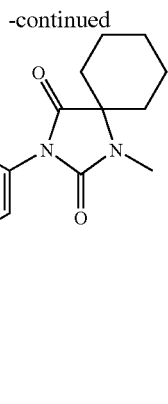

Example 14 was prepared by Steps 1, 2, 3, and 4 (using 1-methylaminocyclohexane-1-carboxylic acid methyl ester hydrochloride, as prepared in Example 8), and then Methods A, H, I, J, L, and M.

$H^1$-NMR (300 MHz, CDCl$_3$): δ 0.88 (6H, t, J=9 Hz), 1.18 (8H, m), 1.75 (6H, brm), 2.10 (2H, m), 2.71 (4H, m), 2.91 (3H, s), 3.25–3.53 (6H, m), 4.81 (1H, m), 7.26 (4H, m), 7.40 (1H, brd, J=6 Hz), 7.57 (1H, s);

$C^{13}$-NMR (75 MHz, CDCl$_3$): 12.3, 12.8, 21.2, 24.2, 24.5, 31.1, 47.9, 55.6, 61.8, 121.1, 126.0, 129.8, 130.5, 136.7, 150.4, 154.4, 160.4, 165.8, 174.2, 174.5. LC/MS: 2.41 min; M=566.3 (M+H).

Example 15

Preparation of (S)-2-{5-[N-trifluoroacetyl-N-ethyl-amino]-2-(N',N'-diethylamino)-pyrimidin-4-ylamino}-3-[4-(4-methyl-4,6-diaza-spiro[2.4]hep-tane-5,7-dione-6-yl)phenyl]propanoic acid CCN(CC)c1ncc(N(CC)C(=O)C(F)(F)F)c(NC(Cc2ccc(cc2)N3C(=O)N(C)C4(CC4)C3=O)C(=O)O)n1

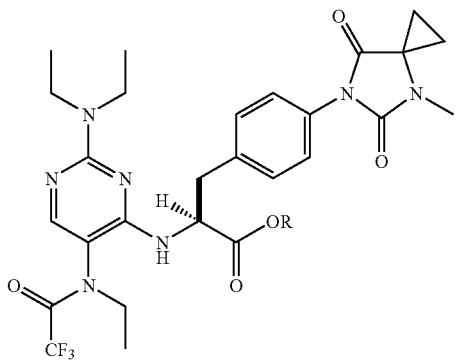

Example 15 was prepared by Steps 1, 2, 3, and 4 (using 1-methylaminocyclopropane-1-carboxylic acid methyl ester hydrochloride), and then Methods A, H, I, and M.

LC/MS: 1.83 min, M=592.2 (M+H).

Example 16

Preparation of (S)-2-{5-[N-(pyrrolidinyl-carbonyl)-N-ethyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid (16)

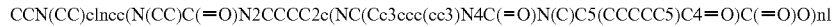

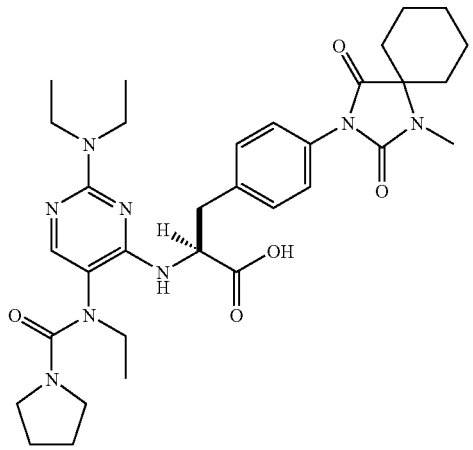

Example 16 was prepared by Steps 1, 2, 3, and 4 (using 1-methylaminocyclohexane-1-carboxylic acid hydrochloride), and then Methods A, H, I, J, K (using 1-pyrrolidinecarbonyl chloride), and M.

H$^1$-NMR (300 MHz, CDCl$_3$): δ1.03–1.22 (11H, m), 1.76 (10H, m), 2.10 (2H, m), 2.92 (3H, s), 3.1–3.58 (12H, m), 4.96 (1H, m), 7.26 (4H, m), 7.81 (1H, s). LC/MS: 2.39 min, M=635.3 (M+H).

R=tert-Bu: H$^1$-NMR (300 MHz, CDCl$_3$): δ 1.06–1.40 (20H, m), 1.75 (6H, m), 2.10 (2H, m), 2.92, (3H, s), 3.05–3.20 (4H, m), 3.58 (4H, m), 5.26 (1H, m), 7.05–7.65 (7H, m);

C$^{13}$-NMR (75 MHz, CDCl$_3$): 13.2, 14.2, 21.0, 21.2, 24.2, 24.5, 27.9, 27.9, 31.2, 37.9, 41.9, 54.2, 60.4, 61.7, 82.0, 83.3, 111.2, 111.3, 111.4, 125.9, 126.1, 129.6, 130.5, 136.2, 144.8, 154.4, 157.7, 170.8, 174.5;

LC/MS: 2.88 min;

M=688.3 (M+H).

Example 17

Preparation of (S)-2-{5-[N-(furan-2-ylcarbonyl)-N-ethyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid (17)

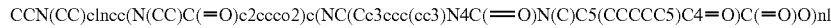

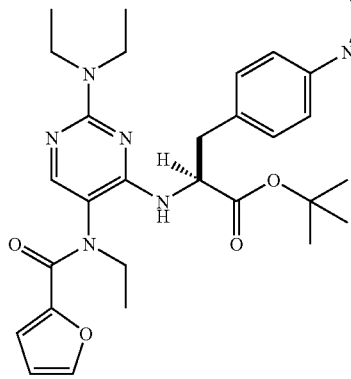

R = tert-Bu or H

Example 17 was prepared by Steps 1, 2, 3, and 4 (using 1-methylaminocyclohexane-1-carboxylic acid methyl ester hydrochloride, as prepared in Example 8), and then Methods A, H, I, J, K (using 2-furoyl chloride which was prepared by reaction of 2-furoic acid and oxalyl chloride in the presence of catalytic DMF), and M.

$H^1$-NMR (300 MHz, CDCl$_3$): δ 1.48 (11H, brm), 1.74 (6H, brm), 2.02 (2H, m), 2.89 (3H, s), 3.01–3.93 (8H, m), 5.2 (1H, m), 6.21–6.73 (2H, m), 7.10–7.61 (5H, m).

$C^{13}$-NMR (75 MHz, CDCl$_3$): 12.4, 12.6, 21.1, 24.3, 24.5, 31.1, 36.9, 43.6, 61.9, 102.3, 111.8, 112.8, 125.2, 126.2, 129.6, 137.0, 142.1, 144.2, 145.7, 151.8, 154.5, 164.9, 174.6. LC/MS: 2.38 min, M=632.3 (M+H).

Example 18

Preparation of (S)-2-{5-[N-trifluoroacetyl-N-ethyl-amino]-2-(N',N'-diethylamino)-pyrimidin-4-ylamino}-3-[4-(3-ethyl-4-(4-methyl-2,4-diaza-spiro[4.5]decane-1,3-dion-2-yl]-2,5-dioxoimidazolidin-1-yl)phenyl]propanoic acid (18)

CCN(CC)c1ncc(N(CC)C(=O)C(F)(F)F)c(NC(Cc2ccc(cc2)N3C(=O)N(CC)C4(CCCCC4)C3=O)C(=O)O)n1

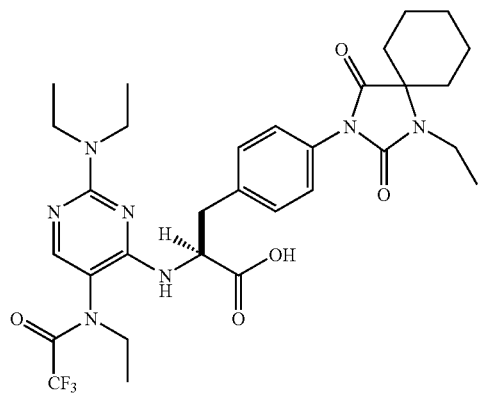

Example 18 was prepared by Steps 1, 2, 3, and 4 (using 1-ethylaminocyclohexane-1-carboxylic acid methyl ester hydrochloride), and then Methods A, H, I, and M.

1-Ethylaminocyclohexane-1-carboxylic acid methyl ester hydrochloride was prepared by the same methods as 1-methylaminocyclohexane-1-carboxylic acid methyl ester hydrochloride, substituting ethylamine hydrochloride for methylamine hydrochloride, in the first step.

LC/MS: 2.57 min, M=648.3 (M+H).

Example 19

Preparation of (S)-2-{5-(2,2,2-trifluoroethyl)-2-(N',N'-diethylamino)-pyrimidin-4-ylamino}-3-[4-(1,3-dioxo-(S)-tetrahydro-2H-pyrrolo[1,2-e]imidazol-2-yl)phenyl]propanoic acid (19)

CCN(CC)c1ncc(CC(F)(F)F)c(NC(Cc2ccc(cc2)N3C(=O)C4CCCN4C3=O)C(=O)O)n1

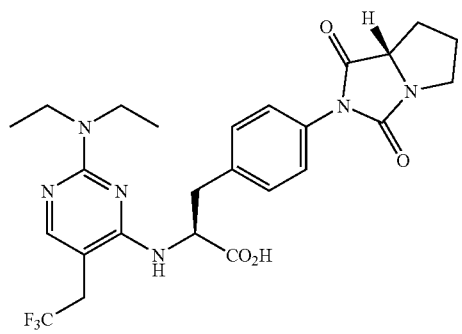

Compound 19 was prepared as shown in Scheme IV below.

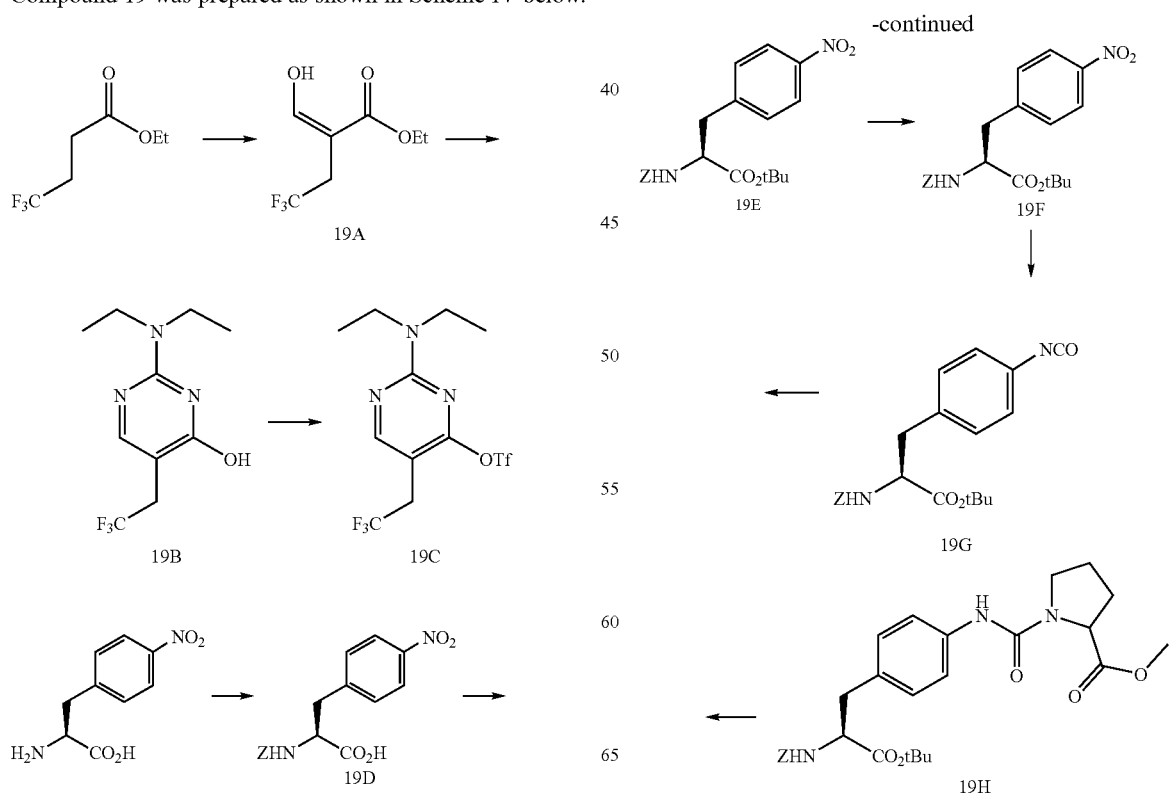

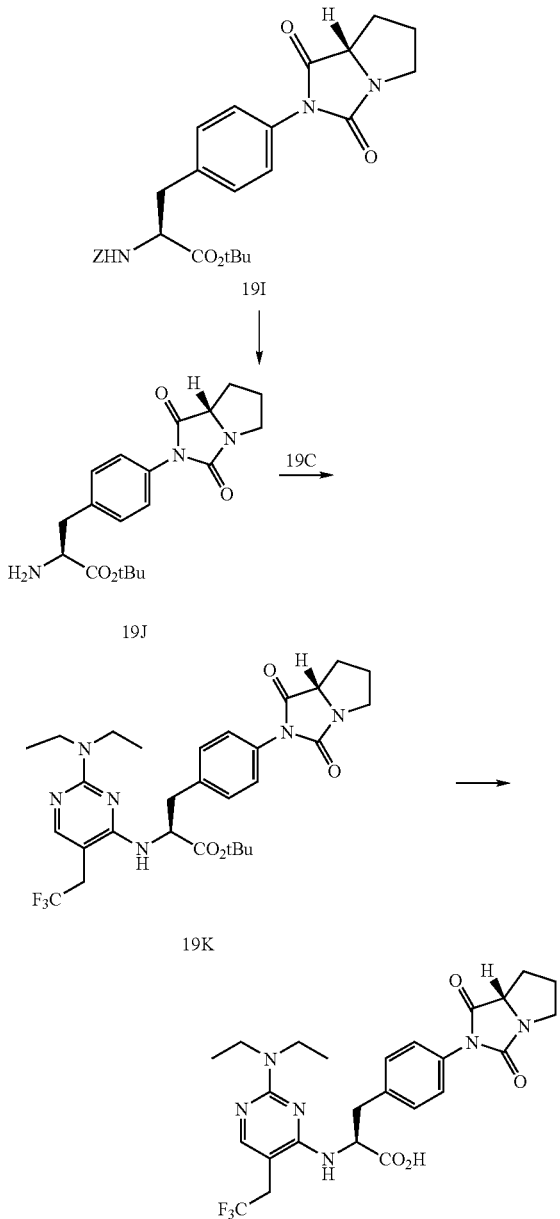

Preparation of 19A

To an ice chilled solution of ethyl trifluorobutyrate (15 g, 89 mmol) and ethyl formate (36 mL, 444 mmol) in THF (200 mL) under $N_2$ was added a solution of 1 M KOtBu in THF (107 mmol, 107 mL) over a 25-minute period. After 15 minutes the ice bah was removed and the reaction mixture was stirred one hour at room temperature. Additional ethyl formate (18 mL, 222 mmol) was then added and the reaction mixture was stirred overnight. The reaction mixture was concentrated and the residue partitioned between cold ether (100 mL) and cold water (300 mL). The pH of the aqueous phase was adjusted to 2 with concentrated HCl. The product was extracted with dichloromethane (1×100 mL, 45×75 mL) and the combined organic extracts were washed with brine (1×100 mL), dried (MgSO$_4$), filtered, and concentrated to yield a thick oil which solidified upon standing, 10.2 g (58.5%) 19A. MS (m/z)=198 (M+H)$^+$.

Preparation of 19B

To a solution of 19A (10 g, 51 mmol) and diethylguanidine sulfate (8.3 g, 25.2 mmol) in EtOH (60 mL) under $N_2$, was added NaOEt, 21% solution in EtOH (20.7 mL, 55.5 mmol) over a 10-minute period. The reaction mixture was then heated at reflux for 5 hours. The heterogeneous solution was cooled and poured into cold water (100 mL) to give a homogenous solution. The pH of the solution was adjusted to approximately 3.5 with conc. HCl and 1 N HCl. A solid precipitated from solution, which was collected by filtration. The light tan solid was washed with water and air-dried, 2.9 g, (23%) 19B. MS (m/z)=250 (M+H). $^1$H NMR (CD$_3$OD) δ 7.65 (br s, 1H), 3.55 (q, 4H), 3.30 (q, 2H), 1.25 (t, 6H).

Preparation of 19C

A flask was charged with 19B (2.0 g, 8.02 mmol), diisopropylethylamine (1.5 mL, 8.83 mmol), DMAP (0.98 g, 0.8 mmol), and dichloromethane (30 mL). The mixture was cooled to 0° C. and trifluoroacetic anhydride (1.5 mL, 8.83 mmol) was added. The reaction became homogeneous and was stirred at 0° C. for 3 hours. The mixture was quenched with sat. NaHCO$_3$ and extracted with dichloromethane. The organic phase was washed with 0.2 N citric acid, dried over Na$_2$SO$_4$, filtered, and concentrated in vacuo to yield 2.87 g (94%) 19C as a brown solid. $^1$H NMR (CDCl$_3$) δ 8.28 (s, 1H), 3.65–3.52 (m, 4H), 3.29–3.19 (q, 2H), 1.22–1.17 (t, 6H).

Preparation of 19D

Sodium hydroxide (10 g, 0.25 mol) was dissolved in water (300 mL). To this solution the 4-nitrophenylalanine (50.3 g, 0.22 mol) was added and stirred until complete dissolution. To the resulting solution the sodium carbonate (28.8 g, 0.26 mol) was added and stirred suspension was cooled in an ice bath to +8° C. The benzyl chloroformate (44.7 g, 0.26 mol) was added drop wise with vigorous stirring, maintaining internal temperature in +6° to +9° C. range. The mixture was stirred at +6° C. for additional 1 hr, transferred to the separatory funnel and washed with ether (2×150 mL). Aqueous phase was placed in a large Erlenmeyer flask (2 L) and was cautiously acidified with dil. aq. HCl to pH=2 and extracted with ethyl acetate (4×500 mL). The combined extracts were washed with water and dried with MgSO$_4$. The solution was filtered and filtrate evaporated, residue was dissolved in ethyl acetate (150 mL) and diluted with hexane (500 mL). Crystalline material was filtered off and rinsed with cold solvent, air dried to give Cbz-4-nitrophenylalanine, 75 g (99.5% yield) 19D. $^1$H-NMR, DMSO-d6, (δ): 12.85 (bs, 1H), 8.12 (d, 2H, J=9 Hz), 7.52 (d, 2H, J=9 Hz), 7.30 (m, 5H), 4.95 (s, 2H), 4.28 (m, 1H), 3.32 (bs, 11H), 3.10 (m, 2H). $^{13}$C-NMR (δ): 173.1, 156.3, 146.6, 137.3, 130.8, 128.5, 128.0, 127.8, 123.5, 65.6, 55.1, 36.6. MS (m/z): 367.1 [M+23].

Preparation of 19E

The Cbz-4-nitrophenylalanine, 19D, (75 g, 0.22 mol) was dissolved in dioxane (300 mL). The resulted stirred solution was cooled in dry ice bath to −20° C. (internal). The liquefied isobutylene (approx. 290 mL) was added followed by conc. sulfuric acid (35 mL) added in three equal portions, 30 min apart. The addition of acid is a very exothermic process, accompanied by substantial degree of polymerization. Efficient mechanical stirring is essential at this stage. Resulted mixture was stirred for 20 hr, allowing to warm up to ambient temperature then was cautiously poured into sat. aq. sodium carbonate solution (2 L) and diluted with ethyl acetate (600 mL). Organic layer was separated and aqueous layer was extracted with ethyl acetate (2×200 mL). Combined extracts were washed with water and dried with sodium sulfate. Obtained solution was filtered and evaporated to dryness. Residue was taken up in ethyl acetate/hexane mixture (500 mL; 1:1) and filtered through plug of silica gel (ca. 2×2 inches). Silica was rinsed with additional amount of the same solvent (2 L total) and filtrates were evaporated to give fully protected 4-nitrophenylalanine as a viscous oil, 73 g (83% after two steps) 19E. $^1$H-NMR, CDCl$_3$, (δ): 8.12 (d, 2H, J=8.4 Hz), 7.36 (m, 7H), 5.35 (m, 1H), 5.10 (m, 2H), 4.57 (m, 1H), 3.31 (m, 2H), 1.43 (s, 9H). $^{13}$C-NMR, CDCl$_3$, (δ): 169.7, 155.3, 146.9, 143.9, 136.0, 130.2, 128.4, 128.2, 128.0, 123.3, 82.9, 66.9, 54.7, 38.2, 31.4, 27.8, 13.9.

Preparation of 19F

Protected 4-nitrophenylalanine, 19E, (73 g, 0.18 mol) was dissolved in ethanol (500 mL) and platinum oxide catalyst (1.5 g) was added. Resulted solution was vigorously stirred in hydrogen atmosphere (50–60 psi) at ambient temperature until further hydrogen adsorption ceased (3 hr). Catalyst was filtered off and filtrate was evaporated to dryness, residue was taken up in ethyl acetate (200 mL) and filtered through plug of silica gel (2×2 in) using ethyl acetate-hexane mixture (3:2, 2 L) to rinse silica. The filtrate was concentrated to approx. 200 ml and hexane (500 mL) was added. The crystalline product was filtered off, rinsed with cold solvent and air-dried. Yield—56 g, 84%, 19F. $^1$H-NMR, CDCl$_3$, (δ): 7.30 (bs, 5H), 6.92 (d, 2H, J=8.1 Hz), 6.58 (d, 2H, J=8.1 Hz), 5.21 (m, 1H), 5.10 (d, 2H, J=2.1 Hz), 4.46 (m, 1H), 3.59 (bs, 2H), 2.97 (s, 2H, J=5.4 Hz), 1.42 (s, 9H). $^{13}$C-NMR, CDCl$_3$, (δ): 170.6, 145.1, 136.3, 130.2, 128.3, 127.9, 125.6, 115.0, 81.9, 66.6, 55.2, 37.4, 27.8 MS (m/z): 393.1 [M+23].

Preparation of 19G 19F (0.5 g, 1.3 mmol) was dissolved in CH$_2$Cl$_2$ (13 mL). Saturated NaHCO$_3$ (13 mL) was added and the reaction was stirred vigorously at 0° C. for 30 minutes. Stirring was ceased and the layers were allowed to separate. A 2.0 M solution of phosgene in toluene (5.4 mL, 10.8 mmol) was added to the reaction mixture, which was stirred vigorously for 1 hour, maintaining temperature at 0° C. The layers were separated and the aqueous phase was washed with CH$_2$Cl$_2$ (15 mL). The combined organic layers were washed with brine, dried over Na$_2$SO$_4$, filtered, and concentrated in vacuo to yield 0.55 g (100%) 19G as an oil. MS (m/z) 419, (M+Na)$^+$. $^1$H NMR (CDCl$_3$) δ 7.37–7.34 (m, 3H), 7.26–7.24 (d, 1H), 7.19–7.16 (d, 1H), 7.10–7.07 (d, 2H), 6.99–6.96 (d, 2H), 5.23–5.20 (d, 1H), 5.14–5.04 (m, 2H), 4.51–4.49 (q, 1H), 3.08–3.02 (m, 2H), 1.41 (s, 9H).

Preparation of 19H 19G (0.55 g, 1.4 mmol) was dissolved in CH$_2$Cl$_2$ (2 mL). L-proline hydrochloride (0.35 g, 2.1 mmol) was free based with triethylamine (0.6 mL, 4.2 mmol) and added to the solution above. The reaction was stirred for 18 hours at room temperature. The reaction mixture was dried over Na$_2$SO$_4$, filtered, and concentrated in vacuo to yield 1.03 g (100%) 19H as a white wax. MS (m/z) 526, (M+H)$^+$. $^1$H NMR (CDCl$_3$) δ 7.36–7.19 (m, 7H), 7.01–6.96 (d, 2H), 5.23–5.20 (d, 1H), 5.04 (m, 2H), 4.51–4.49 (m, 1H), 3.71–3.70 (m, 2H), 3.06–2.99 (m, 6H), 1.37–1.31 (m, 12H).

Preparation of 19I

A flask was charged with 19H (1.03 g, 1.96 mmol) dissolved in ethanol (5 mL). Triethylamine (0.4 mL, 2.94 mmol) was added and the reaction was heated at reflux for 3 hours. The reaction was cooled to room temperature and concentrated in vacuo. The residue was taken up in ethyl acetate and washed with 0.2 N citric acid, water, and brine. The organic layer was dried over Na$_2$SO$_4$, filtered, and concentrated in vacuo to yield a yellow residue. The residue was purified by flash chromatography (50% ethyl acetate/hexanes) to yield 0.49 g (51%) 19I as a white foam. $^1$H NMR (CDCl$_3$) δ 7.36–7.31 (m, 6H), 7.26–7.22 (m, 3H), 5.23–5.20 (d, 1H), 5.10 (bs, 2H), 4.51–4.49 (q, 1H), 4.23–4.20 (q, 1H), 3.82–3.72 (m, 1H), 3.38–3.30 (m, 1H), 3.11–3.09 (d, 2H), 2.41–1.78 (m, 4H), 1.39 (s, 9H).

Preparation of 19J

A Parr shaker flask was charged with 19I (0.49 g, 0.99 mmol) and ethanol (5 mL). Palladium on carbon (0.049 g, 10 wt %) was added and the flask was shaken on a hydrogentor (48 psi H$_2$) for 18 hours. The reaction mixture was filtered through a celite plug, and concentrated in vacuo to yield 0.35 g (98%) 19J as a yellow residue. $^1$H NMR (CDCl$_3$) δ 7.33–7.26 (m, 4H), 4.48–2.18 (m, 1H), 3.85–3.65 (m, 1H), 3.62–3.58 (m, 1H), 3.41–3.31 (m, 1H), 3.09–2.80 (m, 2H), 2.41–1.79 (m, 4H), 1.43 (s, 9H).

Preparation of 19K

A flask was charged with 19C (27 mg, 0.07 mmol) and 19J (50 mg, 0.14 mmol) that were dissolved in DMF (0.5 mL) and heated at 110° C. for 48 hours. The reaction mixture was cooled to room temperature and diluted with ethyl acetate and water. The organic layer was collected and washed with 0.2 N citric acid, water, and brine, dried over Na$_2$SO$_4$, filtered, and concentrated in vacuo to yield a brown residue. The residue was purified by thin layer chromatography (50% ethyl acetate:hexanes) to yield 40 mg (97%) 19K as a white solid. MS (m/z) 591, (M+H)$^+$.

Preparation of 19

A flask was charged with 19K (60 mg, 0.10 mmol) and dissolved in formic acid (5 mL). The solution was heated at 40° C. for 18 hours. The mixture was cooled to room temperature and concentrated in vacuo. The residue was purified by preparative HPLC (15–40% CH$_3$CN/H$_2$O over 60 minutes on a Luna 5µ C18(2) column (250×10 mm); uv detector at 230 nm) to yield 10 mg (20%) 19 as a white powder. Rf=0.55 (7/3 methanol:water+0.1% trifluoroacetic acid on Whatman MKC18F Silica Gel 60 Å). MS (m/z) 535, (M+H)$^+$. $^1$H NMR (CD$_3$OD) δ 7.66 (s, 1H), 7.38–7.35 (d, 2H), 7.29–7.26 (d, 2H), 4.35–4.29 (m, 1H), 3.72–3.42 (m, 9H), 2.31–2.03 (m, 4H), 1.91–1.78 (m, 2H), 1.23–1.18 (t, 6H).

Example A

$\alpha_4\beta_1$ Integrin Adhesion Assay: Jurkat™ Cell Adhesion to Human Plasma Fibronectin Procedure:

96 well plates (Costar 3590 EIA plates) were coated with human fibronectin (Gibco/BRL, cat #33016-023) at a concentration of 10 µg/mL overnight at 4° C. The plates were then blocked with a solution of bovine serum albumin (BSA; 0.3%) in saline. Jurkat™ cells (maintained in log phase growth) were labeled with Calcein AM according to the manufacturer's instructions, and suspended at a concentration of 2×106 cells/mL in Hepes/Saline/BSA. The cells were then exposed to test and control compounds for 30 minutes at room temperature before transfer to individual wells of the fibronectin coated plate. Adhesion was allowed to occur for 35 minutes at 37° C. The wells were then washed by gentle aspiration and pipetting with fresh saline. Fluorescence associated with the remaining adherent cells was quantified using a fluorescence plate reader at EX 485/EM 530.

Cell cultures were prepared by first splitting the stationary phase Jurkat™ cells at 1:10 on day one, and 1:2 on day two to perform assay on day 3. The cells split 1:10 on day one were split 1:4 on day 3 for a day 4 assay.

The assay plates were prepared by first making a working solution of Gibco/BRL Human Fibronectin (cat # 33016-023) in PBS++, at 10 µg/mL.

A Costar 3590 EIA plate was then coated with 50 µL/well for 2 hours at room temperature (though it can also be left overnight at 4° C.). Finally the plate was asperated and blocked with Hepes/Saline Buffer, 100 µL/well, for 1 hour at room temperature followed by washing 3 times with 150 µL of PBS++.

Compound dilutions were accomplished by preparing 1:3 serial dilutions of compounds as follows. For each plate (4 compounds/plate) 600 µL were added to 4 Bio-Rad Titertubes in a Titertube rack. Enough compound was added to each appropriate tube to give a 2× concentration using methods well known in the art. Using Falcon Flexiplates, 100 µL of Hepes/Saline buffer or human serum were added to rows B through G. A multi-channel pipetter set to 180 µL was used to with four tips spaced evenly the pipetter. Each set of four tubes was mixed 5 times and 180 µL of 2× compound was transferred to the first column of each compound dilution in Row B, leaving Row A empty. 180 µL were added to the other wells in Row A. Serial dilutions were performed down the plate by transferring 50 µL to the next dilution and mixing 5 times, changing tips each time after mixing. Dilutions were stopped at Row F. Row G had no compound present.

A 20 µg/mL solution in Hepes/Saline buffer or human serum, of 21/6 antibody was the positive control and was set aside in a reagent trough to add to cell suspension plate.

The cell staining was accomplished by first harvesting the log-phase Jurkat™ cells by centrifugation in 50 mL tubes (1100 rpm for 5 minutes). The cells were resuspended in 50 mL PBS++, spun, and resuspend in 20 mL PBS++. The cells were stained by adding 20 µL of Calcein AM for 30 minutes RT. The volume was brought to 50 mL with Hepes/Saline buffer and the cells were counted, spun, and resuspend to 2×106 cells/mL in Hepes/Saline buffer or human serum.

The compounds were incubated using the following procedure. In a new flexiplate, 65 µL of stained cells were added to Rows B through H. Then 65 µL of 2× compounds were added to the appropriate rows following the plate setup and mixed three times. 65 µL of 2×-21/6 antibody were added to Row H and mixed 3×. Finally the plate was incubated at room temperature for 30 minutes.

Fibronectin adhesion was measured using a fluorescent plate reader at EX 485/EM 530 after the following work up procedure. After incubation, the cells were mixed three times and 100 µL were transfered to the Fibronectin coated plates and incubated at 37° C. for about 35 minutes. Each plate was washed, row by row, by gently pipetting 100 µL of RT. PBS++ down the sides of the wells and turning the plate 90 degrees to aspirate. This procedure was repeated for a total of 3 washes. Each well was filled with 100 µL after washing by pipetting down the side of the well.

When tested in this assay, each of the compounds prepared in the above examples has or is expected to have an $IC_{50}$ of 15 µM or less.

Example B

In Vitro Saturation Assay for Determining Binding of Candidate Compounds to $\alpha_4\beta_1$ The following describes an in vitro assay to determine the plasma levels needed for a compound to be active in the Experimental Autoimmune Encephalomyelitis ("EAE") model, described in the next example, or in other in vivo models.

Log-growth Jurkat cells are washed and resuspended in normal animal plasma containing 20 µg/ml of the 15/7 antibody (described in the above example).

The Jurkat cells are diluted two-fold into either normal plasma samples containing known candidate compound amounts in various concentrations ranging from 66 µM to 0.01 µM, using a standard 12 point serial dilution for a standard curve, or into plasma samples obtained from the peripheral blood of candidate compound-treated animals.

Cells are then incubated for 30 minutes at room temperature, washed twice with phosphate-buffered saline ("PBS") containing 2% fetal bovine serum and 1 mM each of calcium chloride and magnesium chloride (assay medium) to remove unbound 15/7 antibody.

The cells are then exposed to phycoerythrin-conjugated goat F(ab')$_2$ anti-mouse IgG Fc (Immunotech, Westbrook, Me.), which has been adsorbed for any nonspecific cross-reactivity by co-incubation with 5% serum from the animal species being studied, at 1:200 and incubated in the dark at 4° C. for 30 minutes.

Cells are washed twice with assay medium and resuspended in the same. They are then analyzed with a standard fluorescence activated cell sorter ("FACS") analysis as described in Yednock et al. J. Biol. Chem., 1995, 270:28740.

The data is then graphed as fluorescence versus dose, e.g., in a normal dose-response fashion. The dose levels that result in the upper plateau of the curve represent the levels needed to obtain efficacy in an in vivo model.

This assay may also be used to determine the plasma levels needed to saturate the binding sites of other integrins, such as the $\alpha_9\beta_1$ integrin, which is the integrin most closely related $\alpha_4\beta_1$ (Palmer et al, 1993, J. Cell Bio., 123:1289). Such binding is predictive of in vivo utility for inflammatory conditions mediated by $\alpha_9\beta_1$ integrin, including by way of example, airway hyper-responsiveness and occlusion that occurs with chronic asthma, smooth muscle cell proliferation in atherosclerosis, vascular occlusion following angioplasty, fibrosis and glomerular scarring as a result of renal disease, aortic stenosis, hypertrophy of synovial membranes in rheumatoid arthritis, and inflammation and scarring that occur with the progression of ulcerative colitis and Crohn's disease.

Accordingly, the above-described assay may be performed with a human colon carcinoma cell line, SW 480 (ATTC #CCL228) transfected with cDNA encoding $\alpha_9$ integrin (Yokosaki et al., 1994, J. Biol. Chem., 269:26691), in place of the Jurkat cells, to measure the binding of the $\alpha_9\beta_1$ integrin. As a control, SW 480 cells which express other $\alpha$ and $\beta_1$ subunits may be used.

Accordingly, another aspect of this invention is directed to a method for treating a disease in a mammalian patient, which disease is mediated by $\alpha_9\beta_1$, and which method comprises administering to said patient a therapeutically effective amount of a compound of this invention. Such compounds are preferably administered in a pharmaceutical composition described herein above. Effective daily dosing will depend upon the age, weight, condition of the patient which factors can be readily ascertained by the attending clinician. However, in a preferred embodiment, the compounds are administered from about 20 to 500 µg/kg per day.

Example C

In Vivo Evaluation

The standard multiple sclerosis model, Experimental Autoimmune (or Allergic) Encephalomyelitis ("EAE"), is used to determine the effect of candidate compounds to reduce motor impairment in rats or guinea pigs. Reduction in motor impairment is based on blocking adhesion between leukocytes and the endothelium and correlates with anti-inflammatory activity in the candidate compound. This model has been previously described by Keszthelyi et al., Neurology, 1996, 47:1053–1059, and measures the delay of onset of disease.

Brains and spinal cords of adult Hartley guinea pigs are homogenized in an equal volume of phosphate-buffered saline. An equal volume of Freund's complete adjuvant (100 mg *mycobacterium tuberculosis* plus 10 mL Freund's incomplete adjuvant) is added to the homogenate. The mixture is emulsified by circulating it repeatedly through a 20 mL syringe with a peristaltic pump for about 20 minutes.

Female Lewis rats (2–3 months old, 170–220 g) or Hartley guinea pigs (20 day old, 180–200 g) are anesthetized with isoflurane and three injections of the emulsion, 0.1 mL each, are made in each flank. Motor impairment onset is seen in approximately 9 days.

Candidate compound treatment began on Day 8, just before onset of symptoms. Compounds are administered subcutaneously ("SC"), orally ("PO") or intraperitoneally ("IP"). Doses are given in a range of 10 mg/kg to 200 mg/kg, bid, for five days, with typical dosing of 10 to 100 mg/kg SC, 10 to 50 mg/kg PO, and 10 to 100 mg/kg IP.

Antibody GG5/3 against $\alpha_4\beta_1$ integrin (Keszthelyi et al., Neurology, 1996, 47:1053–1059), which delays the onset of symptoms, is used as a positive control and is injected subcutaneously at 3 mg/kg on Day 8 and 11.

Body weight and motor impairment are measured daily. Motor impairment is rated with the following clinical score:

| 0 | no change |
| 1 | tail weakness or paralysis |
| 2 | hindlimb weakness |
| 3 | hindlimb paralysis |
| 4 | moribund or dead |

A candidate compound is considered active if it delayed the onset of symptoms, e.g., produced clinical scores no greater than 2 or slowed body weight loss as compared to the control.

Example D

Asthma Model

Inflammatory conditions mediated by $\alpha_4\beta_1$ integrin include, for example, airway hyper-responsiveness and occlusion that occurs with chronic asthma. The following describes an asthma model which can be used to study the in vivo effects of the compounds of this invention treating asthma.

Following the procedures described by Abraham et al, J. Clin. Invest, 93:776–787 (1994) and Abraham et al, Am J. Respir Crit Care Med, 156:696–703 (1997), both of which are incorporated by reference in their entirety. Compounds of this invention are formulated into an aerosol and administered to sheep which are hypersensitive to *Ascaris suum* antigen. Compounds which decrease the early antigen-induced bronchial response and/or block the late-phase airway response, e.g., have a protective effect against antigen-induced late responses and airway hyper-responsiveness ("AHR"), are considered to be active in this model.

Allergic sheep which are shown to develop both early and late bronchial responses to inhaled *Ascaris suum* antigen are used to study the airway effects of the candidate compounds. Following topical anesthesia of the nasal passages with 2% lidocaine, a balloon catheter is advanced through one nostril into the lower esophagus. The animals are then intubated with a cuffed endotracheal tube through the other nostril with a flexible fiberoptic bronchoscope as a guide.

Pleural pressure is estimated according to Abraham (1994). Aerosols (see formulation below) are generated using a disposable medical nebulizer that provides an aerosol with a mass median aerodynamic diameter of 3.2 µm as determined with an Andersen cascade impactor. The nebulizer is connected to a dosimeter system consisting of a solenoid valve and a source of compressed air (20 psi). The output of the nebulizer is directed into a plastic T-piece, one end of which is connected to the inspiratory port of a piston respirator. The solenoid valve is activated for 1 second at the beginning of the inspiratory cycle of the respirator. Aerosols are delivered at VT of 500 ml and a rate of 20 breaths/minute. A 0.5% sodium bicarbonate solution only is used as a control.

To assess bronchial responsiveness, cumulative concentration-response curves to carbachol can be generated according to Abraham (1994). Bronchial biopsies can be taken prior to and following the initiation of treatment and 24 hours after antigen challenge. Bronchial biopsies can be preformed according to Abraham (1994).

An in vitro adhesion study of alveolar macrophages can also be performed according to Abraham (1994), and a percentage of adherent cells is calculated.

Aerosol Formulation

A solution of the candidate compound in 0.5% sodium bicarbonate/saline (w/v) at a concentration of 30.0 mg/mL is prepared using the following procedure:

A. Preparation of 0.5% Sodium Bicarbonate/Saline Stock Solution: 100.0 mL

| Ingredient | Gram/100.0 mL | Final Concentration |
|---|---|---|
| Sodium Bicarbonate | 0.5 g | 0.5% |
| Saline | q.s. ad 100.0 mL | q.s. ad 100% |

Procedure:
1. Add 0.5 g sodium bicarbonate into a 100 mL volumetric flask.
2. Add approximately 90.0 mL saline and sonicate until dissolved.
3. Q.S. to 100.0 mL with saline and mix thoroughly.

B. Preparation of 30.0 mg/mL Candidate Compound: 10.0 mL

| Ingredient | Gram/10.0 mL | Final Concentration |
|---|---|---|
| Candidate Compound | 0.300 g | 30.0 mg/mL |
| 0.5% Sodium Bicarbonate/Saline Stock Solution | q.s. ad 10.0 mL | q.s ad 100% |

Procedure:
1. Add 0.300 g of the candidate compound into a 10.0 mL volumetric flask.
2. Add approximately 9.7 mL of 0.5% sodium bicarbonate/saline stock solution.
3. Sonicate until the candidate compound is completely dissolved.
4. Q.S. to 10.0 mL with 0.5% sodium bicarbonate/saline stock solution and mix thoroughly.

Using a conventional oral formulation, compounds of this invention would be active in this model.

Example E

Allograft Model

Allograft rejection, associated with infiltration of inflammatory cells, is the leading obstacle to long-term allograft survival. Cell surface adhesion molecules facilitate alloantigen recognition in vitro and may be critical for lymphocyte traffic in vivo. The following describes a model which can be used to study the in vivo effects of the compounds of this invention in the control of allograft rejection.

The following procedures are described in Coito et al., *Transplantation* (1998) 65(6):699–706 and in Korom et al., *Transplantation* (1998) 65(6):854–859, both of which are incorporated by reference in their entirety.

Following the procedures described in Coito and Korom, male adult rats weighing approximately 200–250 g are used in this model. Lewis rats are used as the recipients of cardiac allografts from Lewis X Brown Norway rats. Hearts are transplanted into the abdominal great vessels using standard microvascular techniques.

A candidate compound is administered to the transplant recipient in a suitable pharmaceutical carrier for a 7-day course of treatment starting the day of the engraftment. Doses range from 0.3 to 30 mg/kg/day. Control recipients receive the pharmaceutical carrier only. The rats are euthanized and their cardiac allografts are analyzed as described in Coito and Korom.

Using conventional formulations, compounds of this invention would be active in this model.

The invention claimed is:

1. A compound of Formula I:

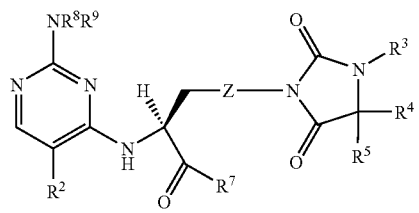

wherein:

Z is selected from the group consisting of aryl, substituted aryl, heteroaryl or substituted heteroaryl;

$R^2$ is selected from the group consisting of hydrogen, alkyl, substituted alkyl, aryl, substituted aryl, heteroaryl, substituted heteroaryl, and —$NRR^1$ wherein each of R and $R^1$ is independently selected from the group consisting of hydrogen, alkyl, substituted alkyl, alkenyl, substituted alkenyl, alkynyl, substituted alkynyl, acyl, aminoacyl, and —$SO_2$—$R^6$, where $R^6$ is selected from the group consisting of alkyl, substituted alkyl, amino, substituted amino, cycloalkyl, substituted cycloalkyl, heterocyclic, substituted heterocyclic, aryl, substituted aryl, heteroaryl, and substituted heteroaryl;

$R^3$, $R^4$ and $R^5$ are independently selected from the group consisting of hydrogen, alkyl, substituted alkyl, alkoxy and substituted alkoxy provided that only one of $R^4$ and $R^5$ is alkoxy or substituted alkoxy;

or $R^3$ and $R^4$ together with the nitrogen atom pendent to $R^3$ and the carbon atom pendant to $R^4$, are cyclized to form a heterocyclic or substitute heterocyclic group;

or $R^4$ and $R^5$ together with the carbon atom pendent thereto are cyclized to form a cycloalkyl, substituted cycloalkyl, heterocyclic, or substituted heterocyclic group;

$R^7$ is selected from the group consisting of hydroxy, alkoxy, substituted alkoxy, phenoxy and substituted phenoxy;

$R^8$ and $R^9$ are independently selected from the group consisting of hydrogen, alkyl, substituted alkyl, cycloalkyl, and substituted cycloalkyl or $R^8$ and $R^9$, together with the nitrogen atom pendent thereto, form a heterocyclic or substituted heterocyclic group;

or a stereoisomer or a pharmaceutically acceptable salt thereof.

2. A compound according to claim 1 which compound is represented by Formula Ia:

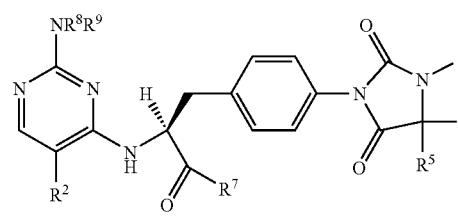

wherein:
R² is selected from the group consisting of hydrogen, alkyl, substituted alkyl, aryl, substituted aryl, heteroaryl, substituted heteroaryl, and —NRR¹ wherein each of R and R¹ is independently selected from the group consisting of hydrogen, alkyl, substituted alkyl, alkenyl, substituted alkenyl, alkynyl, substituted alkynyl, acyl, aminoacyl, and —SO₂—R⁶, where R⁶ is selected from the group consisting of alkyl, substituted alkyl, amino, substituted amino, cycloalkyl, substituted cycloalkyl, heterocyclic, substituted heterocyclic, aryl, substituted aryl, heteroaryl, and substituted heteroaryl;

R³, R⁴ and R⁵ are independently selected from the group consisting of hydrogen, alkyl, substituted alkyl, alkoxy and substituted alkoxy provided that only one of R⁴ and R⁵ is alkoxy or substituted alkoxy;

or R³ and R⁴ together with the nitrogen atom pendent to R³ and the carbon atom pendant to R⁴, are cyclized to form a heterocyclic or substitute heterocyclic group;

or R⁴ and R⁵ together with the carbon atom pendent thereto are cyclized to form a cycloalkyl, substituted cycloalkyl, heterocyclic, or substituted heterocyclic group;

R⁷ is selected from the group consisting of hydroxy, alkoxy, substituted alkoxy, phenoxy and substituted phenoxy;

R⁸ and R⁹ are independently selected from the group consisting of hydrogen, alkyl, substituted alkyl, cycloalkyl, and substituted cycloalkyl or R⁸ and R⁹, together with the nitrogen atom pendent thereto, form a heterocyclic or substituted heterocyclic group;

or a stereoisomer or a pharmaceutically acceptable salt thereof.

3. A compound according to claim 1 which compound is represented by Formula Ib:

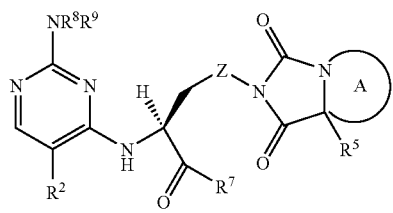

Ib wherein:
Z is selected from the group consisting of aryl, substituted aryl, heteroaryl or substituted heteroaryl;

R² is selected from the group consisting of hydrogen, alkyl, substituted alkyl, aryl, substituted aryl, heteroaryl, substituted heteroaryl, and —NRR¹ wherein each of R and R¹ is independently selected from the group consisting of hydrogen, alkyl, substituted alkyl, alkenyl, substituted alkenyl, alkynyl, substituted alkynyl, acyl, aminoacyl, and —SO₂—R⁶, where R⁶ is selected from the group consisting of alkyl, substituted alkyl, amino, substituted amino, cycloalkyl, substituted cycloalkyl, heterocyclic, substituted heterocyclic, aryl, substituted aryl, heteroaryl, and substituted heteroaryl;

R⁵ is selected from the group consisting of hydrogen, alkyl, substituted alkyl, alkoxy and substituted alkoxy;

A is a 3 to 6 membered heterocyclic or substitute heterocyclic group;

R⁷ is selected from the group consisting of hydroxy, alkoxy, substituted alkoxy, phenoxy and substituted phenoxy;

R⁸ and R⁹ are independently selected from the group consisting of hydrogen, alkyl, substituted alkyl, cycloalkyl, and substituted cycloalkyl or R⁸ and R⁹, together with the nitrogen atom pendent thereto, form a heterocyclic or substituted heterocyclic group;

or a stereoisomer or a pharmaceutically acceptable salt thereof.

4. A compound according to claim 1 which compound is represented by Formula Ic:

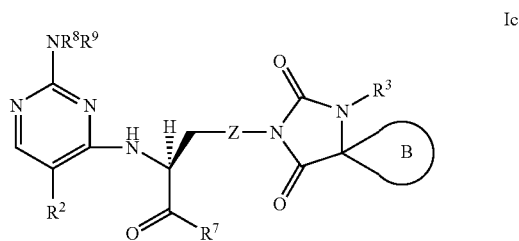

Ic wherein:
Z is selected from the group consisting of aryl, substituted aryl, heteroaryl or substituted heteroaryl;

R² is selected from the group consisting of hydrogen, alkyl, substituted alkyl, aryl, substituted aryl, heteroaryl, substituted heteroaryl, and —NRR¹ wherein each of R and R¹ is independently selected from the group consisting of hydrogen, alkyl, substituted alkyl, alkenyl, substituted alkenyl, alkynyl, substituted alkynyl, acyl, aminoacyl, and —SO₂—R⁶, where R⁶ is selected from the group consisting of alkyl, substituted alkyl, amino, substituted amino, cycloalkyl, substituted cycloalkyl, heterocyclic, substituted heterocyclic, aryl, substituted aryl, heteroaryl, and substituted heteroaryl;

R³ is selected from the group consisting of hydrogen, alkyl, substituted alkyl, alkoxy;

B is a 3 to 6 membered cycloalkyl, substituted cycloalkyl, heterocyclic, or substituted heterocyclic group;

R⁷ is selected from the group consisting of hydroxy, alkoxy, substituted alkoxy, phenoxy and substituted phenoxy;

R⁸ and R⁹ are independently selected from the group consisting of hydrogen, alkyl, substituted alkyl, cycloalkyl, and substituted cycloalkyl or R⁸ and R⁹, together with the nitrogen atom pendent thereto, form a heterocyclic or substituted heterocyclic group;

or a stereoisomer or a pharmaceutically acceptable salt thereof.

5. A compound according to claim 1, wherein Z is a 6-membered aryl, substituted aryl, heteroaryl, or substituted heteroaryl group.

6. A compound of claim 1, wherein Z is selected from phenyl, substituted phenyl, pyridine, substituted pyridine, pyridazine, substituted pyridazine, pyrazine, and substituted pyrazine.

7. A compound according to claim 1, wherein R² is selected from alkyl, aryl and —NRR¹ wherein each of R and R¹ is independently selected from the group consisting of hydrogen, alkyl, substituted alkyl, alkenyl, substituted alkenyl, alkynyl, substituted alkynyl, acyl, aminoacyl, and —SO₂—R⁶, where R⁶ is selected from the group consisting of alkyl, substituted alkyl, amino, substituted amino, cycloalkyl, substituted cycloalkyl, heterocyclic, substituted heterocyclic, aryl, substituted aryl, heteroaryl, and substituted heteroaryl.

8. A compound according to claim 7, wherein $R^2$ is 2,2,2-trifluoroethyl or $R^2$ is —$NRR^1$ where $R^1$ is selected from 4-fluorophenylsulfonyl, acetyl, methylsulfonyl, trifluoroacetyl, ethyl, pyrrolidinyl-carbonyl, and furan-2-oyl.

9. A compound according to claim 1, wherein $R^8$ and $R^9$ are independently selected from methyl and ethyl.

10. A compound according to claim 9, wherein $R^8$ and $R^9$ are ethyl.

11. A compound according to claim 1, wherein $R^7$ is hydroxyl, methoxy or ethoxy.

12. A compound according to claim 1, wherein $R^3$ is methyl or ethyl.

13. A compound according to claim 1, wherein $R^4$ is hydrogen or methyl.

14. A compound according to claim 1, wherein $R^5$ is hydrogen or methyl.

15. A compound according to claim 3, wherein A is pyrrolidine ring.

16. A compound according to claim 4, wherein B is a cyclopropyl or cyclohexyl.

17. A compound selected from the group consisting of
(S)-2-{5-[N-(4-fluorophenylsulfonyl)-N-methyl-amino]-2-(N',N'-diethylamino)-pyrimidin-4-ylamino}-3-[4-(3,4,4-trimethyl-2,5-dioxoimidazolidin-1-yl)phenyl]propanoic acid;
(S)-2-{5-[N-(4-fluorophenylsulfonyl)-N-methyl-amino]-2-(N',N'-diethylamino)-pyrimidin-4-ylamino}-3-[4-(1,3-dioxo-(S)-tetrahydro-2H-pyrrolo[1,2-e]imidazol-2-yl)phenyl]propanoic acid;
(S)-2-{5-[N-(4-fluorophenylsulfonyl)-N-methyl-amino]-2-(N',N'-diethylamino)-pyrimidin-4-ylamino}-3-[4-(3-methyl-2,5-dioxoimidazolidin-1-yl)phenyl]propanoic acid;
(S)-2-{5-[N-acetyl-N-isopropyl-amino]-2-(N',N'-diethylamino)-pyrimidin-4-ylamino}-3-[4-(1,3-dioxo-(S)-tetrahydro-2H-pyrrolo[1,2-e]imidazol-2-yl)phenyl]propanoic acid;
(S)-2-{5-[N-acetyl-N-isopropyl-amino]-2-(N',N'-diethylamino)-pyrimidin-4-ylamino}-3-[4-(1,3-dioxo-(R)-tetrahydro-2H-pyrrolo[1,2-e]imidazol-2-yl)phenyl]propanoic acid;
(S)-2-{5-[N-(methylsulfonyl)-N-isopropyl-amino]-2-(N',N'-diethylamino)-pyrimidin-4-ylamino}-3-[4-(1,3-dioxo-(S)-tetrahydro-2H-pyrrolo[1,2-e]imidazol-2-yl)phenyl]propanoic acid;
(S)-2-{5-[N-acetyl-N-ethyl-amino]-2-(N',N'-diethylamino)-pyrimidin-4-ylamino}-3-[4-(4-methyl-4,6-diaza-spiro[2.4]heptane-5,7-dione-6-yl)phenyl]propanoic acid;
(S)-2-{5-[N-acetyl-N-ethyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid;
(S)-2-{5-[N-(methylsulfonyl)-N-isopropyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid;
(S)-2-{5-[N-(methylsulfonyl)-N-isopropyl-amino]-2-(N',N'-diethylamino)-pyrimidin-4-ylamino}-3-[4-(4-methyl-4,6-diaza-spiro[2.4]heptane-5,7-dione-6-yl)phenyl]propanoic acid;
(S)-2-{5-[N-trifluoroacetyl-N-isopropyl-amino]-2-(N',N'-diethylamino)-pyrimidin-4-ylamino}-3-[4-(4-methyl-4,6-diaza-spiro[2.4]heptane-5,7-dione-6-yl)phenyl]propanoic acid;
(S)-2-{5-[N-trifluoroacetyl-N-isopropyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid;
(S)-2-{5-[N-trifluoroacetyl-N-ethyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid;
(S)-2-{5-[2,5-bis(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid;
(S)-2-{5-[N-trifluoroacetyl-N-ethyl-amino]-2-(N',N'-diethylamino)-pyrimidin-4-ylamino}-3-[4-(4-methyl-4,6-diaza-spiro[2.4]heptane-5,7-dione-6-yl)phenyl]propanoic acid;
(S)-2-{5-[N-(pyrrolidinyl-carbonyl)-N-ethyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid;
(S)-2-{5-[N-(furan-2-ylcarbonyl)-N-ethyl-amino]-2-(N',N'-diethylamino)-pyrimidin-4-ylamino}-3-[4-(3-methyl-4-(4-methyl-2,4-diaza-spiro[4.5]decane-1,3-dion-2-yl)-2,5-dioxoimidazolidin-1-yl)phenyl]propanoic acid;
(S)-2-{5-[N-trifluoroacetyl-N-ethyl-amino]-2-(N',N'-diethylamino)-pyrimidin-4-ylamino}-3-[4-(3-ethyl-4-(4-methyl-2,4-diaza-spiro[4.5]decane-1,3-dion-2-yl)-2,5-dioxoimidazolidin-1-yl)phenyl]propanoic acid; and
(S)-2-{5-(2,2,2-trifluoroethyl)-2-(N',N'-diethylamino)-pyrimidin-4-ylamino}-3-[4-(1,3-dioxo-(S)-tetrahydro-2H-pyrrolo[1,2-e]imidazol-2-yl)phenyl]propanoic acid;
or a stereoisomer or a pharmaceutically acceptable salt thereof.

18. A pharmaceutical composition comprising a pharmaceutically acceptable carrier and an effective amount of a compound according to claim 1.

19. A method of treating rheumatoid arthritis and asthma in a mammal in need of treatment, which method comprises administering the pharmaceutical composition of claim 18.

* * * * *